United States Patent
Dumas et al.

(10) Patent No.: US 6,903,101 B1
(45) Date of Patent: Jun. 7, 2005

(54) SUBSTITUTED PYRIDAZINES AND FUSED PYRIDAZINES WITH ANGIOGENESIS INHIBITING ACTIVITY

(75) Inventors: Jacques P. Dumas, Orange, CT (US); Stephen James Boyer, Fairfield, CT (US); Teddy Kite Joe, New York, NY (US); Holia N. Hatoum-Mokdad, Hamden, CT (US); Harold C. E. Kluender, Trumbull, CT (US); Wendy Lee, Hamden, CT (US); Dhanapalan Nagarathnam, Bethany, CT (US); Robert N. Sibley, North Haven, CT (US); Ning Su, Milford, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 85 days.

(21) Appl. No.: 09/636,519

(22) Filed: Aug. 10, 2000

(51) Int. Cl.[7] .................. C07D 401/08; C07D 401/12; C07D 403/12; A61K 31/502; A61P 35/00
(52) U.S. Cl. ............... 514/252.02; 514/252.03; 544/237; 544/238
(58) Field of Search ............... 544/237, 252.02, 544/252.03; 514/252.02, 252.03

(56) References Cited

U.S. PATENT DOCUMENTS

| | | | |
|---|---|---|---|
| 3,753,988 A | 8/1973 | Rodway et al. | 260/250 |
| 5,089,494 A | 2/1992 | Iwase et al. | 514/248 |
| 5,324,727 A | 6/1994 | Iwase et al. | 514/234.5 |
| 5,849,741 A | 12/1998 | Watanabe et al. | 514/248 |
| 6,258,812 B1 * | 7/2001 | Bold et al. | 544/238 |
| 6,288,064 B1 | 9/2001 | Watanabe et al. | 514/248 |

FOREIGN PATENT DOCUMENTS

| | | |
|---|---|---|
| EP | 0534443 A1 | 3/1993 |
| EP | 0722936 | 7/1996 |
| EP | 0682947 | 9/1997 |
| EP | 0534443 B1 | 12/1998 |
| EP | 0920868 | 6/1999 |
| WO | 9807430 | 2/1998 |
| WO | 9835958 | 8/1998 |
| WO | 9852944 | 11/1998 |
| WO | 9858929 | 12/1998 |
| WO | 9911628 | 3/1999 |

OTHER PUBLICATIONS

Jayson, H. J., Expert Opin. Biol. Ther. 1(4): 703–718, 2001.*

Chemical Abstract: 115:256197; Uenishi, Keiji; Kosegi, Koji; Asaumi, Yoshio; Ishizuka, Yasuhiro; Yaginuma, Hideya; "Preparations of 1–(3–pyridylmethyl)phthalazines as blood platelet aggregation inhibitors", Jpn.Kokai Tokkyo Koho, 6 pp.

* cited by examiner

*Primary Examiner*—Venkataraman Balasubramanian

(57) ABSTRACT

Substituted and Fused pyridazines having angiogenesis inhibiting activity and the generalized structural formula

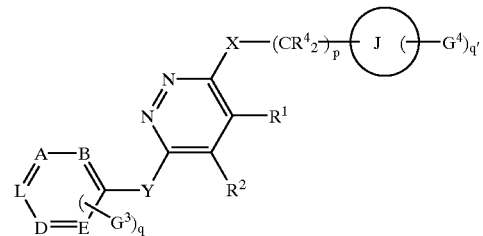

wherein the ring containing A, B, D, E, and L is a nitrogen-containing heterocycle; groups X and Y may be any of a variety of defined linking units; $R^1$ and $R^2$ may be defined independent substituents or together may be a ring-defining bridge; ring J may be an aryl, pyridyl, or cycloalkyl group; and G groups may be any of a variety of defined substituents. Pharmaceutical compositions containing these materials, and methods of treating a mammal having a condition characterized by abnormal angiogenesis or hyperpermiability processes using these materials are also disclosed.

22 Claims, No Drawings

SUBSTITUTED PYRIDAZINES AND FUSED PYRIDAZINES WITH ANGIOGENESIS INHIBITING ACTIVITY

This application claims the benefit of U.S. Provisional Application No: 60/240,925 filed Aug. 10, 1999.

FIELD

This application relates to small molecule heterocyclic pharmaceuticals, and more particularly, to substituted and fused pyridazines having angiogenesis inhibiting activity.

BACKGROUND

Vasculogenesis involves the de novo formation of blood vessels from endothelial cell precursors or angioblasts. The first vascular structures in the embryo are formed by vasculogenesis. Angiogenesis involves the development of capillaries from existing blood vessels, and is the principle mechanism by which organs, such as the brain and the kidney are vascularized. While vasculogenesis is restricted to embryonic development, angiogenesis can occur in the adult, for example during pregnancy, the female cycle, or wound healing.

One major regulator of angiogenesis and vasculogenesis in both embryonic development and some angiogenic-dependent diseases is vascular endothelial growth factor (VEGF; also called vascular permeability factor, VPF). VEGF represents a family of mitogens isoforms resulting from alternative mRNA splicing and which exist in homodimeric forms. The VEGF KDR receptor is highly specific for vascular endothelial cells (for reviews, see: Farrara et al. *Endocr. Rev.* 1992, 13, 18; Neufield et al. *FASEB J.* 1999, 13, 9).

VEGF expression is induced by hypoxia (Shweiki et al. *Nature* 1992, 359, 843), as well as by a variety of cytokines and growth factors, such as interleukin-1, interleukin-6, epidermal growth factor and transforming growth factor-α and -β.

To date VEGF and the VEGF family members have been reported to bind to one or more of three transmembrane receptor tyrosine kinases (Mustonen et al. *J. Cell Biol.*, 1995, 129, 895), VEGF receptor-1 (also known as flt-1 (fms-like tyrosine kinase-1)); VEGFR-2 (also known as kinase insert domain containing receptor (KDR), the murine analogue of KDR being known as fetal liver kinase-1 (flk-1)); and VEGFR-3 (also known as flt4). KDR and fit-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependent tyrosine phosphorylation in intact cells, whereas flt-1 displays a weaker response. Thus, binding to KDR is a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. Regulation of the VEGF-mediated signal transduction cascade will therefore provide a useful mode for control of abnormal angiogenesis and/or hyperpermeability processes.

Angiogenesis is regarded as an absolute prerequisite for growth of tumors beyond about 1–2 mm. Oxygen and nutrients may be supplied to cells in tumors smaller than this limit through diffusion. However, every tumor is dependent on angiogenesis for continued growth after it has reached a certain size. Tumorigenic cells within hypoxic regions of tumors respond by stimulation of VEGF production, which triggers activation of quiescent endothelial cells to stimulate new blood vessel formation. (Shweiki et al. *Proc. Natl. Acad. Sci.*, 1995, 92, 768). In addition, VEGF production in tumor regions where there is no angiogenesis may proceed through the ras signal transduction pathway (Grugel et al. *J. Biol. Chem.*, 1995, 270, 25915; Rak et al. *Cancer Res.* 1995, 55, 4575). In situ hybridization studies have demonstrated VEGF mRNA is strongly upregulated in a wide variety of human tumors, including lung (Mattern et al. *Br. J. Cancer* 1996, 73, 931), thyroid (Viglietto et al. *Oncogene* 1995, 11, 1569), breast (Brown et al. *Human Pathol.* 1995, 26, 86), gastrointestional tract (Brown et al. *Cancer Res.* 1993, 53, 4727; Suzuki et al. *Cancer Res.* 1996, 56, 3004), kidney and bladder (Brown et al. *Am. J. Pathol.* 1993, 1431, 1255), ovary (Olson et al. *Cancer Res.* 1994, 54, 1255), and cervical (Guidi et al. *J. Nat'l Cancer Inst.* 1995, 87, 12137) carcinomas, as well as angiosacroma (Hashimoto et al. *Lab. Invest.* 1995, 73, 859) and several intracranial tumors (Plate et al. *Nature* 1992, 359, 845; Phillips et al. *Int. J. Oncol.* 1993, 2, 913; Berkman et al. *J. Clin. Invest.*, 1993, 91, 153). Neutralizing monoclonal antibodies to KDR have been shown to be efficacious in blocking tumor angiogenesis (Kim et al. Nature 1993, 362, 841; Rockwell et al. *Mol. Cell Differ.* 1995, 3, 315).

Overexpression of VEGF, for example under conditions of extreme hypoxia, can lead to intraocular angiogenesis, resulting in hyperproliferation of blood vessels, leading eventually to blindness. Such a cascade of events has been observed for a number of retinopathies, including diabetic retinopathy, ischemic retinal-vein occlusion, retinopathy of prematurity (Aiello et al. *New Engl. J. Med.* 1994, 331, 1480; Peer et al. *Lab. Invest.* 1995, 72, 638), and age-related macular degeneration (AMD; see, Lopez et al. *Invest. Opthalmol. Vis. Sci.* 1996, 37,855).

In rheumatoid arthritis (RA), the in-growth of vascular pannus may be mediated by production of angiogenic factors. Levels of immunoreactive VEGF are high in the synovial fluid of RA patients, while VEGF levels were low in the synovial fluid of patients with other forms of arthritis of with degenerative joint disease (Koch et al. *J. Immunol.* 1994, 152, 4149). The angiogenesis inhibitor AGM-170 has been shown to prevent neovascularization of the joint in the rat collagen arthritis model (Peacock et al. *J. Exper. Med.* 1992, 175, 1135).

Increased VEGF expression has also been shown in psoriatic skin, as well as bullous disorders associated with subepidermal blister formation, such as bullous pemphigoid, erythema multiforme, and dermatitis herpetiformis (Brown et al. *J. Invest. Dermatol.* 1995, 104, 744).

Because inhibition of KDR signal transduction leads to inhibition of VEGF-mediated angiogenesis and permeabilization, KDR inhibitors will be useful in treatment of diseases characterized by abnormal angiogenesis and/or hyperpermeability processes, including the above listed diseases.

Examples of phthalazines and other fused pyridazines that are similar in structure a to those of the present application are disclosed in the following patents or patent applications: WO 9835958 (Novartis), U.S. Pat. No. 5,849,741, U.S. Pat. No. 3,753,988, U.S. Pat. No. 3,478,028 and JP 03106875. Other literature references to phthalazines are El-Feky, S. A., Bayoumy, B. E., and Abd El-Sami, Z. K., Egypt J. Chem. (1991), Volume Date 1990, 33(2), 189–197; Duhault, J., Gonnard, P., and Fenard, S., Bull. Soc. Chim. Biol., (1967), 49 (2), 177–190; and Holava, H. M. and Jr, Partyka, R. A., J. Med. Chem., (1969), 12, 555–556. The compounds of the present invention are distinct from those described in each of the above references, and only the Novartis publication describes such compounds as inhibitors of angiogenesis.

As explained above, compounds which inhibit angiogenesis have applicability in treatment of a variety of medical conditions, and are therefore desirable. Such materials are the subject of the present application.

SUMMARY

In its broadest aspect, the present invention relates to the sum of three sets of chemical compounds, or pharmaceutically acceptable salts or prodrugs thereof, with each set overlapping the others in scope. The generalized structural formula for the compounds in each of the three sets of compounds is the same, but it should be noted that the definitions of the several groups comprising the general structure in each set differ somewhat. Thus, the defined sets of chemical compounds differ from each other, but overlap in their scopes.

The first set of compounds have the generalized structural formula

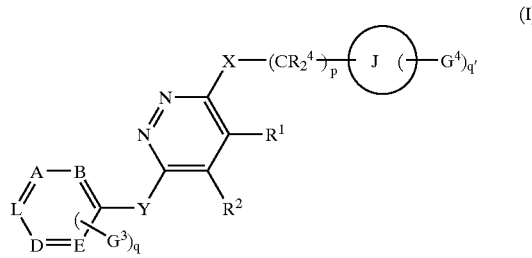

(I)

wherein
$R^1$ and $R^2$:

i) independently represent H or lower alkyl;
ii) together form a bridge of structure

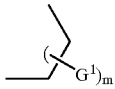

wherein binding is achieved via the terminal carbon atoms;
iii) together form a bridge of structure

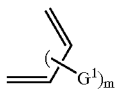

wherein binding is achieved via the terminal carbon atoms; or
iv) together form a bridge of structure

wherein one or two ring members $T^1$ are N and the others are CH, and binding is achieved via the terminal atoms.

In the above bridge substructures, the subscript m is 0 or an integer 1–4, indicating that the resultant fused rings may optionally bear up to four substituents $G^1$.

$G^1$ is a substituent independently selected from the group consisting of: —N($R^6$)$_2$; —N$R^3$COR$^6$; halogen; alkyl; cycloalkyl; lower alkenyl; lower cycloalkenyl; halogen-substituted alkyl; amino-substituted alkyl; N-lower alkylamino-substituted alkyl; N,N-di-lower alkylamino-substituted alkyl; N-lower alkanoylamino-substituted alkyl; hydroxy-substituted alkyl; cyano-substituted alkyl; carboxy-substituted alkyl; lower alkoxycarbonyl-substituted alkyl; phenyl lower alkoxycarbonyl-substituted alkyl; halogen-substituted alkylamino; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; cyano-substituted alkylamino; carboxy-substituted alkylamino; lower alkoxycarbonyl-substituted alkylamino; phenyl-lower alkoxycarbonyl-substituted alkylamino; —OR$^6$; —SR$^6$; —S(O)R$^6$; —S(O)R$^6$; halogenated lower alkoxy; halogenated lower alkylthio; halogenated lower alkylsulfonyl; —OCOR$^6$; —COR$^6$; —CO$_2$R$^6$; —CON(R$^6$)$_2$; —CH$_2$OR$^3$; —NO$_2$; —CN; amidino; guanidino; sulfo; —B(OH)2; optionally substituted aryl; optionally substituted heteroaryl; optionally substituted saturated heterocyclyl; optionally substituted partially unsaturated heterocyclyl; —OCO$_2$R$^3$; optionally substituted heteroarylalkyl; optionally substituted heteroaryloxy; —S(O)$_p$ (optionally substituted heteroaryl); optionally substituted heteroarylalkyloxy; —S(O)$_p$(optionally substituted heteroarylalkyl); —CHO; —OCON(R$^6$)$_2$; —NR$^3$CO$_2$R$^6$; and —NR$^3$CON(R$^2$)$_2$.

The group $R^3$ is H or lower alkyl. $R^6$ is independently selected from the group consisting of H; alkyl; optionally substituted aryl; and optionally substituted aryl lower alkyl.

In generalized structural formula (I), $R^4$ is H, halogen, or lower alkyl; the subscript p is 0, 1, or 2; and X is selected from the group consisting of O, S, and NH.

The linking moiety Y is selected from the group consisting of: —(CR$^4_2$)$_a$—S(O)$_p$—(5-membered heteroaryl)—(CR$^4_2$)$_a$—; —(CR$^4_2$)$_n$—C(G$^2$)(R$^4$)—(CR$^4_2$)$_s$—; —O—CH$_2$—; —S(O)—; —S(O)$_2$; —SCH$_2$—; —S(O)CH$_2$—; —S(O)$_2$CH$_2$—; —CH$_2$S(O)—; and —CH$_2$S(O)$_2$—. In the first two members of the above list of possible Y groups, the subscripts n and s are each independently 0 or an integer of 1–2. The substituent $G^2$ is selected from the group consisting of —CN; —CO$_2$R$^3$; —CON(R$^6$)$_2$; and CH$_2$N(R$^6$)$_2$.

In the ring shown at the left in generalized structural formula (I), A and D independently represent N or CH; B and E independently represent N or CH; and L represents N or CH; with the provisos that a) the total number of N atoms in the ring containing A, B, D, E, and L is 1, 2, or 3; and b) when L represents CH, at least one of A and D is an N atom. The subscript q, which indicates the number of possible substituents $G^3$ on the ring, is 0, 1, or 2. Substituent moieties $G^3$ are selected from the group consisting of lower alkyl; —NR$^3$COR$^6$; carboxy-substituted alkyl; lower alkoxycarbonyl-substituted alkyl; —OR$^6$; —SR$^6$; —S(O)R$^6$; —S(O)$_2$R$^6$; —OCOR$^6$; —COR$^6$; —CO$_2$R$^6$; —CH$_2$OR$^3$; —CON(R$^6$)$_2$; —S(O)$_2$N(R$^6$)$_2$; —NO$_2$; —CN; optionally substituted aryl; optionally substituted heteroaryl; optionally substituted saturated heterocyclyl; optionally substituted partially unsaturated heterocyclyl; optionally substituted heteroarylalkyl; optionally substituted heteroaryloxy; —S(O)$_p$(optionally substituted heteroaryl); optionally substituted heteroarylalkyloxy; —S(O)$_p$(optionally substituted heteroarylalkyl); —OCON(R$^6$)$_2$—NR$^3$CO$_2$R$^6$; and —NR$^3$CON(R$^6$)$_2$.

J is a ring selected from the group consisting of aryl; pyridyl; and cycloalkyl. The subscript q' represents the number of substituents G$^4$ on ring J and is 0, 1, 2, 3, 4, or 5.

The possible substituents G$^4$ on ring J are selected from the group consisting of —N(R$^6$)$_2$; —NR$^3$COR$^6$; halogen; alkyl; cycloalkyl; lower alkenyl; lower cycloalkenyl; halogen-substituted alkyl; amino-substituted alkyl; N-lower alkylamino-substituted alkyl; N,N-di-lower alkylamino-substituted alkyl; N-lower alkanoylamino-substituted alkyl; hydroxy-substituted alkyl; cyano-substituted alkyl; carboxy-substituted alkyl; lower alkoxycarbonyl-substituted alkyl; phenyl lower alkoxycarbonyl-substituted alkyl; halogen-substituted alkylamino; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; cyano-substituted alkylamino; carboxy-substituted alkylamino; lower alkoxycarbonyl-substituted alkylamino; phenyl-lower alkoxycarbonyl-substituted alkylamino; —OR$^6$; —SR$^6$; —S(O)R$^6$; —S(O)R$^6$; halogenated lower alkoxy; halogenated lower alkylthio; halogenated lower alkylsulfonyl; —OCOR$^6$; —COR$^6$; —CON(R$^6$)$_2$; —CH$_2$OR$^3$; —NO$_2$; —CN; amidino; guanidino; sulfo; —B(OH)$_2$; optionally substituted aryl; optionally substituted heteroaryl; optionally substituted saturated heterocyclyl; optionally substituted partially unsaturated heterocyclyl; —OCO$_2$R$^3$; optionally substituted heteroarylalkyl; optionally substituted heteroaryloxy; —S(O)$_p$(optionally substituted heteroaryl); optionally substituted heteroarylalkyloxy; —S(O)$_p$(optionally substituted heteroarylalkyl); —CHO; —OCON(R$^6$)$_2$—NR$^3$CO$_2$R$^6$; —NR$^3$CON(R$^6$)$_2$; as well as fused ring-forming bridges attached to and connecting adjacent positions of ring J, said bridges having the structures:

a)

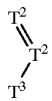

wherein each T$^2$ independently represents N, CH, or CG$^4$; T$^3$ represents S, O, CR$^4$G$^4$, C(R$^4$)$_2$, or NR$^3$; and binding to ring J is achieved via terminal atoms T$^2$ and T$^3$;

b)

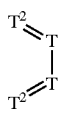

wherein each T$^2$ independently represents N, CH, or CG$^4$; with the proviso that a maximum of two bridge atoms T$^2$ may be N; and binding to ring J is achieved via terminal atoms T$^2$; and c)

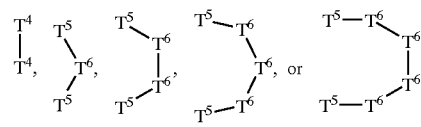

wherein each T$^4$, T$^5$, and T$^6$ independently represents O, S, CR$^4$G$^4$, C(R$^4$)$_2$, or NR$^3$; and binding to ring J is achieved via terminal atoms T$^4$ or T$^5$; with the provisos that:

i) when one T$^4$ is O, S, or NR$^3$, the other T$^4$ is CR$^4$G$^4$ or C(R$^4$)$_2$;

ii) a bridge comprising T$^5$ and T$^6$ atoms may contain a maximum of two heteroatoms O, S, or N; and iii) in a bridge comprising T$^5$ and T$^6$ atoms, when one T$^5$ group and one T$^6$ group are O atoms, or two T$^6$ groups are O atoms, said O atoms are separated by at least one carbon atom.

Additional provisos are that, 1) in G$^1$, G$^2$, G$^3$, and G$^4$, when two groups R$^6$ are each alkyl and located on the same N atom they may be linked by a bond, an O, an S, or NR$^3$ to form a N-containing heterocycle of 5–7 ring atoms; and 2) when an aryl, heteroaryl, or heterocyclyl ring is optionally substituted, that ring may bear up to 5 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —CO$_2$R$^3$, —CHO, —CH$_2$OR$^3$, —OCO$_2$R$^3$, —CON(R$^6$)$_2$, —OCO N(R$^6$)$_2$, —NR$^3$CON(R$^6$)$_2$, nitro, amidino, guanidino, mercapto, sulfo, and cyano.

The second set of compounds have the generalized structural formula

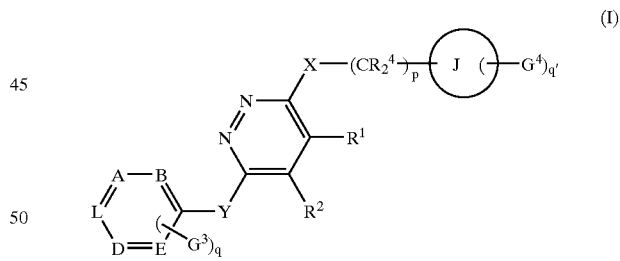

(I)

wherein R$^1$ and R$^2$:

i) independently represent H or lower alkyl;

ii) together form a bridge of structure

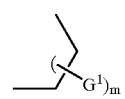

wherein binding is achieved via the terminal carbon atoms;

iii) together form a bridge of structure

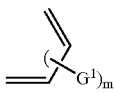

wherein binding is achieved via the terminal carbon atoms; or iv) together form a bridge of structure

wherein one or two ring members $T^1$ are N and the others are CH, and binding is achieved via the terminal atoms.

In the above bridge substructures, the subscript m is 0 or an integer 1–4; indicating that the resultant fused rings may optionally bear up to four substituents $G^1$.

$G^1$ is a substituent independently selected from the group consisting of: —N($R^6$)$_2$—N$R^3$CO$R^6$; halogen; alkyl; cycloalkyl; lower alkenyl; lower cycloalkenyl; halogen-substituted alkyl; amino-substituted alkyl; N-lower alkylamino-substituted alkyl; N,N-di-lower alkylamino-substituted alkyl; N-lower alkanoylamino-substituted alkyl; hydroxy-substituted alkyl; cyano-substituted alkyl; carboxy-substituted alkyl; lower alkoxycarbonyl-substituted alkyl; phenyl lower alkoxycarbonyl-substituted alkyl; halogen-substituted alkylamino; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; cyano-substituted alkylamino; carboxy-substituted alkylamino; lower alkoxycarbonyl-substituted alkylamino; phenyl-lower alkoxycarbonyl-substituted alkylamino; —O$R^6$; —S$R^6$; —S(O)$R^6$; —S(O)$_2R^6$; halogenated lower alkoxy; halogenated lower alkylthio; halogenated lower alkylsulfonyl; —OCO$R^6$; —CO$R^6$; —CO$_2R^6$; —CON($R^6$)$_2$; —CH$_2$O$R^3$; —NO$_2$; —CN; amidino; guanidino; sulfo; —B(OH)2; optionally substituted aryl; optionally substituted heteroaryl; optionally substituted saturated heterocyclyl; optionally substituted partially unsaturated heterocyclyl; —OCO$_2R^3$; optionally substituted heteroarylalkyl; optionally substituted heteroaryloxy; —S(O)$_p$(optionally substituted heteroaryl); optionally substituted heteroarylalkyloxy; —S(O)$_p$(optionally substituted heteroarylalkyl); —CHO; —OCON($R^6$)$_2$; —N$R^3$CO$_2R^6$; and —N$R^3$CON($R^6$)$_2$.

The group $R^3$ is H or lower alkyl. $R^6$ is independently selected from the group consisting of H; alkyl; optionally substituted aryl; and optionally substituted aryl lower alkyl.

In generalized structural formula (I), $R^4$ is H, halogen, or lower alkyl; the subscript p is 0, 1, or 2; and X is selected from the group consisting of O, S, and NH.

The linking moiety Y is selected from the group consisting of: lower alkylene, optionally substituted by OH or OAcyl; —CH$_2$O—; —CH$_2$S—; —CH$_2$NH—; —O—; —S—; —NH—; —(C$R_2^4$)$_n$—S(O)$_p$—(5-membered heteroaryl)—(C$R_2^4$)$_s$; —(C$R_2^4$)$_n$—C(G$^2$)($R^4$)—(C$R_2^4$)$_s$—; —O—CH$_2$—; —S(O)—; —S(O)$_2$—; —SCH$_2$—; —S(O) CH$_2$—; —S(O)$_2$CH$_2$—; —CH$_2$S(O)—; and —CH$_2$S(O)$_2$—. In the eighth and ninth members of the above list of possible Y groups, the subscripts n and s are each independently 0 or an integer of 1–2. The substituent $G^2$ is selected from the group consisting of —CN; —CO$_2R^3$; —CON($R^6$)$_2$; and —CH$_2$N($R^6$)$_2$.

In the ring shown at the left in generalized structural formula (I), A and D independently represent N or CH; B and E independently represent N or CH; and L represents N or CH; with the provisos that a) the total number of N atoms in the ring containing A, B, D, E, and L is 1, 2, or 3; and b) when L represents CH, at least one of A and D is an N atom. The subscript q, which indicates the number of possible substituents on the ring, is 0, 1, or 2. Substituent moieties $G^3$ are selected from the group consisting of —N$R^3$CO$R^6$; carboxy-substituted alkyl; lower alkoxycarbonyl-substituted alkyl; —O$R^6$; —S$R^6$; —S(O)$R^6$; —S(O)$_2R^6$; —OCO$R^6$; —CO$R^6$; —CO$_2R^6$; —CH$_2$O$R^3$; —CON($R^6$)$_2$; —S(O)$_2$N($R^6$)$_2$; —NO$_2$; —CN; optionally substituted aryl; optionally substituted heteroaryl; optionally substituted saturated heterocyclyl; optionally substituted partially unsaturated heterocyclyl; optionally substituted heteroarylalkyl; optionally substituted heteroaryloxy; —S(O)$_p$(optionally substituted heteroaryl); optionally substituted heteroarylalkyloxy; —S(O)$_p$(optionally substituted heteroarylalkyl); —OCON($R^6$)$_2$; —N$R^3$CO$_2R^6$; and —N$R^3$CON($R^6$)$_2$.

J is a ring selected from the group consisting of aryl; pyridyl; and cycloalkyl. The subscript q' represents the number of substituents $G^4$ on ring J and is 0, 1, 2, 3, 4, or 5.

The possible substituents $G^4$ on ring J are selected from the group consisting of —N($R^6$)$_2$; —N$R^3$CO$R^6$; halogen; alkyl; cycloalkyl; lower alkenyl; lower cycloalkenyl; halogen-substituted alkyl; amino-substituted alkyl; N-lower alkylamino-substituted alkyl; N,N-di-lower alkylamino-substituted alkyl; N-lower alkanoylamino-substituted alkyl; hydroxy-substituted alkyl; cyano-substituted alkyl; carboxy-substituted alkyl; lower alkoxycarbonyl-substituted alkyl; phenyl lower alkoxycarbonyl-substituted alkyl; halogen-substituted alkylamino; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; cyano-substituted alkylamino; carboxy-substituted alkylamino; lower alkoxycarbonyl-substituted alkylamino; phenyl-lower alkoxycarbonyl-substituted alkylamino; —O$R^6$; —S$R^6$; —S(O)$R^6$; —S(O)$_2R^6$; halogenated lower alkoxy; halogenated lower alkylthio; halogenated lower alkylsulfonyl; —OCO$R^6$; —CO$R^6$; —CO$_2R^6$; —CON($R^6$)$_2$; —CH$_2$O$R^3$; —NO$_2$; —CN; amidino; guanidino; sulfo; —B(OH)2; optionally substituted aryl; optionally substituted heteroaryl; optionally substituted saturated heterocyclyl; optionally substituted partially unsaturated heterocyclyl; —OCO$_2R^3$; optionally substituted heteroarylalkyl; optionally substituted heteroaryloxy; —S(O)$_p$ (optionally substituted heteroaryl); optionally substituted heteroarylalkyloxy; —S(O)$_p$(optionally substituted heteroarylalkyl); —CHO; —OCON($R^6$)$_2$—N$R^3$CO$_2R^6$; —N$R^3$CON($R^6$)$_2$; as well as fused ring-forming bridges attached to and connecting adjacent positions of ring J, said bridges having the structures:

a)

wherein each $T^2$ independently represents N, CH, or CG$^4$; $T^3$ represents S, O, C$R^4$G$^4$, C($R^4$)$_2$, or N$R^3$; and binding to ring J is achieved via terminal atoms $T^2$ and $T^3$;

b)

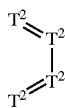

wherein each $T^2$ independently represents N, CH, or $CG^4$; with the proviso that a maximum of two bridge atoms $T^2$ may be N; and binding to ring J is achieved via terminal atoms $T^2$; and c)

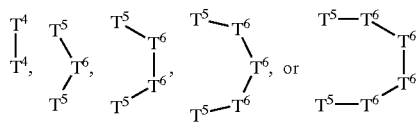

wherein each $T^4$, $T^5$, and $T^6$ independently represents O, S, $CR^4G^4$, $C(R^4)_2$, or $NR^3$; and binding to ring J is achieved via terminal atoms $T^4$ or $T^5$; with the provisos that:

i) when one $T^4$ is O, S, or $NR^3$, the other $T^4$ is $CR^4G^4$ or $C(R^4)_2$;

ii) a bridge comprising $T^5$ and $T^6$ atoms may contain a maximum of two heteroatoms O, S, or N; and iii) in a bridge comprising $T^5$ and $T^6$ atoms, when one $T^5$ group and one $T^6$ group are O atoms, or two $T^6$ groups are O atoms, said O atoms are separated by at least one carbon atom.

Additional provisos are that, 1) in $G^1$, $G^2$, $G^3$, and $G^4$, when two groups $R^6$ are each alkyl and located on the same N atom they may be linked by a bond, an O, an S, or $NR^3$ to form a N-containing heterocycle of 5–7 ring atoms; and 2) when an aryl, heteroaryl, or heterocyclyl ring is optionally substituted, that ring may bear up to 5 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —$CO_2R^3$, —CHO, —$CH_2OR^3$, —$OCO^2R^3$, —$CON(R^6)_2$, —OCO $N(R^6)_2$, —$NR^3CON(R^6)_2$, nitro, amidino, guanidino, mercapto, sulfo, and cyano.

The third set of compounds have the generalized structural formula

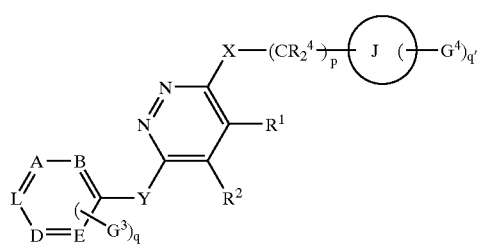 (I)

wherein $R^1$ and $R^2$:

i) independently represent H or lower alkyl;

ii) together form a bridge of structure

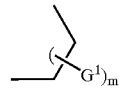

wherein binding is achieved via the terminal carbon atoms;

iii) together form a bridge of structure

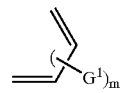

wherein binding is achieved via the terminal carbon atoms; or iv) together form a bridge of structure

wherein one or two ring members $T^1$ are N and the others are CH, and binding is achieved via the terminal atoms.

In the above bridge substructures, the subscript m is 0 or an integer 1–4; indicating that the resultant fused rings may optionally bear up to four substituents $G^1$.

$G^1$ is a substituent independently selected from the group consisting of: —$N(R^6)_2$; —$NR^3COR^6$; halogen; alkyl; cycloalkyl; lower alkenyl; lower cycloalkenyl; halogen-substituted alkyl; amino-substituted alkyl; N-lower alkylamino-substituted alkyl; N,N-di-lower alkylamino-substituted alkyl; N-lower alkanoylamino-substituted alkyl; hydroxy-substituted alkyl; cyano-substituted alkyl; carboxy-substituted alkyl; lower alkoxycarbonyl-substituted alkyl; phenyl lower alkoxycarbonyl-substituted alkyl; halogen-substituted alkylamino; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; cyano-substituted alkylamino; carboxy-substituted alkylamino; lower alkoxycarbonyl-substituted alkylamino; phenyl-lower alkoxycarbonyl-substituted alkylamino; —$OR^6$; —$SR^6$; —$S(O)R^6$; —$S(O)_2R^6$; halogenated lower alkoxy; halogenated lower alkylthio; halogenated lower alkylsulfonyl; —$OCOR^6$; —$COR^6$; —$CO_2R^6$; —$CON(R^6)_2$; —$CH_2OR^3$; —$NO_2$; —CN; amidino; guanidino; sulfo; —$B(OH)2$; optionally substituted aryl; optionally substituted heteroaryl; optionally substituted saturated heterocyclyl; optionally substituted partially unsaturated heterocyclyl; —$OCO_2R^3$; optionally substituted heteroarylalkyl; optionally substituted heteroaryloxy; —$S(O)_p$ (optionally substituted heteroaryl); optionally substituted heteroarylalkyloxy; —$S(O)_p$(optionally substituted heteroarylalkyl); —CHO; —$OCON(R^6)_2$—$NR^3CO_2R^6$; and —$NR^3CON(R^6)_2$.

The group $R^3$ is H or lower alkyl. $R^6$ is independently selected from the group consisting of H; alkyl; optionally substituted aryl; optionally substituted aryl lower alkyl.

In generalized structural formula (I), $R^4$ is H, halogen, or lower alkyl; the subscript p is 0, 1, or 2; and X is selected from the group consisting of O, S, and NH.

The linking moiety Y is selected from the group consisting of lower alkylene, optionally substituted by OH or OAcyl; —CH$_2$O—; —CH$_2$—S—; —CH$_2$—NH—; —O—; —S—; —NH—; —(CR$_2^4$)$_n$—S(O)$_p$—(5-membered heteroaryl)—(CR$_2^4$)$_s$—; —(CR$_2^4$)$_n$—C(G$^2$)(R$^4$)—(CR$_2^4$)$_s$—; —O—CH$_2$—; —S(O)—; —S(O)$_2$—; —SCH$_2$—; —S(O)CH$_2$—; —S(O)$_2$CH$_2$—; —CH$_2$S(O)—; and —CH$_2$S(O)$_2$—.

In the eighth and ninth members of the above list of possible Y groups, the subscripts n and s are each independently 0 or an integer of 1–2. The substituent G$^2$ is selected from the group consisting of —CN; —CO$_2$R$^3$; —CON(R$^6$)$_2$; and —CH$_2$N(R$^6$)$_2$.

In the ring shown at the left in generalized structural formula (I), A and D independently represent N or CH; B and E independently represent N or CH; and L represents N or CH; with the provisos that a) the total number of N atoms in the ring containing A, B, D, E, and L is 1, 2, or 3; and b) when L represents CH, at least one of A and D is an N atom. The subscript q, which indicates the number of possible substituents G$^3$ on the ring, is 0, 1, or 2. Substituent moieties G$^3$ are selected from the group consisting of lower alkyl; —NR$^3$COR$^6$; carboxy-substituted alkyl; lower alkoxycarbonyl-substituted alkyl; —OR$^6$; —SR$^6$; —S(O)R$^6$; —S(O)$_2$R$^6$; —OCOR$^6$; —COR$^6$; —CO$_2$R$^6$; —CH$_2$OR$^3$; —CON(R$^6$)$_2$; —S(O)$_2$N(R$^6$)$_2$; —NO$_2$; —CN; optionally substituted aryl; optionally substituted heteroaryl; optionally substituted saturated heterocyclyl; optionally substituted partially unsaturated heterocyclyl; optionally substituted heteroarylalkyl; optionally substituted heteroaryloxy; —S(O)$_p$(optionally substituted heteroaryl); optionally substituted heteroarylalkyloxy; —S(O)$_p$(optionally substituted heteroarylalkyl); —OCON(R$^6$)$_2$—NR$^3$CO$_2$R$^6$; and —NR$^3$CON(R$^6$)$_2$.

J is a ring selected from the group consisting of aryl; pyridyl; and cycloalkyl. The subscript q' represents the number of substituents G$^4$ on ring J and is 0, 1, 2, 3, 4, or 5.

The possible substituents G$^4$ on ring J are selected from the group consisting of optionally substituted heteroarylalkyl; optionally substituted heteroaryloxy; —S(O)$_p$(optionally substituted heteroaryl); optionally substituted heteroarylalkyloxy; —S(O)$_p$(optionally substituted heteroarylalkyl); —CHO; —OCON(R$^6$)$_2$; —NR$^3$CO$_2$R$^6$—NR$^3$CON(R$^6$)$_2$; as well as fused ring-forming bridges attached to and connecting adjacent positions of ring J, said bridges having the structures:

a)

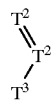

w wherein each T$^2$ independently represents N, CH, or CG$^4$; T$^3$ represents S, O, CR$^4$G$^4$, C(R$^4$)$_2$, or NR$^3$; and binding to ring J is achieved via terminal atoms T$^2$ and T$^3$;

b)

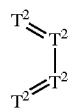

wherein each T$^2$ independently represents N, CH, or CG$^4$; with the proviso that a maximum of two bridge atoms T$^2$ may be N; and binding to ring J is achieved via terminal atoms T$^2$; and c)

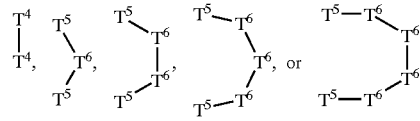

wherein each T$^4$, T$^5$, and T$^6$ independently represents O, S, CR$^4$G$^4$, C(R$^4$)$_2$, or NR$^3$; and binding to ring J is achieved via terminal atoms T$^4$ or T$^5$; with the provisos that:

i) when one T$^4$ is O, S, or NR$^3$, the other T$^4$ is CR$^4$G$^4$ or C(R$^4$)$_2$;

ii) a bridge comprising T$^5$ and T$^5$ atoms may contain a maximum of two heteroatoms O, S, or N; and iii) in a bridge comprising T$^5$ and T$^6$ atoms, when one T$^5$ is O, the other T$^5$ is S, CR$^4$G$^4$, C(R$^4$)$_2$ or NR$^3$;

iv) in a bridge comprising T$^5$ and T$^6$ atoms, when one T$^5$ group and one T$^6$ group are O atoms, or two T groups are O atoms, said O atoms are separated by at least one carbon atom.

Additional provisos are that, 1) in G$^1$, G$^2$, G$^3$, and G$^4$, when two groups R$^6$ are each alkyl and located on the same N atom they may be linked by a bond, an O, an S, or NR$^3$ to form a N-containing heterocycle of 5–7 ring atoms; and 2) when an aryl, heteroaryl, or heterocyclyl ring is optionally substituted, that ring may bear up to 5 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —CO$_2$R$^3$, —CHO, —CH$_2$OR$^3$, —OCO$_2$R$^3$, —CON(R$^6$)$_2$, —OCO N(R$^6$)$_2$, —NR$^3$CON(R$^6$)$_2$, nitro, amidino, guanidino, mercapto, sulfo, and cyano.

Pharmaceutically acceptable salts of these compounds as well as commonly used prodrugs of these compounds such as O-acyl derivatives of invention compounds which contain hydroxy groups are also within the scope of the invention.

The invention also relates to pharmaceutical compositions comprising one or more of the compounds of the invention, or their salts or prodrugs, in a pharmaceutically acceptable carrier.

The invention also relates to a method for using these materials to treat a mammal having a condition characterized by abnormal angiogenesis or hyperpermiability processes, comprising administering to the mammal an amount of a compound of the invention, or a salt or prodrug thereof, which is effective to treat the condition.

DETAILED DESCRIPTION

Definitions:

The prefix "lower" denotes a radical having up to and including a maximum of 7 atoms, especially up to and including a maximum of 5 carbon atoms, the radicals in question being either linear or branched with single or multiple branching.

"Alkyl" means a hydrocarbon radical having up to a maximum of 12 carbon atoms, which may be linear or branched with single or multiple branching. Alkyl is especially lower alkyl.

Where the plural form is used for compounds, salts, and the like, this is taken to mean also a single compound, salt, or the like.

Any asymmetric carbon atoms may be present in the (R)—, (S)— or (R,S)configuration, preferably in the (R)— or (S)—configuration. Substituents at a double bond or a ring may be present in cis-(=Z—) or trans (=E—) form. The compounds may thus be present as mixtures of isomers or as pure isomers, preferably as enantiomer-pure diastereomers and having pure cis- or trans-double bonds.

Lower alkylene Y may be branched or linear but is preferably linear, especially methylene (—CH$_2$), ethylene (—CH$_2$—CH$_2$), trimethylene (—CH$_2$—CH$_2$—CH$_2$) or tetramethylene (—CH$_2$—CH$_2$—CH$_2$—CH$_2$). When Y is lower alkylene, it is most preferably methylene.

"Aryl" means an aromatic radical having 6 to 14 carbon atoms, such as phenyl, naphthyl, fluorenyl or phenanthrenyl.

"Halogen" means fluorine, chlorine, bromine, or iodine but is especially fluorine, chlorine, or bromine.

"Pyridyl" means 1-, 2-, or 3-pyridyl but is especially 2- or 3-pyridyl.

"Cycloalkyl" is a saturated carbocycle that contains between 3 and 12 carbons but preferably 3 to 8 carbons.

"Cycloalkenyl" means a non-reactive and non-aromatic unsaturated carbocycle that contains between 3 and 12 carbons but preferably 3 to 8 carbons and up to three double bonds. It is well known to those skilled in the art that cycloalkenyl groups that differ from aromatics by lacking only one double bond such as cyclohaxadiene are not sufficiently non-reactive to be reasonable drug substances and therefor their use as substituents is not within the scope of this invention.

Cycloalkyl and cycloalkenyl groups may contain branch points such that they are substituted by alkyl or alkenyl groups. Examples of such branched cyclic groups are 3,4-dimethylcyclopentyl, 4-allylcyclohexyl or 3-ethylcyclopent-3-enyl.

Salts are especially the pharmaceutically acceptable salts of compounds of formula I such as, for example, acid addition salts, preferably with organic or inorganic acids, from compounds of formula I with a basic nitrogen atom. Suitable inorganic acids are, for example, halogen acids such as hydrochloric acid, sulfuric acid, or phosphoric acid. Suitable organic acids are, for example, carboxylic, phosphonic, sulfonic, or sulfamic acids, for example acetic acid, propionic acid, octanoic acid, decanoic acid, dodecanoic acid, glycolic acid, lactic acid, -hydroxybutyric acid, gluconic acid, glucosemonocarboxylic acid, fumaric acid, succinic acid, adipic acid, pimelic acid, suberic acid, azeiaic acid, malic acid, tartaric acid, citric acid, glucaric acid, galactaric acid, amino acids, such as glutamic acid, aspartic acid, N-methylglycine, acetytaminoacetic acid, N-acetylasparagine or N-acetylcysteine, pyruvic acid, acetoacetic acid, phosphoserine, 2- or 3-glycerophosphoric acid.

In the definition of Y, the diradical "-(5 member heteroaryl)-" denotes a 5-membered aromatic heterocycle containing 1–3 heteroatoms selected from O, S, and N, the number of N atoms being 0–3 and the number of O and S atoms each being 0–1 and connected to the sulfur from a carbon and to —(CR$_2^4$)$_s$— through a C or N atom. Examples of such diradicals include

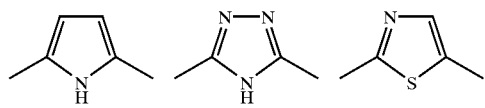

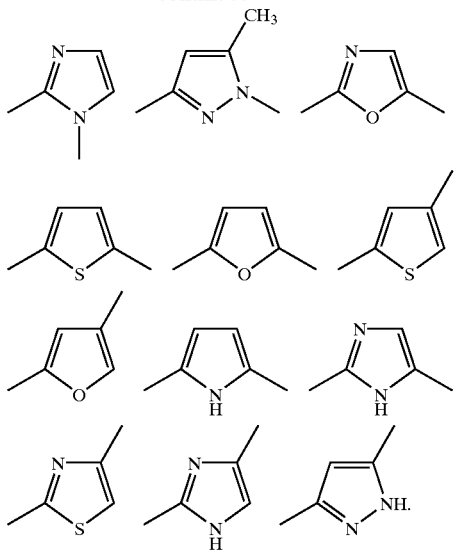

In the definitions of G$^1$, G$^2$, G$^3$ and G$^4$ the statement is made that when two groups R$^6$ are found on a single N, they can be combined into a heterocycle of 5–7 atoms. Examples of such heterocycles, including the N to which they are attached, are:

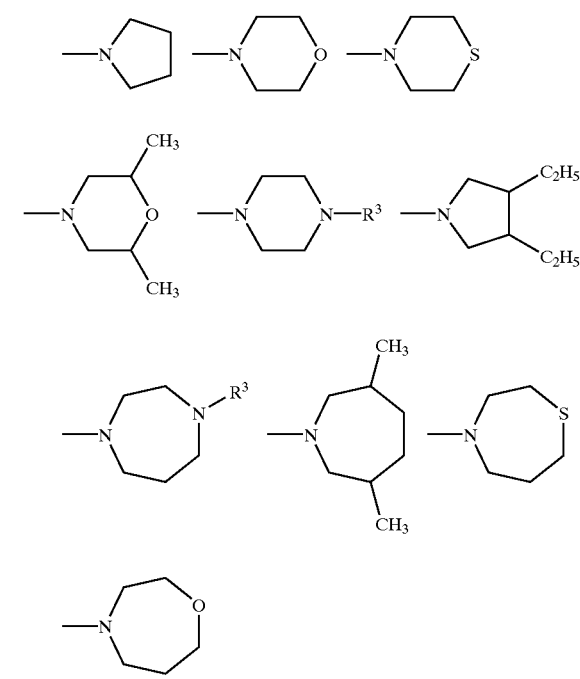

"Heterocyclyl" or "heterocycle" means a five- to seven-membered heterocyclic system with 1–3 heteroatoms selected from the group nitrogen, oxygen, and sulfur, which may be unsaturated or wholly or partly saturated, and is unsubstituted or substituted especially by lower alkyl, such as methyl, ethyl, 1-propyl, 2-propyl, or tert-butyl.

When an aryl, heteroaryl, or heterocyclyl ring is said to be optionally substituted, that ring may bear up to 5 substituents which are independently selected from the group consisting of amino, mono- or di-loweralkyl-substituted amino, lower alkanoylamino, halogeno, lower alkyl, halogenated lower alkyl such as trifluoromethyl, hydroxy, lower alkoxy, lower alkylthio, halogenated lower alkoxy such as trifluoromethoxy, halogenated lower alkylthio such as trifluoromethylthio, lower alkanoyloxy, —$CO_2R^3$, —CHO, —$CH_2OR^3$, —$OCO_2R^3$, —$CON(R^6)_2$, —OCO $N(R^6)_2$, —$NR^3CON(R^6)_2$, nitro, amidino, guanidino, mercapto, sulfo, and cyano.

In the ring attached to Y, the ring members A, B, D, E, and L may be N or CH, it being understood that the optional substituents $G^3$ are necessarily attached to carbon and not nitrogen, and that when a given carbon bears a substituent group $G^3$, that $G^3$ group is in place of the H atom the carbon would bear in the absence of the $G^3$ group.

Examples of ring J together with two adjacent $G^4$ moieties which taken together form a second fused ring are:

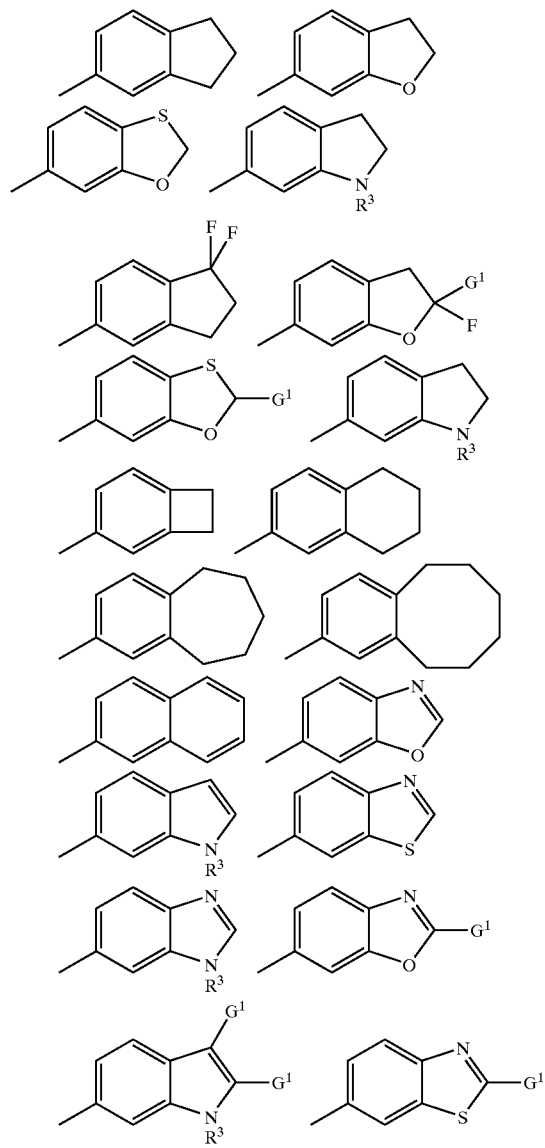

"Heteroaryl" means a monocyclic or fused bicyclic aromatic system with between 5 and 10 atoms in total of which 1–4 are heteroatoms selected from the group comprising nitrogen, oxygen, and sulfur and with the remainder being carbon. Heteroaryl is preferably a monocyclic system with 5 or 6 atoms in total, of which 1–3 are heteroatoms.

"Alkenyl" means an unsaturated radical having up to a maximum of 12 carbon atoms and may be linear or branched with single or multiple branching and containing up to 3 double bonds. Alkenyl is especially lower alkenyl with up to 2 double bonds.

"Alkanoyl" means alkylcarbonyl, and is especially lower alkylcarbonyl.

Halogenated lower alkyl, halogenated lower alkoxy and halogenated lower alkylthio are substituents in which the alkyl moieties are substituted either partially or in full with halogens, preferably with chlorine and/or fluorine and most preferably with fluorine. Examples of such substituents are trifluoromethyl, trifluoromethoxy, trifluoromethylthio, 1,1, 2,2-tetrafluoroethoxy, dichloromethyl, fluoromethyl and difluoromethyl.

When a substituent is named as a string of fragments such as "phenyl-lower alkoxycarbonyl-substituted alkylamino," it is understood that the point of attachment is to the final moiety of that string (in this case amino) and that the other fragments of that string are connected to each other in sequence as they are listed in the string. Thus an example of "phenyl-lower alkoxycarbonyl-substituted alkylamino" is:

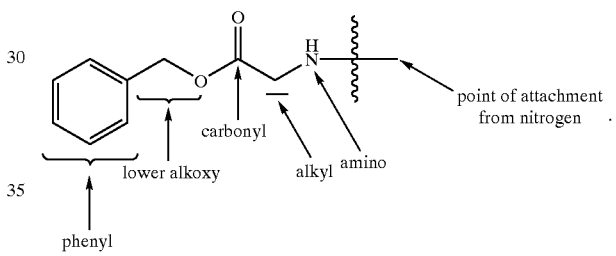

When a substituent is named as a string of fragments with a bond at the start (typically written as a dash) such as "—$S(O)_p$(optionally substituted heteroarylalkyl)", it is understood that the point of attachment is to the first atom of that string (in this case S or sulfur) and that the other fragments of that string are connected to each other in sequence as they are listed in the string. Thus an example of "—$S(O)_p$(optionally substituted heteroarylalkyl)" is:

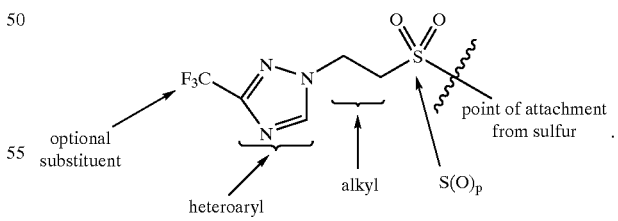

It is to be understood that the left-most moiety of each of the varients of the linker Y is connected to the ring containing A, B, D, E, and L and that the right-most moiety of the linker is connected to the pyridazine fragment of the generalized formulae. Thus examples of the use of the linker "—$CH_2$—O—" or of the linker "—O—$CH_2$—" are represented in the following invention compounds:

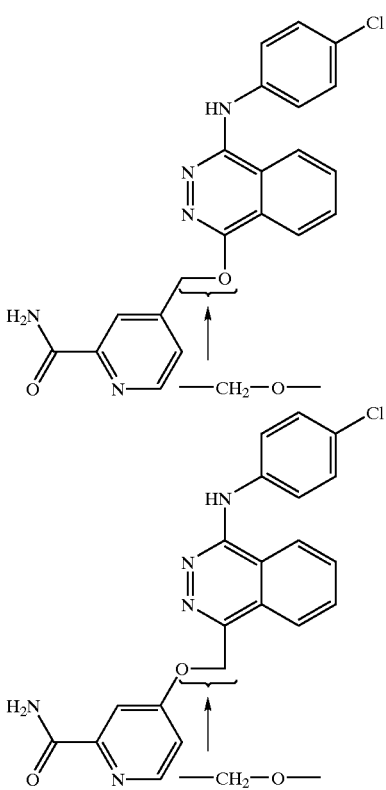

Preferred and most preferred groups: In generalized structural formula (I), the preferred groups are as follows. $R^1$ and $R^2$ preferably:

i) together form a bridge of structure

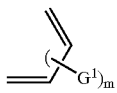

wherein binding is achieved via the terminal carbon atoms; or ii) together form a bridge of structure

wherein one of the ring members $T^1$ is N and the others are CH, and binding is achieved via the terminal atoms.

Most preferably, any group $G^1$ is located on a nonterminal atom of the bridge.

The subscript m is preferably 0 or an integer 1–2, and substituents $G^1$ are preferably selected from the group consisting of —$N(R^6)_2$; —$NR^3COR^6$; halogen; alkyl; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; carboxy-substituted alkylamino; lower alkoxycarbonyl-substituted alkylamino; —$OR^6$; —$SR^6$; —$S(O)R^6$; —$S(O)_2R^6$; halogenated lower alkoxy; halogenated lower alkylthio; halogenated lower alkylsulfonyl; —$OCOR^6$; —$COR^6$; —$CO_2R^6$; —$CON(R^6)_2$; —$NO_2$; —CN; optionally substituted heteroarylalkyl; optionally substituted heteroaryloxy; —$S(O)_p$ (optionally substituted heteroaryl); optionally substituted heteroarylalkyloxy; and —$S(O)_p$(optionally substituted heteroarylalkyl). Most preferably, $G^1$ is a substituent independently selected from the group consisting of —$N(R^6)_2$; —$NR^3COR^6$; halogen; —$OR^6$ wherein R6 represents lower alkyl; —$NO_2$; optionally substituted heteroaryloxy; and optionally substituted heteroarylalkyloxy.

When $R^6$ is an alkyl group, it is preferably lower alkyl. The group $R^4$ is preferably H; p is preferably 0 or 1; and X is preferably NH. In the linker group Y, the subscripts n and s are preferably 0, 1, or 2. Most preferably, Y is selected from the group consisting of lower alkylene, optionally substituted by OH; —$CH_2$—O—; —S—; —NH—; —$S(O)_p$—(5-membered heteroaryl)—; —C(CN)(H)—; —O—$CH_2$—; —S(O)—; and —$S(O)_2$—.

In the ring at the left side of the structure (I), B and E are preferably CH, and the total number of N atoms in this ring is preferably 1 or 2. Most preferably, A, B, D, and E are each CH and L is an N atom, making this ring a pyridine.

The substituents $G^3$ are preferably selected from the group consisting of lower alkyl; —$NR^3COR^6$; —$OR^6$; —$SR^6$; —$S(O)R^6$; —$S(O)_2R^6$; —$CO_2R^6$; —$CON(R^6)_2$; —$S(O)_2N(R^6)_2$; —CN; optionally substituted aryl; optionally substituted heteroaryl; optionally substituted heteroarylalkyl; optionally substituted heteroaryloxy; —$S(O)_p$ (optionally substituted heteroaryl); optionally substituted heteroarylalkyloxy; and —$S(O)_p$(optionally substituted heteroarylalkyl). Most preferably, $G^3$ is selected from the group consisting of lower alkyl; —$NR^3COR^6$; —$CO_2R^6$; —$CON(R^6)_2$; and —$S(O)_2N(R^6)_2$. Most preferably, the subscript q, which represents the number of substituents $G^3$, is 0 or 1.

Ring J is preferably a phenyl ring, and subscript q' representing the number of substituents $G^4$ on the phenyl ring, is preferably 0, 1, 2, or 3.

$G^4$ moieties are preferably selected from the group consisting of —$N(R^6)_2$—$NR^3COR^6$; halogen; alkyl; halogen-substituted alkyl; hydroxy-substituted alkyl; carboxy-substituted alkyl; lower alkoxycarbonyl-substituted alkyl; amino-substituted alkylamino; N-lower alkylamino-substituted alkylamino; N,N-di-lower alkylamino-substituted alkylamino; N-lower alkanoylamino-substituted alkylamino; hydroxy-substituted alkylamino; carboxy-substituted alkylamino; lower alkoxycarbonyl-substituted alkylamino; phenyl-lower alkoxycarbonyl-substituted alkylamino; —$OR^6$; —$SR^6$; —$S(O)R^6$; —$S(O)_2R^6$; halogenated lower alkoxy; halogenated lower alkylthio; halogenated lower alkylsulfonyl; —$OCOR^6$; —$COR^6$; —$CO_2R^6$; —$CON(R^6)_2$; —$CH_2OR^3$; —$NO_2$; —CN; optionally substituted heteroarylalkyl; optionally substituted heteroaryloxy; —$S(O)_p$(optionally substituted heteroaryl); optionally substituted heteroarylalkyloxy; —$S(O)_p$(optionally substituted heteroarylalkyl); as well as fused ring-forming bridges attached to and connecting adjacent positions of the phenyl ring, said bridges having the structures:

a)

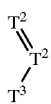

wherein each $T^2$ independently represents N, CH, or $CG^4$; $T^3$ represents S, O, $CHG^4$, $CH_2$, or $NR^3$; and binding to the phenyl ring is achieved via terminal atoms $T^2$ and $T^3$;

b)

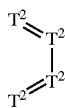

wherein each $T^2$ independently represents N, CH, or $CG^4$; with the proviso that a maximum of two bridge atoms $T^2$ may be N; and binding to the phenyl ring is achieved via terminal atoms $T^2$; and c)

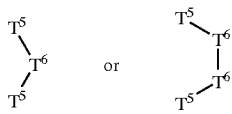

wherein each $T^5$ and $T^6$ independently represents O, S, $CHG^4$, $CH_2$, or $NR^3$; and binding to the phenyl ring is achieved via terminal atoms $T^5$.

Most preferably, in $G^1$, $G^2$, $G^3$, and $G^4$, when two groups $R^6$ are each alkyl and located on the same N atom they may be linked by a bond, an O, an S, or $NR^3$ to form a N-containing heterocycle of 5–6 ring atoms.

Preferably, when an aryl, heteroaryl, or heterocyclyl ring is optionally substituted, that ring may bear up to 2 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —$CO_2R^3$, —$CH_2OR^3$, —$OCO_2R^3$, —$CON(R^6)_2$, —OCO $N(R^6)_2$, —$NR^3CON(R^6)_2$, nitro, and cyano.

Most preferably, when an aryl, heteroaryl, or heterocyclyl ring is optionally substituted, that ring may bear up to 2 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, —$CO_2R^3$, —$CON(R^6)_2$, nitro, and cyano.

The method of the invention is intended to be employed for treatment of VEGF-mediated conditions in both humans and other mammals.

The compounds may be administered orally, dermally, parenterally, by injection, by inhalation or spray, or sublingually, rectally or vaginally in dosage unit formulations. The term 'administered by injection' includes intravenous, intraarticular, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired, other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations.

Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administered transdermally using methods known to those skilled in the art (see, for example: Chien; "Transdermal Controlled Systemic Medications"; Marcel Dekker, Inc.; 1987. Lipp et al. WO 94/04157 3 Mar. 1994). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsify agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures one or more materials selected from lower alcohols, lower ketones, lower carboxylic acid esters, polar ethers, lower hydrocarbons, halogenated hydrocarbons.

Suitable penetration enhancing materials for transdermal delivery systems are known to those skilled in the art, and include, for example, monohydroxy or polyhydroxy alcohols such as ethanol, propylene glycol or benzyl alcohol, saturated or unsaturated $C_8$–$C_{18}$ is fatty alcohols such as lauryl alcohol or cetyl alcohol, saturated or unsaturated $C_8$–$C_{18}$ is fatty acids such as stearic acid, saturated or unsaturated fatty esters with up to 24 carbons such as methyl, ethyl, propyl, isopropyl, n-butyl, sec-butyl isobutyl tert-butyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures one or more materials selected from monohydroxy or polyhydroxy alcohols, saturated or unsaturated $C_8$–$C_{18}$ fatty alcohols, saturated or unsaturated $C_8$–$C_{18}$ fatty acids, saturated or unsaturated fatty esters with up to 24 carbons, diesters of saturated or unsaturated dicarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrene-butadiene coploymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.1 to 200 mg administered between one to four times daily. The transdermal concentration will preferably be that required to maintain a daily dose of from 0.01 to 200 mg/Kg. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, but not limited to the activity of the specific compound employed, the age of the patient, the body weight of the patient the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, ie., the mode of treatment and the daily number of doses of a compound of Formula I or a pharmaceutically acceptable salt thereof given for a defined number of days, can be ascertained by those skilled in the art using conventional treatment tests.

GENERAL PREPARATIVE METHODS

The compounds of the invention may be prepared by use of known chemical reactions and procedures. Nevertheless, the following general preparative methods are presented to aid the reader in synthesizing the KDR inhibitors, with more detailed particular examples being presented below in the experimental section describing the working examples. Reference Compound A was prepared by the methods described in Novartis WO 9835958.

All variable groups of these methods are as described in the generic description if they are not specifically defined below. When a variable group or substituent with a given symbol (i.e. $R^3$, $R^4$, $R^6$, $G^1$, $G^2$, $G^3$, or $G^4$) is used more than once in a given structure, it is to be understood that each of these groups or substituents may be independently varied within the range of definitions for that symbol. As described above, the compounds of the invention contain ring units each of which may independently bear between 0 and 5 substituents $G^1$, $G^3$, or $G^4$ which are not defined as H. By contrast, it is to be noted that in the general method schemes below, the $G^1$, $G^3$, or $G^4$ substituents are used as if their definition includes H, to show where such $G^1$, $G^3$, or $G^4$ substituents may exist in the structures, and for ease in drawing. No change in the definition of $G^1$, $G^3$, or $G^4$ is intended by this non-standard usage, however. Thus, only for purposes of the general method schemes below, $G^1$, $G^3$, or $G^4$ may be H in addition to the moieties set forth in the definitions of $G^1$, $G^3$, or $G^4$. The ultimate compounds contain 0 to 5 non-hydrogen groups $G^1$, $G^3$, or $G^4$.

Within these general methods the variable M is equivalent to the moiety

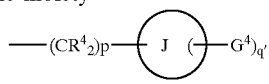

in which each variable group or substituent is allowed to independently vary within the limits defined earlier for that symbol.

Within these general methods the variable $Q^1$ is equivalent to the moiety

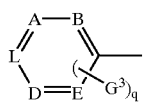

in which L is N and each other variable group or substituent is allowed to independently vary within the limits defined earlier for that symbol.

Within these general methods the variable $Q^2$ is equivalent to the moiety

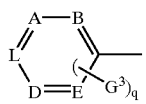

in which each variable group or substituent is allowed to independently vary within the limits defined earlier for that symbol.

It is recognized that compounds of the invention with each claimed optional functional group cannot be prepared with each of the below-listed methods. Within the scope of each method optional substituents are used which are stable to the reaction conditions, or the functional groups which may participate in the reactions are present in protected form where necessary, and the removal of such protective groups is completed at appropriate stages by methods well known to those skilled in the art.

General Method A—The compounds of formula I-D-1 in which $R^1$, $R^2$, $R^6$, M, X and Y are defined as above are conveniently prepared via a reaction sequence as shown in Method A. Thus, readily prepared substituted fused or unfused pyridazines (I-D) (as described in Novartis application WO 98 35958) are functionalized into substituted 2-aminocarbonyl pyridines of formula (I-D-1) by the use of formamides (II) in the presence of hydrogen peroxide and iron salts, according to a procedure described in the literature (Minisci et al., *Tetrahedron*, 1985, 41, 4157).

Method A

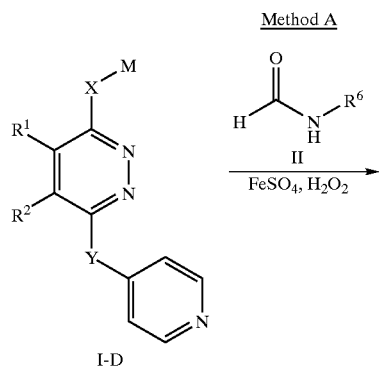

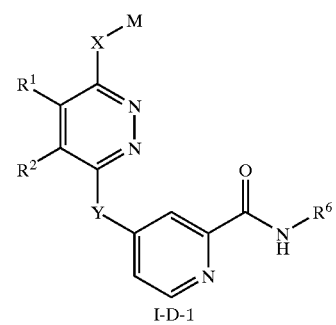

General Method B—The compounds of formula I-D-2 in which $R^1$, $R^2$, $R^6$, M, X and Y are defined as above and $R^3$ is lower alkyl are conveniently prepared via a reaction sequence as shown in Method B. Thus, readily prepared substituted fused or unfused pyridazines (I-D) (as described in Novartis application WO 98 35958) are functionalized into substituted 2-alkoxycarbonyl pyridines of formula (I-D-2) by the use of monoalkyloxalates (III) in the presence of $S_2O_8^{-2}$, acid and catalytic amounts of $AgNO_3$, according to a procedure described in the literature (Coppa, F. et al., *Tetrahedron Letters*, 1992, 33 (21), 3057). Compounds of formula I-D-2 in which $R^3$ is H are then formed by hydrolysis of the ester with a base such as sodium hydroxide in methanol/water. Compounds of formula I-D-3 in which the $R^6$ groups are independently defined as above, but especially including those compounds in which neither $R^6$ is H, are conveniently prepared from the acid (I-D-2, $R^3$=H) by treatment with amine IV in the presence of a coupling agent such as DCC (dicyclohexylcarbodiimide).

Method B

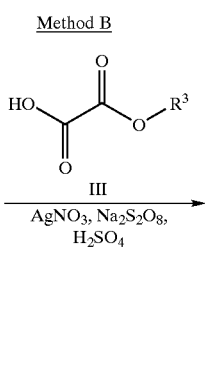

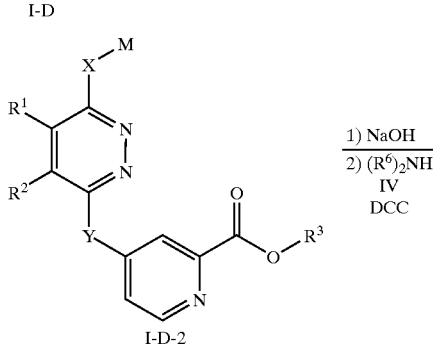

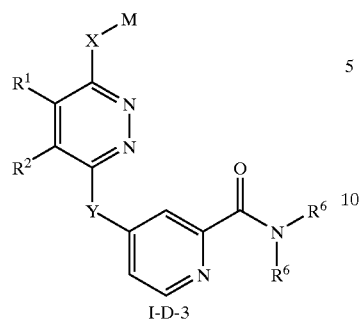

I-D-3

General Method C—The compounds of formula I-D4 in which M, X, $R^1$, $R^2$, and $Q^1$ are defined as above are conveniently prepared according to a reaction sequence as shown in Method C. Thus, a substituted keto acid having structure V, in which $R^1$ and $R^2$ together with the carbons to which they are attached are a fused optionally substituted phenyl or fused 6-member heterocycle is reacted with potassium permanganate according to the procedure of Hatam, N. A. R.; Whiting, D. A. *J. Chem Soc. C* 1969 1921. Compounds of formula VI in which $R^1$ and $R^2$ are lower alkyl are conveniently prepared according to procedures given in patent CH 482415 (Chem. Abstr. 120261u, 1970). The crude diacid of formula VI is subsequently treated with hydrazine to furnish pyridazinone VII (for specific reaction conditions see Vaughn, W. R.; Baird, S. L. *J. Am. Chem. Soc.* 1946 68 1314). Pyridazinone VII is treated with a chlorinating agent such as phosphorous oxychloride to yield an intermediate dichloro species which undergoes hydrolysis upon aqueous workup to furnish chloropyridazine VIII. Chloro acid VIII is treated with a nucleophile of formula IX in the presence of a base such as sodium hydride. The resultant acid X is reduced with a reducing agent such as $BH_3$.THF according to the procedure of Tilley, J. W.; Coffen D. L. Schaer, B. H.; Lind, J. *J. Org. Chem.* 1987 52 2469. Product alcohol XI is reacted with a base and optionally substituted 4-halo-pridyl, optionally substituted 4-halo-pyrimidyl or optionally substituted 4-halo-pyridazyl (XII) to furnish invention compound of formula I-D4 (for specific reaction conditions see Barlow, J. J.; Block, M. H.; Hudson, J. A.; Leach, A.; Longridge, J. L.; Main, B. g.; Nicholson, S. *J. Org. Chem.* 1992 57 5158).

Method C

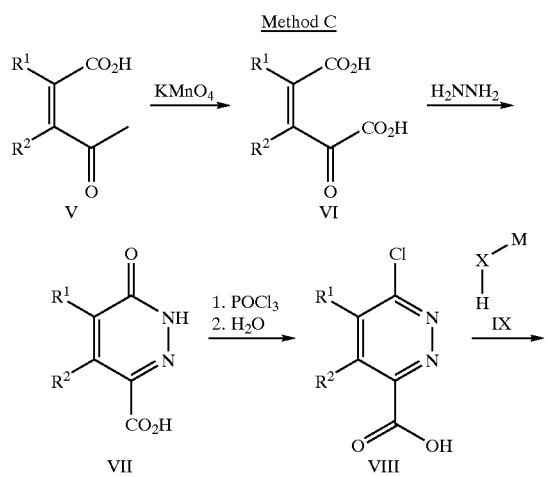

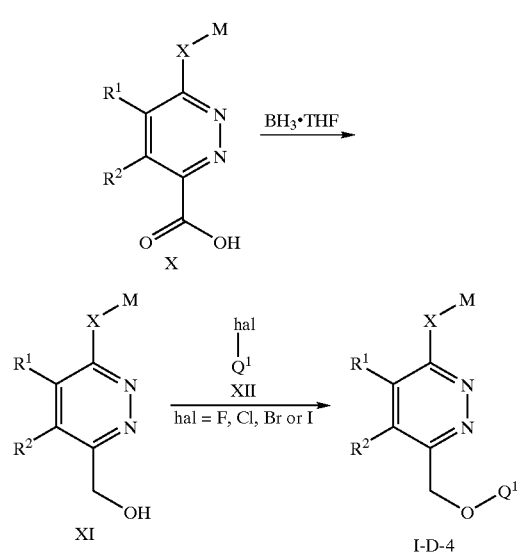

I-D-4

General Method D—The compounds of formula I-D-5 in which M, X, $Q^2$ and Z are defined as above are conveniently prepared according to a reaction sequence as shown in Method D wherein the functional groups which may participate in the reactions are present in protected form where necessary, and the removal of such protective groups is completed at appropriate stages by methods well known to those skilled in the art. Thus, according to the procedure of Bernard, A. M.; Cocco, M. T.; Congiu, C.; Onnis, V.; Piras, P. P. *Synthesis* 1998 317 aryloxy acetonitriles of structure XIII are reacted with acyl hydrazines of structure XIV in the presence of a base such as sodium ethoxide to provide products of formula XV. Compounds of formula XV undergo cyclization upon treatment with an acid such as p-toluenesulfonic acid to furnish phthalizones of formula XVI. Treament of the latter with a chlorinating agent such as phosphorous oxyxhloride yields iminoyl chlorides of the general formula XVII. Conversion to the invention compounds of formula I-D-5 is accomplished by treatment with a nucleophile of formula IX in the presence of a base such as sodium hydride or potassium hydroxide in a solvent such as toluene or tetrahydrofuran. The presence of a crown ether appropriate for the cation such as 18-crown-6 in the case of potassium often accelerates this reaction.

Method D

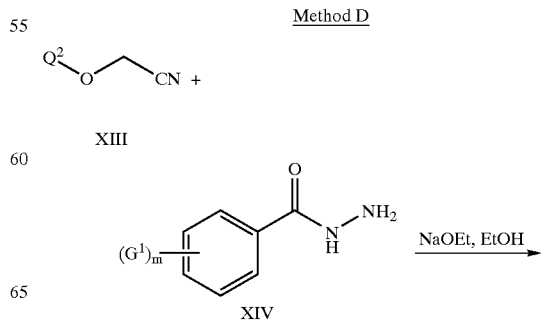

-continued

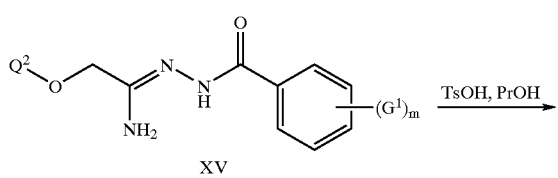

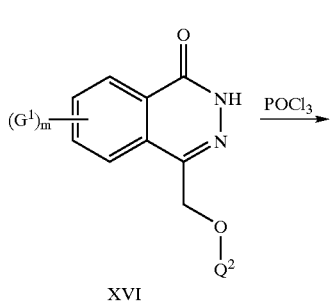

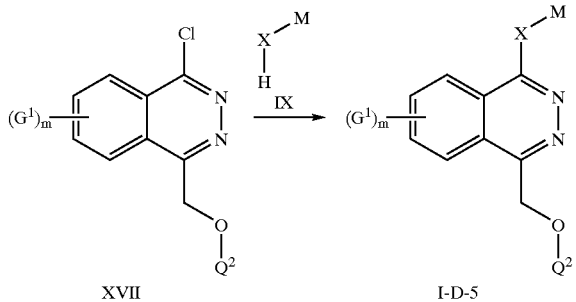

General Method E—The compounds of this invention having formula I-D-6 in which the $R^1$, $R^2$, M, $G^3$, q, and X are defined as above are conveniently prepared via a reaction sequence as shown in Method E. Thus, readily prepared substituted 4-methylpyridazines XVIII are alkylated into substituted 2-aminocarbonyl pyridines of formula XIX by the use of a strong base such as lithium diisopropylamide, sodium hydride or DBU, followed by the addition of 4-halopyridines of formula (XIX). This method is most usefull in those cases wherein $R^1$, $R^2$ and the pyridazine ring taken together form a phthalazine moiety, q is 1, the substituent is on position 2 of the pyridine ring, and said substituent is —$CON(R^6)_2$.

Method E

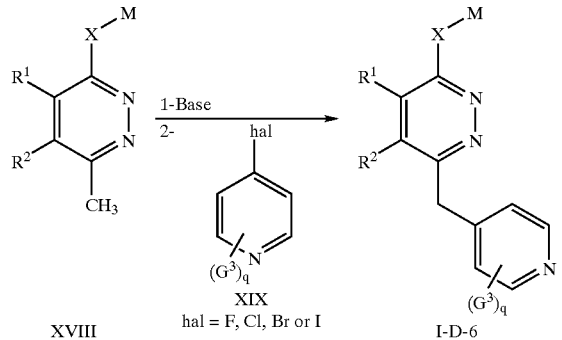

4-Methylpyridazines of formula XVIII are easily prepared from acids or esters of formula XX via a three-step procedure involving (one) cyclization with hydrazine, (two) reaction with a dehydrating or chlorinating agent such as phosphorus pentoxide or phosphorous oxychloride and (three) addition of an nucleophile of formula IX:

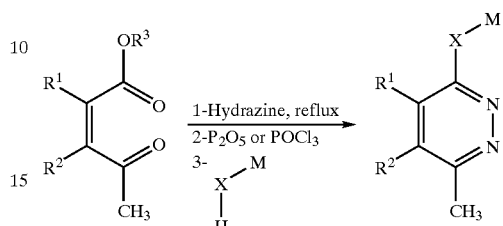

4-Halopyridines of formula XIX are easily prepared by those skilled in the art. Compound XIX-A in which Q is 1 and a substituent —$CO(N^6)_2$ is found on position 2 of the pyridine is obtained from the known 2-chlorocarbonyl-4-chloro-pyridine hydrochloride XXI and amine XXII as follows:

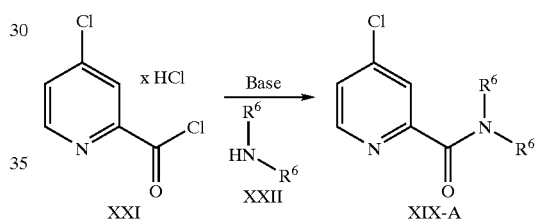

General Method F—Alternatively, the compounds of formula I-D-7-A through I-D-7-E in which the $R^1$, $R^2$, M, $Q^1$ and X are defined as above are conveniently prepared via a reaction sequence as shown in Method F. This method is especially usefull in those cases in which B is a substituted or unsubstituted 4-pyridyl in which case XXIV is a 4-halopyridine. Thus, readily prepared compounds of the formula XXIII are alkylated to yield invention compounds of formula I-D-7-A by the use of a base such as sodium hydride, DBU, or potassium carbonate, followed by the addition of halogenated intermediates of formula XXIV. The resulting pyridazines of formula I-D-7-A are then optionally hydrolyzed and decarboxylated by treatment with hot aqueous acid or base to yield invention compounds of formula I-D-7-B.

Alternatively the treatment of 1-D-7-A with aqueous base such as NaOH at ambient temperature followed by acidification yields invention compounds of structure I-D-7-C. This acid may then be treated with a diazoalkane to yield invention compounds I-D-7-D or with ammonia or a primary or secondary amine in the presence of a coupling agent such as DCC (dicylohexylcarbodiimide) to yield invention compounds of structure I-D-7-E.

Method F

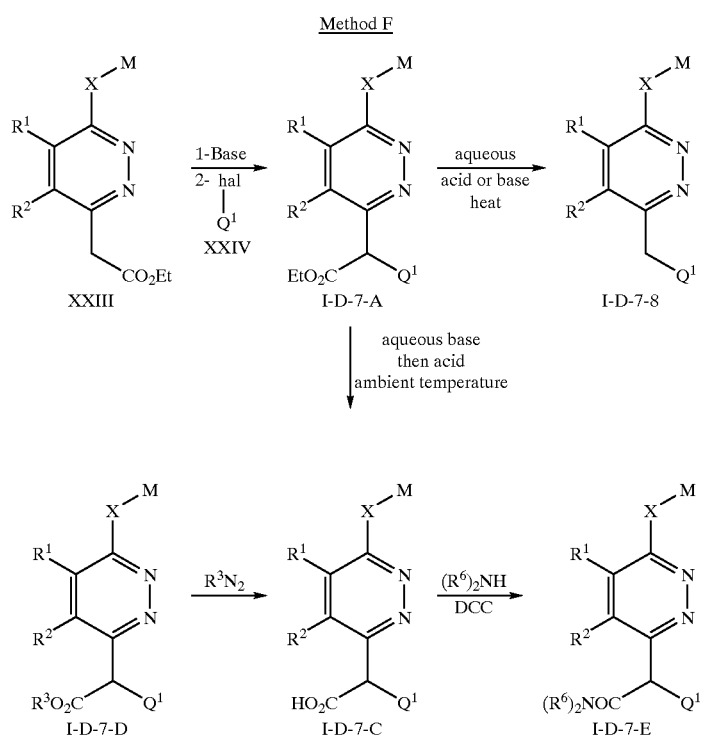

Intermediates of formula XXIII are prepared as follows by methods well known to those skilled in the art. Thus readily available diesters of formula XXVI are treated with hydrazine in a suitable solvent to yield a compound of the formula XXVII. Reaction of XXVII with a suitable chlorinating agent such as $POCl_3$ yields a 1,4-dichloropyridizine which is then reacted with a nucleophile IX as a melt or in the presence of a suitable base such as triethylamine or N-methylmorpholine to yield XXVIII. See *J. Chem Soc.* 1948, 777–782 for a preparation of XXVIII in which M is 4-chlorophenyl, X is NH and $R^1$ and $R^2$ taken together with the pyrazine ring is phthalazine. Alternatively a brominating agent such as $POBr_3$ is used and the intermediates contain bromine rather than chlorine. It is expected that suitable iodinating agents are equally usefull in this process. The key intermediate of structure XXIII is formed from XXVIII upon addition of Meldrum's acid in the presence of base such as NaH, followed by ethanolysis in the presence of a base such as triethylamine.

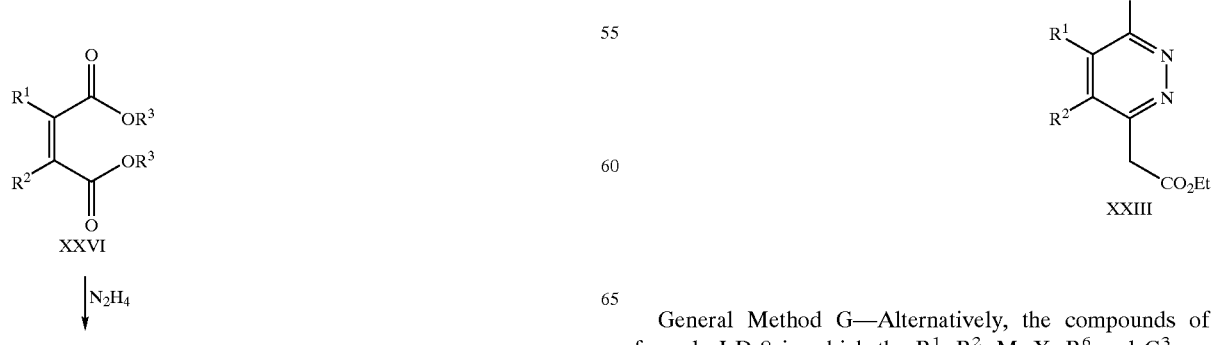

General Method G—Alternatively, the compounds of formula I-D-8 in which the $R^1$, $R^2$, M, X, $R^6$ and $G^3$ are defined as above are conveniently prepared via a reaction sequence as shown in Method G. Thus the methods described in Martin, I; Anvelt, J.; Vares, L.; Kuehn, I.; Claesson, A. *Acta Chem. Scand.* 1995, 49, 230–232 or those of methods A or B above by substituting readily available pyridine-4-carboxylic ester XXIX for I-D are used to convert XXIX into XXX. Reduction of the ester as described by Martin, et al. above is next done with a mild reducing agent such as NaBH$_4$ such that the amide substituent is left unchanged to yield alcohol XXXI. Alcohol XXXI is then heated in a base such as DBU with chloropyridazine XXVIII to yield the invention compound with formula I-D-8.

Method G

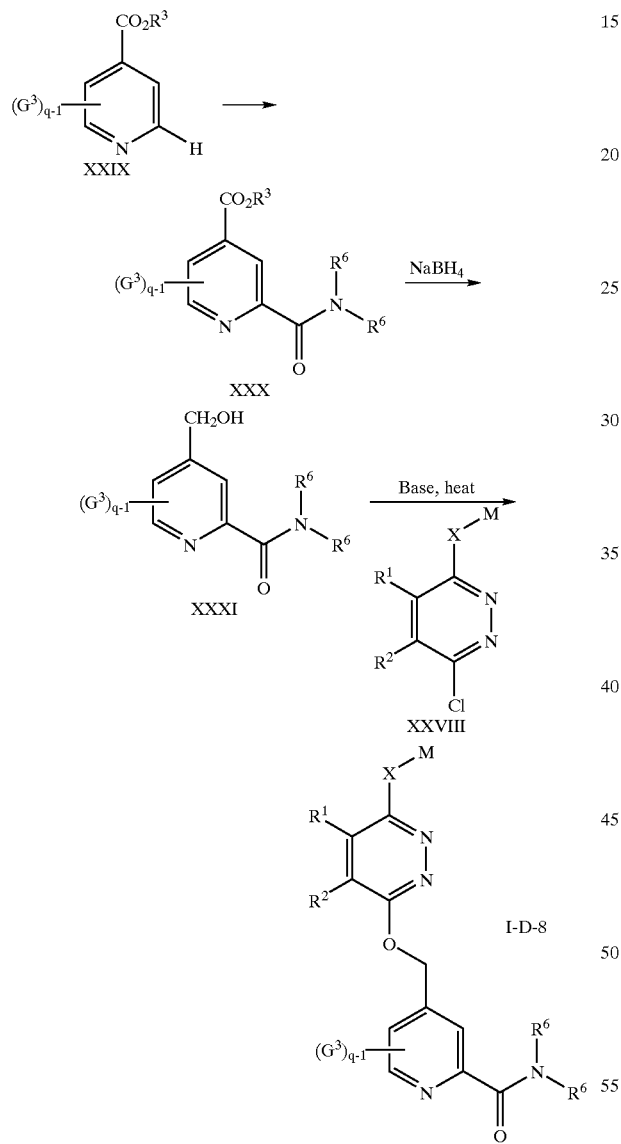

General Method H—Invention compounds having formula I-D-9 in which the $R^1$, $R^2$, M, X, $R^6$, q, and $G^3$ are defined as above and W is a bond or —CH$_2$— are conveniently prepared via a reaction sequence as shown in Method H. This method is especially useful when q is 1 and XXXII is 4-chloropyridine. Alternatively, other 4-halopyridines such as 4-fluoropyridine can be used in this process. Thus readily available 4-chloropyridines XXII are converted to intermediates of formula XXXIII by using the general procedures of methods A or B above by substituting the 4-chloropyridine for I-D. Reaction of XXXIII with either potassium or sodium hydrogen sulfide yields a thiol having formula XXXIV. Alternatively, the alcohol function of intermediate XXXI from method G is converted to a leaving group by reaction with methanesulfonyl chloride and a suitable base such as triethylamine and the resultant intermediate is reacted with either potassium or sodium hydrogen sulfide to yield a thiol having formula XXXV. Either thiol have formula XXXIV or formula XXXV is reacted with intermediate XXVIII from method F and a suitable base such as diisopropylethylamine in DMF or other suitable solvent to yield I-D-9.

Method H

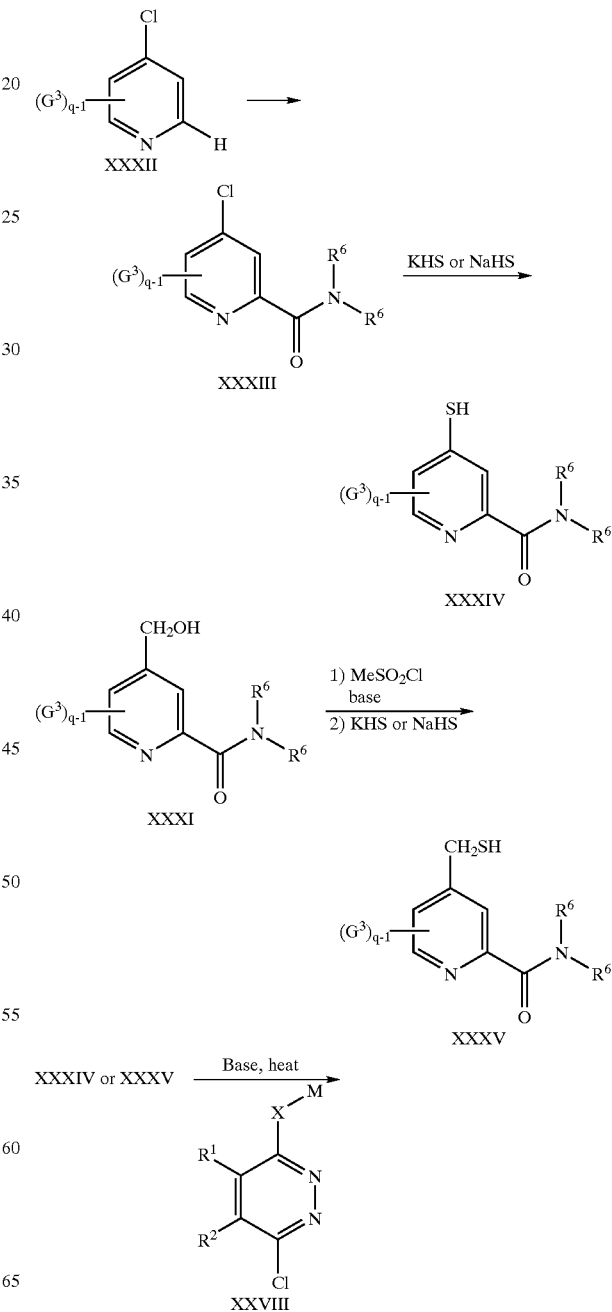

-continued

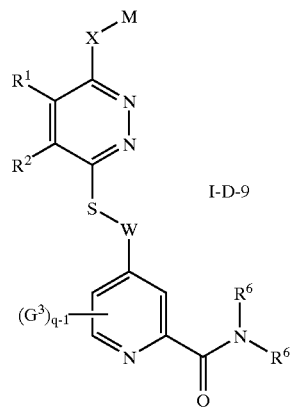

I-D-9

General Method I—Invention compounds having formula I-D-10 in which the $R^1$, $R^2$, M, X, $R^6$, q, and $G^3$ are defined as above are conveniently prepared via a reaction sequence as shown in Method I. Thus alcohol of formula XI from method C is reacted with methanesulfonyl chloride in the presence of a suitable base followed by potassium or sodium hydrogen sulfide to yield thiol XXXVI. The thiol is then reacted with 4-chloropyridine XXXIII from method H in the presence of a suitable base such as triethylamine to yield invention compound I-D-10. Analogous optionally substituted 4-fluoropyridines may be used instead of XXXIII. Alternatively, XI is converted to halo intermediate of formula XXXVII by methods well known to those skilled in the art and XXXVII is reacted with thiol XXXIV from method H to yield I-D-10. Intermediate XXXVII can also be converted to intermediate XXXVI by treatment with KHS or NaHS.

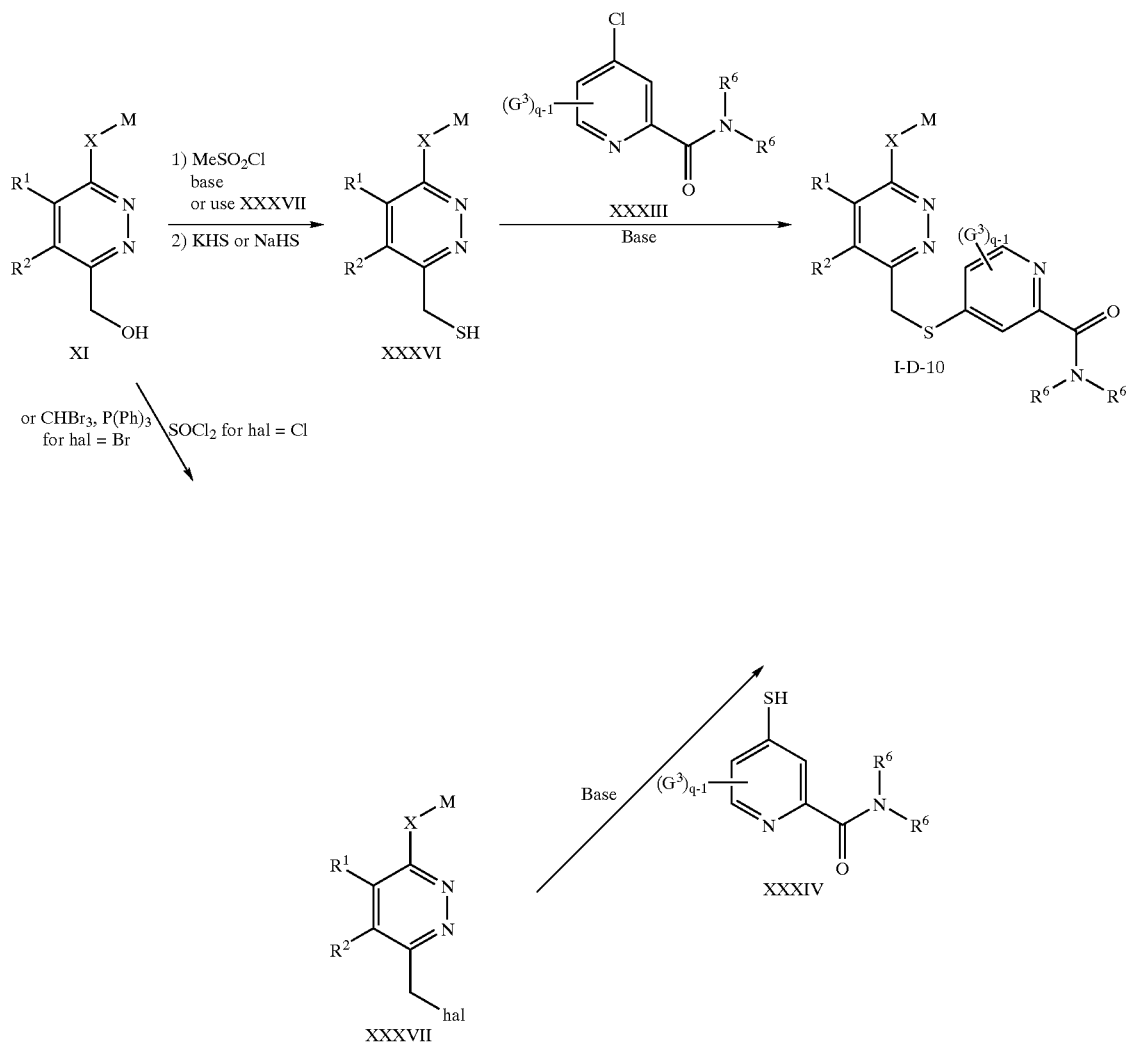

General Method J—Invention compounds having formula I-D-11 or I-D12 in which the $R^1$, $R^2$, M, X, W, and $G^3$ are defined as above and a sulfoxide or sulfone within the structure are conveniently prepared via a reaction sequence as shown in Method J. Reaction of compounds of this invention that contain a thio group either as part of a substituent $G^1$, $G^3$, or $G^4$ or as part of Y as shown in the representative structure XVIII can be converted to the invention compounds with a sulfoxide moiety such as I-D-11 by treatment with one equivalent of m-chloroperbenzoic acid in methylene chloride or chloroform (MCPBA, Synth. Commun., 26, 10, 1913–1920, 1996) or by treatment with sodium periodate in methanol/water at between 0° C. and room temperature (J. Org. Chem., 58, 25, 6996–7000, 1993). The expected side products consisting of mixtures of various N oxides and the sulfone I-D-12 can be removed by chromatography. The sulfone I-D-12 is obtained by the use of an additional equivalent of MCPBA or preferably by use of potassium permanganate in acetic acid/water (Eur. J. Med. Chem. Ther., 21, 1, 5–8, 1986) or by use of hydrogen peroxide in acetic acid (Chem. Heterocycl. Compd., 15, 1085–1088, 1979). In those cases that unwanted N oxides become a significant product, they can be converted back to the desired sulfoxides or sulfones by hydrogenation in ethanol/acetic acid with palladium on carbon catalysts (Yakugaku Zasshi, 69, 545–548, 1949, Chem. Abstr. 1950, 4474).

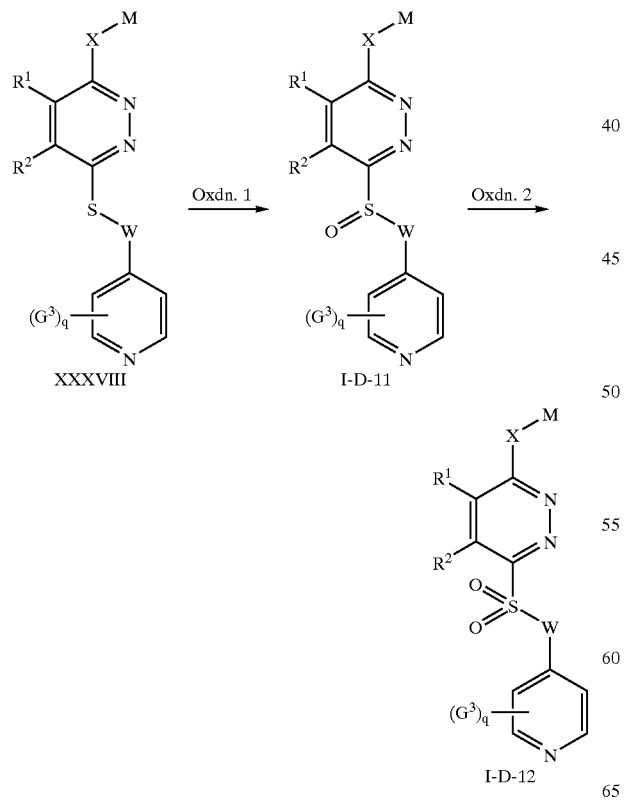

EXPERIMENTAL

Example 1

Preparation of 4-[4-(4-Chlorophenylamino)phthalazin-1-ylmethyl]pyridin-2-yl carboxylic acid methylamide

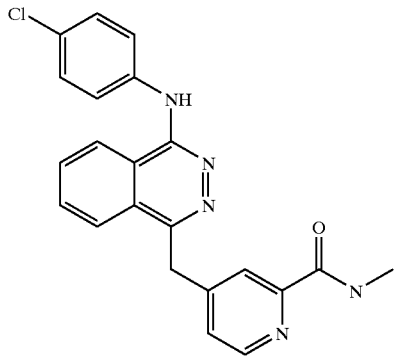

To a 3-necked flask charged with 1-(4-chloroanilino) 4-[(2-methyl-4-pyridyl)methyl] phthalazine (for preparation see Novartis patent WO98/35958, 11.02.98) (0.828 g, 2.39 mmol) in anhydrous N-methylformamide (4.8 mL) was added concentrated sulfuric acid)0.12 mL. 2.39 mmol) and iron (II) sulfate heptahydrate (0.33 g, 1.19 mmol). Hydrogen peroxide (0.256 mL, 8.35 mmol; 30 wt. % solution in water) was added dropwise to keep the internal temperature below 80° C. The resultant wine color reaction was then stirred at 70° C. for 5 h. The reaction mixture was cooled to RT and quenched with 10% aqueous sodium hydroxide (10 mL) followed by 10% aqueous ammonia (~100 mL). The resultant brown precipitate was filtered through a pad of celite, and the filtrate was extracted with 10% methanol-dichloromethane (3×100 mL). The combined organic phases were washed with water (2×50 mL) and brine (1×50 mL), dried over $MgSO_4$, filtered, and evaporated in vacuo. The crude oil was purified by flash column chromatography (10% acetone-dichloromethane followed by 1:4:20 v/v methanol-acetone-dichloromethane). Recrystallization from methanol afforded 0.165 g (0.404 mmol, 17% yield) of the title compound as a yellow solid. $^1$H-NMR (DMSO-$d_6$) 9.28 (s, 1H), 8.70 (d, J=4.9, 1H), 8.58 (d, J=7.4, 1H), 8.49 (d, J=5.4, 1H), 8.12 (d, J=8.4, 1H), 7.89 to 7.99 (m, 5H), 7.51 (dd, J=5.1, 1.7, 1H), 7.38 (dd, J=7.1, 1.9, 2H), 4.67 (s, 2H), 2.75 (d, J=4.9, 3H); MS ES 404 (M+H)$^+$, calc. 403; TLC (1:4:15 v/v methanol-acetone-dichloromethane) $R_f$=0.74.

EXAMPLE 2

Preparation of 4-[4-(4-Chlorophenylamino)phthalazin-1-ylmethyl]pyridin-2-yl carboxylic acid amide

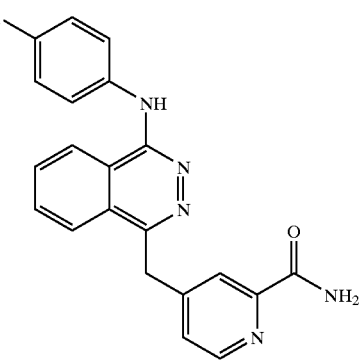

The procedure used for the preparation of Example 1, but replacing N-methylformamide with formamide, was used to prepare the title compound (0.065 g, 0.167 mmol, 19% yield). $^1$H-NMR (DMSO-d$_6$) 9.27 (s, 1H), 8.58 (d, J=7.6, 1H), 8.49 (d, J=4.5, 1H), 8.12 (d, J=7.7, 1H), 8.06 (broad s, 1H), 7.90 to 8.00 (m, 5H), 7.59 (broad s, 1H), 7.53 (dd, J=5.0, 1.5, 1H), 7.37 (d, J=8.7, 2H), 4.66 (s, 2H); MS ES 390 (M+H)$^+$, calc. 389; TLC (1:4:15 v/v methanol-acetone-dichloromethane) R$_f$=0.31.

EXAMPLE 3

Preparation of 1-(4-chlorophenylamino)-4-(3-pyridylmethoxy)phthalazine

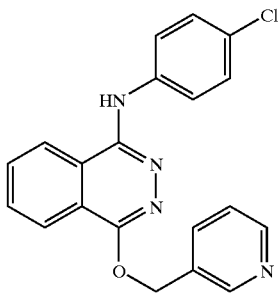

A dry 50-mL round-bottomed flask was equipped with a stir bar and an argon inlet. The flask was charged with 1-chloro-4-(4-chlorophenylamino)-phthalazine (R. D. Haworth and S. Robinson, J. Chem. Soc. 1948, pp.777–782) (2.00 g; ~6.12 mmol), 3-pyridyl-carbinol (Aldrich) (10.02 g, 91.85 mmol), and DBU (18.3 mL, ~18.7 g, ~123 mmol). The reaction was heated at 125 C for 28 h. The mixture was cooled to room temperature and distilled water (400 mL) was added with stirring. The aqueous phase was extracted with ethyl acetate (3×300 mL). The combined organics were dried (MgSO4) and concentrated to yield a tan solid, which was purified by silica gel chromatography (100% dichloromethane→50% acetone/dichloromethane) to give the clean desired compound as a white solid (1.24 g, 3.42 mmol; 56% yield). TLC (20% acetone/dichloromethane): R$_f$=0.48.

EXAMPLE 4

Preparation of 4-[4-(4-Chlorophenylamino)phthalazin-1-yloxymethyl]pyridin-2-yl carboxylic acid methylamide

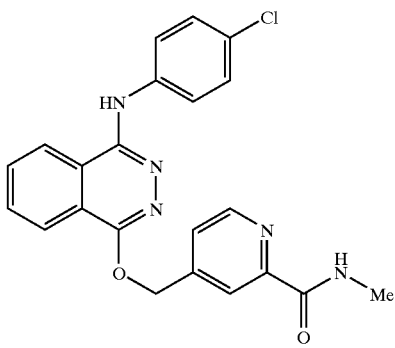

Step 1: Preparation of 1-(4-chlorophenylamino)-4-(4-pyridylmethoxy)-phthalazine

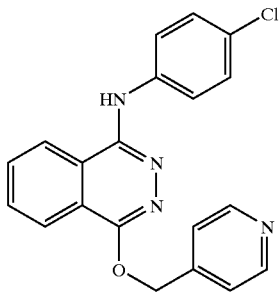

The general procedure used for the preparation of Example 3 was used in step 1 of the preparation of Example 4 from 1-chloro-4-(4-chlorophenylamino)phthalazine and 4-pyridyl-carbinol; (87% yield). TLC (20% acetone/dichloromethane): R$_f$=0.26.

Step 2:

Caution—this reaction is potentially explosive and latent violent exotherms have been noted, especially if the reaction is heated and unreacted hydrogen peroxide is present. The product of step 1 above (0.600 g, 1.65 mmol) was dissolved in 16.5 ml of N-methyl-formamide. The reaction was charged with concentrated sulfuric acid (0.264 ml, 4.96 mmol) followed by FeSO4-7H2O (0.115 g, 0.413 mmol). The solution was stirred at ambient temperature for 15 min then 30% wt. hydrogen peroxide/water (0.338 ml, 3.31 mmol) was added (exotherm noted). TLC analysis after 1 h indicates the reaction is 50% done. The reaction was again charged with concentrated sulfuric acid (0.264 ml, 4.96 mmol) followed by FeSO4-7H$_2$O (0.115 g, 0.413 mmol). To the reaction is added 6 aliquots of 30% wt. hydrogen peroxide/water (each aliquot is 0.338 ml, 3.31 mmol) over 3 h. The opaque brown reaction was stirred for 24 h at 30 C. TLC analysis now indicates no starting material is present. The reaction was quenched with saturated potassium carbonate (100 ml) and the solids filtered off washing with water. The aqueous layer was extracted with diethyl ether (3×175 ml), and the combined organics dried (MgSO4) and concentrated to give an orange solid. The crude product was purified by silica gel chromatography (100% dichloromethane→10% acetone/dichloromethane) to give the clean desired compound as a tan solid (64 mg, 0.152 mmol; 9% yield). TLC (10% acetone/dichloromethane): R$_f$=0.38.

EXAMPLE 5

Preparation of 4-[4-(4-Chlorophenylamino)phthalazin-1-yloxymethyl]pyridin-2-yl carboxylic acid amide

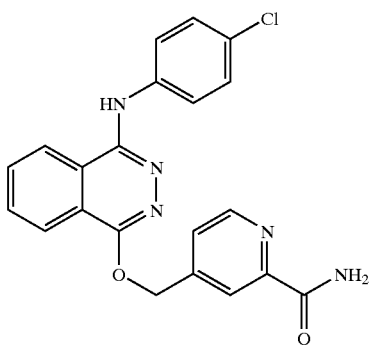

The general procedure used for the preparation of Example 4 was used to prepare 5 from 1-(4-chlorophenylamino)-4-(4-pyridylmethoxy)phthalazine and formamide; (10% yield). TLC (dichloromethane/acetone/triethylamine 7.5:1.0:0.5): $R_f$=0.42.

EXAMPLE 6

Preparation of 4-[4-(3-Bromophenylamino)phthalazin-1-ylmethyl]-pyridin-2-yl carboxylic acid methylamide

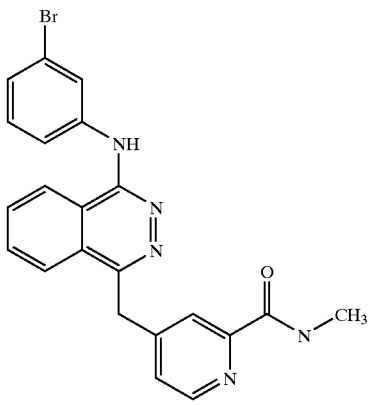

The procedure used for the preparation of Example 1 was used to prepare the title compound (0.15 g, 0.33 mmol, 33% yield) from 1-(3-bromoanilino) 4-[(2-methyl-4-pyridyl)methyl] phthalazine (for preparation see Novartis patent WO98/35958, 11.02.98). $^1$H-NMR (DMSO-$d_6$): 9.30 (s, 1H), 8.70 (d, J=5.1, 1H), 8.58 (d, J=7.7, 1H), 8.49 (d, J=5.3, 1H), 8.35 (t, 1.8, 1H), 8.13 (d, J=8.3, 1H), 7.88 to 8.01 (m, 4H, 7.51 (dd, J=5.0, 1.5, 1H), 7.29 (t, J=8.2, 1H), 7.18 (d, J=7.7, 1H), 4.68 (s, 2H), 2.75 (d, J=4.9, 3H); MS ES '449 (M+H)$^+$, calc. 448; TLC (20% acetone-dichloromethane) $R_f$=0.37.

EXAMPLE 7

Preparation of 4-[4-(3-Bromophenylamino)phthalazin-1-ylmethyl]-pyridin-2-yl carboxylic acid amide

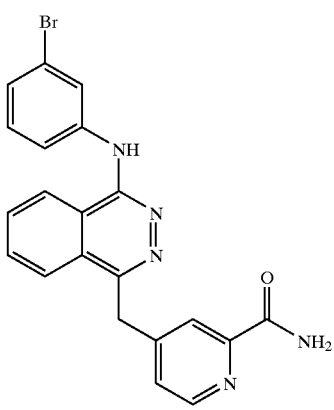

The procedure used for the preparation of Example 1, but replacing N-methylformamide with formamide, was used to prepare the title compound (0.059 g, 0.13 mmol, 10.6% yield) from 1-(3-bromoanilino) 4-[(2-methyl-4-pyridyl)methyl]phthalazine (for preparation see Novartis patent WO98/35958, 11.02.98). $^1$H-NMR (DMSO-$d_6$) 9.31 (s, 1H), 8.58 (d, J=7.7, 1H), 8.49 (d, J=5.3, 1H), 8.35 (s, 1H), 8.13 (d, J=7.5, 1H), 8.05 (broad s, 1H), 7.89 to 7.99 (m, 4H), 7.59 (broad s, 1H), 7.53 (dd, J=5.1, 1.5, 1H), 7.29 (t, J=8.0, 1H), 7.18 (d, J=7.8, 1H), 4.68 (s, 2H); MS ES 434/436 (M+H)$^+$ w/1Br, calc. 433; TLC (1:4:15 v/v methanol-acetone-dichloromethane) $R_f$=0.59.

EXAMPLE 8

Preparation of 1-(4-chlorophenylamino)-4-[(2-phenyl-4-pyridyl)methyl]phthalazine

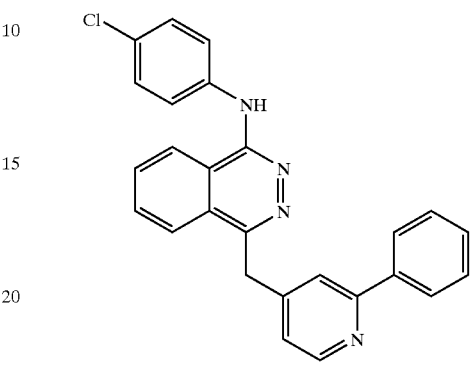

Step 1: Preparation of 2-(2-phenylpyridin-4-ylidene)indan-1,3-dione

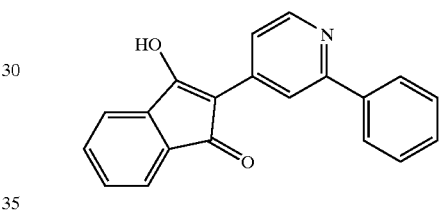

Under exclusion of air, a mixture of phthalic anhydride (4.38 g, 29.5 mmol) and 2-phenyl-4-picoline (5.0 g, 29.5 mmol) was heated to 200° C. The reaction melt was stirred at 200° C. for 14 h until a yellow precipitate was formed. The reaction was cooled to 100° C. and ethanol (300 mL) was added. The resultant brown mass was refluxed in ethanol for 1 h and sonicated in a water bath to break up the compound. The precipitate was filtered and triturated in ethanol (100 mL) to give the title compound as a yellow solid (3.2 g, 10.7 mmol, 36% yield). $^1$H-NMR (DMSO-$d_6$) 12.06 (broad s, 1H), 9.04 (d, J=1.3, 1H), 8.68 (dd, J=6.7, 1.3, 1H), 8.17 (d, J=6.7, 1H), 7.79 (dd, J=8.0, 5.2, 2H), 7.61 to 7.64 (m, 3H), 7.45 to 7.53 (m, 4H); MS ES 300 (M+H)$^+$, calc. 299; TLC (1:2:8 v/v methanol-acetone-dichloromethane) $R_f$=0.32.

Step 2: Preparation of 4-[(2-phenyl-pyridinyl)methyl]-1(2H)-phthalazinone

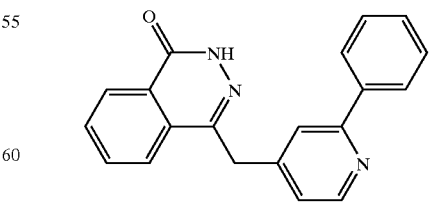

A mixture of 2-(2-phenyl-pyridin-4-ylidene)-indan-1,3-dione (3.1 g, 10.4 mmol) and hydrazine hydrate (9.7 mL) was stirred at 130° C. under argon for 5 h. The reaction mixture was cooled and filtered. The resultant tacky solid was dissolved in ethyl acetate (250 mL) and then washed with water (2×50 mL) and brine (1×50 mL). The organic layer was dried over MgSO4, filtered, and evaporated in vacuo. Trituration from ether afforded the title compound as a beige solid (2.82 g, 9.0 mmol, 86% yield). $^1$H-NMR (DMSO-d$_6$) 12.59 (broad s, 1H), 8.52 (d, J=4.6, 1H), 8.24 (dd, J=7.7, 1.0,1H), 7.95 to 8.03 (m, 4H), 7.78 to 7.91 (m, 2H), 7.40 to 7.49 (m, 3H), 7.21 (d, J=6.5, 1H), 4.39 (s, 2H); MS ES 314 (M+H)$^+$, calc.313; TLC (1:2:8 v/v methanol-acetone-dichloromethane) R$_f$=0.40.

Step 3:

A mixture of 4-chloroaniline (1.63 g, 12.76 mmol), phosphorus pentoxide (1.81 g, 12.76 mmol) and triethylamine hydrochloride (1.76 g, 12.76 mmol) was heated and stirred under argon at 200° C. for 1.5 h or until a homogenous melt has formed. To the melt was added 4-[(2-phenyl-pyridinyl)-methyl]-1(2H)phthalazinone (1.0 g, 3.19 mmol) and the reaction mixture was stirred at 200° C. for 2 h. The resultant solid black mass was cooled to 100° C. Methanol (~100 mL) and water (~400 mL) were added and the reaction mixture was sonicated until the black mass has become soluble. Dichloromethane (250 mL) was then added to form a biphasic layer, and concentrated ammonia (~5 mL) was added to adjust the reaction to pH=8. The organic layer was separated, and the aqueous layer was extracted with dichloromethane (3×100 mL). The combined organic layers were dried over Na$_2$SO$_4$, filtered, and concentrated. Purification by flash column chromatography (15% acetone/dichloromethane) yielded 1.25 g (2.96 mmol, 93% yield) of the title compound as a beige solid. $^1$H-NMR (DMSO-d$_6$) 9.26 (s, 1H), 8.57 (d, J=8.1, 1H), 8.49 (d, J=4.9, 1H), 8.19 (d, J=8.2, 1H), 7.89 to 8.02 (m, 7H), 7.36 to 7.48 (m, 5H), 7.20 (dd, J=5.0, 1.3, 1H), 4.60 (s, 2H); MS ES 423 (M+H)$^+$, calc.422; TLC (20% acetone-dichloromethane) R$_f$=0.29.

EXAMPLE 9

Preparation of 1-[4-(4-pyridyloxy)phenylamino]-4-(4-pyridylmethyl)phthalazine

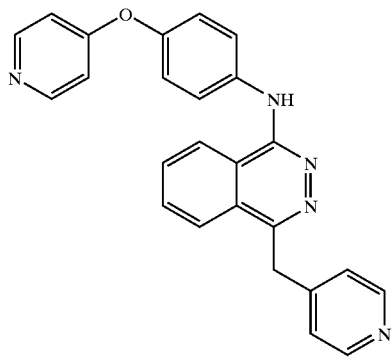

A mixture of 1-chloro-4-(4-pyridylmethyl)phthalazine (for preparation see Novartis patent WO98135958, 11.02.98) (0.540 g, 2.11 mmol) and 4-(4-aminophenoxy) pyridine (1.18 g, 6.33 mmol) in anhydrous 1-butanol (8.4 mL) was stirred under argon at 130° C. for 18 h. The reaction mixture was quenched with saturated aqueous potassium carbonate (~50 mL) and then extracted with dichloromethane (3×100 mL). The combined organic phases were dried over MgSO$_4$, filtered, and concentrated. Purification by flash column chromatography in 7:11:2 v/v acetone-dichloromethane-methanol provided the title compound as an oil (0.340 g, 0.84 mmol, 40% yield). $^1$H-NMR (DMSO-d$_6$) 9.26 (s, 1H), 8.58 (d, J=8.3, 1H), 8.41 to 8.44 (m, 4H), 8.10 (d, J=8.2, 11H), 7.90 to 8.03 (m, 4H), 7.30 (d, J=5.9, 2H), 7.17 (d, J=9.2, 2H), 6.91 (d, J=5.8, 2H), 4.56 (s, 2H); MS ES 406 (M+H)$^+$, calc. 405; TLC (1:7:12 v/v methanol-acetone-dichloromethane) R$_f$=0.08.

EXAMPLE 10

Preparation of 1-(indan-5-ylamino)-4-(4-pyridylmethyl) phthalazine

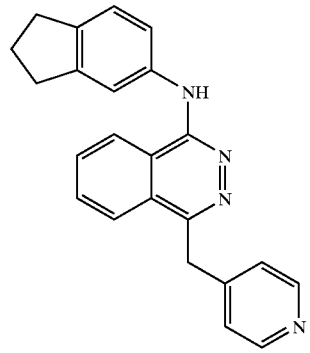

The procedure used for the preparation of Example 9 was used to prepare the title compound (0.06 g, 0.17 mmol, 4.3% yield) by substituting 5-aminoindane for 4-(4-aminophenoxy)pyridine. $^1$H-NMR (DMSO-d$_6$) 9.01 (s, 1H), 8.56 (d, J=7.2, 1H), 8.42 (dd, J=4.3, 1.4, 2H), 8.05 (d, J=8.6, 1H), 7.85 to 7.95 (m, 3H), 7.56 (dd, J=8.3, 2.0, 1H), 7.28 (dd, J=4.3, 1.4, 2H), 7.16 (d, J=8.1, 1H), 4.54 (s, 2H), 2.79 to 2.89 (m, 4H), 1.96 to 2.07 (m, 2H); MS ES 353 (M+H)$^+$, calc. 352; TLC (3:17:80 v/v methanol-acetone-dichloromethane) R$_f$=0.20.

EXAMPLE 11

Preparation of 4-[4-(4-Chlorophenylamino)phthalazin-1-ylmethyl]pyridin-2-yl carboxylic acid methylamide dihydrochloride

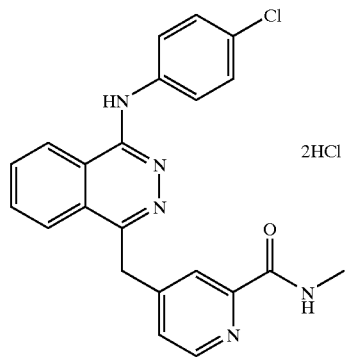

A 50 mL, round-bottomed flask was equipped with a stir bar. To the flask was added BAY 50-9193 (250 mg, 0.62 mmol) in hot MeOH (10 mL). HCl in MeOH (3.8 N) was added dropwise until solution was pH 2. The solution was concentrated to half-volume by rotary evaporation. Ether was added until the solution became cloudy. The solution was cooled to RT before filtering. The orange solid was washed with 2:1 ether:MeOH (5 mL) followed by ether (5 mL). The solid was dried under HV overnight at 50° C. Desired compound (61 mg, 0.13 mmol, 21% yield): m.p. 255° C. (dec.); $^1$H NMR (DMSO-d$_6$) 8.93–8.96 (m, 1H), 8.73–8.74 (m, 1H), 8.53 (d, J=5.3, 1H), 8.37–8.40 (m, 1H), 8.20–8.23 (m, 2H), 8.04 (s, 1H), 7.55–7.67 (m, 5H), 4.77 (s, 2H), 2.76 (d, J=4.6, 3H); ES MS (M+H)$^+$=404; TLC (dichloromethane-acetone, 90:10): R$_f$=0.44; Anal. calc'd. $C_{22}H_{22}N_5OCl_3 \cdot 0.5H_2O$. C, 54.39; H, 4.36; N, 14.42, Cl, 21.89; found C 54.39, H 4.37, N 14.30, Cl 20.17.

EXAMPLE 12

Preparation of 4-[4-(4-Chlorophenylamino)phthalazin-1-ylmethyl]pyridin-2-yl carboxylic acid methylamide dimethanesulfonate

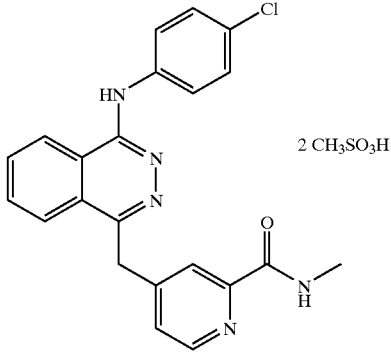

A 50 mL, round-bottomed flask was equipped with a stir bar. To the flask was added BAY 50-9193 (250 mg, 0.62 mmol) in hot MeOH (10 mL). Methanesulfonic acid (90 µL, 1.24 mmol) was added to solution. The solution was concentrated to half-volume by rotary evaporation. Ether was added until the solution became cloudy. The solution was cooled to 0° C. before filtering. The yellow solid was washed with ether (5 mL). The solid was dried under HV overnight at 50° C. Desired compound (309 mg, 0.52 mmol, 84% yield): m.p. 245–249° C.; $^1$H NMR (DMSO-d$_6$) 8.82 (dd, J=1.8, 5.2, 1H), 8.72–8.76 (m, 1H), 8.54 (d, J=5.1, 1H), 8.39–8.42 (m, 1H), 8.20–8.27 (m, 1H), 8.04 (s, 1H), 7.55–7.65 (m, 5H), 4.75 (s, 2H), 2.76 (d, J=4.7, 3H), 2.33 (s, 6H); ES MS: (M+H)$^+$=404; TLC (dichloromethane-acetone, 90:10): R$_f$=0.45; Anal. calc'd: $C_{24}H_{26}N_5O_7S_2Cl \cdot 0.6H_2O$. C, 47.57; H, 4.51; N, 11.56; Cl, 5.85; S, 10.58%; found C, 47.57; H, 4.50; N, 11.43, Cl 5.88, S 10.88.

EXAMPLE 13

Preparation of 4-[4-(4-Chlorophenylamino)phthalazin-1-ylmethyl]pyridin-2-yl carboxylic acid amide dihydrochloride A 50 mL, rotund-bottomed flask was equipped with a stir bar. To the flask was added BAY 50-9323 (250 mg, 0.16 mmol) in hot MeOH (10 mL). HCl in MeOH (3.8N, ~2 mL) was added dropwise until solution was pH 2. The solution was concentrated to half-volume by rotary evaporation. Ether was added until solution became cloudy. The solution was cooled to RT before filtering. The orange solid was washed with 2:1 ether:MeOH (~5 mL) then ether (~5 mL). Solid was dried in vacuum oven overnight at 50° C. Desired compound (34 mg, 0.073 mmol; 11% yield); mp=180–198° C.; $^1$H NMR (DMSO-d$_6$) 9.00–9.03 (m, 1H), 8.54 (d, J=5.2, 1H), 8.37–8.41 (m, 1H), 8.20–8.23 (m, 1H), 8.09 (s, 1H), 8.05 (s, 1H), 7.62 (dd, J=7.7, 25, 6H), 4.78 (s, 2H); ES MS (M+)$^+$=390; TLC (dichloromethane-acetone, 95:5); R$_f$ =0.44; Anal. Calc for $C_{21}H_{18}N_5OCl_3$. C, 54.51; H, 3.92; N, 15.13, Cl 22.98; found C, 54.31; H, 4.03; N, 13.93, Cl 22.72.

EXAMPLE 14

Preparation of 4-[4-(4-Chlorophenylamino)phthalazin-1-ylmethyl]pyridin-2-yl carboxylic acid amide dimethanesulfonate

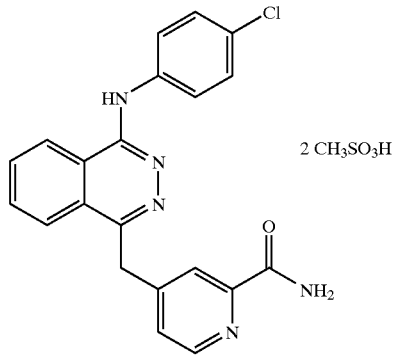

A 25 mL, round-bottomed flask was equipped with a stir bar. To the flask was added BAY 50-9323 (250 mg, 0.64 mmol) in hot MeOH (8 mL). Methanesulfonic acid (93 µL, 1.28 mmol) was added to solution. Ether was added until the solution became cloudy. Solution was cooled to 0° C. before filtering. The yellow solid was washed with ether (5 mL). The solid was dried under HV overnight at 50° C. Desired compound (382 mg, 0.66 mmol, 99% yield): m.p. 156–161° C.; $^1$H NMR (DMSO-d$_6$) 8.82 (dd, J=2.0, 5.5, 1H), 8.55 (d, J=4.5, 1H), 8.39–8.42 (m, 1H), 8.22–8.25 (m, 2H), 8.09 (s, 1H), 8.04 (s, 1H), 7.57–7.65 (m, 5H), 4.75 (s, 2H), 2.32 (s, 6H); ES MS: (M+H)$^+$=390; TLC (dichloromethane-acetone, 90:10): R$_f$=0.18; Anal. calc'd: $C_{23}H_{24}N_5O_7S_2Cl \cdot 1.5H_2O$ C, 45.38; H, 4.46; N, 11.50; Cl, 5.82; S, 10.53; found C, 45.38; H, 4.28; N, 11.27, Cl 5.85, S 10.93.

EXAMPLE 15

Preparation of 4-[4-(4-Chlorophenylamino)phthalazin-1-yloxymethyl]pyridin-2-yl carboxylic acid amide dihydrochloride

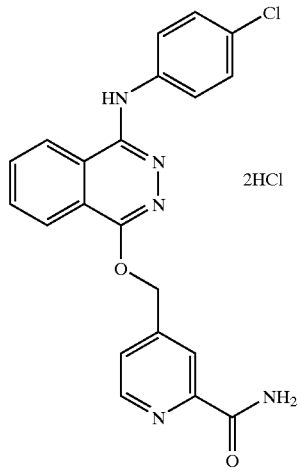

A 50 mL, round-bottomed flask was equipped with a stir bar. To the flask was added BAY 50-9644 (300 mg, 0.74 mmol) in hot EtOH (10 mL). HCl in MeOH (3.8N, ~2 mL) was added dropwise until solution was pH 2. The solution was concentrated to half-volume by rotary evaporation. Ether was added until solution became cloudy. The solution was cooled to RT before filtering. The yellow solid was washed with ether (~5 mL). The solid was dried in vacuum oven overnight at 50° C. Desired compound (320 mg, 0.67 mmol; 91% yield); mp=143–145.2° C.; $^1$H NMR (DMSO-$d_6$) 11.87 (s, 1H), 9.18 (d, J=8.8, 1H), 8.66 (d, J=5.2, 1H), 8.40 (d, J=8.8, 1H), 8.18–8.30 (m, 4H); 7.77 (dd, J=1.3, 5, 1H), 7.74 (s, 1H); 7.55–7.75 (m, 4H), 5.65 (s, 2H); ES MS (M+H)$^+$=406; TLC (dichloromethane-acetone, 95:5); $R_f$=0.184; Anal. Calc for $C_{21}H_{18}N_5O_2Cl_3 \cdot 0.8H_2O$ C, 51.07; H, 4.02; N, 14.18; Cl, 21.53; found C, 51.07; H, 4.13; N, 14.77, Cl 20.42.

EXAMPLE 16

Preparation of 4-[4-(4-Chlorophenylamino)phthalazin-1-yloxymethyl]pyridin-2-yl carboxylic acid amide dimethanesulfonate

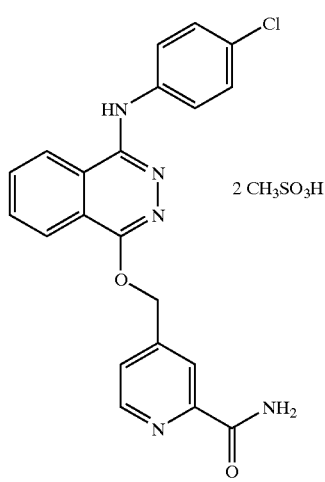

A 50 mL, round-bottomed flask was equipped with a stir bar. To the flask was added BAY 50-9644 (300 mg, 0.74 mmol) in hot EtOH (10 mL). Methanesulfonic acid (0.1 mL, 1.48 mmol) was added to solution. The solution was concentrated to half-volume by rotary evaporation. Ether was added until solution became cloudy. The solution was cooled to RT before filtering. The yellow solid was washed with ether (~5 mL). The solid was dried in vacuum oven overnight at 50° C. Desired compound (393 mg, 0.66 mmol; 89% yield); mp=75–80° C.; $^1$H NMR (DMSO-$d_6$) 11.23 (s, 1H), 8.81 (d, J=9.2, 1H), 8.67 (d, J=4.8, 1H), 8.43 (d, J=9.2, 1H), 8.24–8.32 (m, 2H), 8.18 (s, 1H), 8.17 (s, 1H), 7.78 (dd, J=1.5, 5.1, 1H), 7.74 (s, 1H), 7.59 (dd, J=9.0, 18.9 Hz, 4H), 5.66 (s, 2H), 2.37 (s, 6H); ES MS (M+H)$^+$=406; TLC (dichloromethane-acetone, 95:5); $R_f$=0.195; Anal. Calc for $C_{23}H_{24}N_5O_8S_2Cl \cdot 1.6H_2O$ C, 44.06; H, 4.37; N, 11.17; Cl, 5.65; S, 24.51; found C 44.06, H 4.35, N 11.18, Cl 5.74, S 10.64.

EXAMPLE 17

Preparation of 1-(4-chlorophenylamino)-4-[5-(4-pyridyl)-1H-1,2,4-triazolyl-3-ylthio]phthalazine

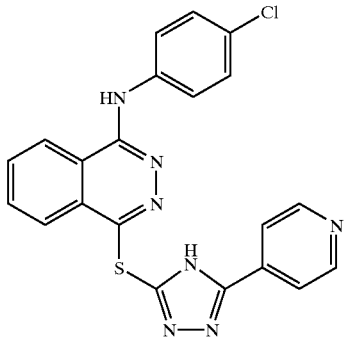

A mixture of 1-chloro-4-(4-chlorophenylamino) phthalazine hydrochloride (R. D. Haworth and S. Robinson, J. Chem. Soc. 1948, pp.777–782)(275 mg; 0.84 mmol), 5-(4-pyridyl)-1H-1,2,4-triazole-3-thiol (303 mg, 1.67 mmol), diisopropylethylamine (3 ml) and dimethylformamide (3 ml) was heated at 100° C. under argon for 15 hr. The resultant product residue was dissolved in ethyl acetate and the resultant solution was washed with water and brine, died over magnesium sulfate and then evaporated in vacuo. The residue of crude product was purified by chromatography on silica gel using 4% methanol in methylene chloride to yield 29 mg of pure title compound, $R_f$ 0.36 (10% methanol in methylene chloride).

EXAMPLE 18

Preparation of 1-(4-isopropylphenylamino)-4-[5-(4-pyridyl)-1H-1,2,4-triazolyl-3-ylthio]phthalazine

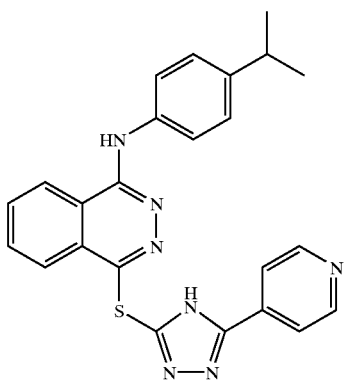

Using the method of example 17 and 1-chloro-4-(4-isopropylphenylamino)phthalazine (250 mg, 0.84 mmol) rather than 1-chloro-4-(4-chlorophenylamino)phthalazine hydrochloride yielded 21 mg of the pure title compound, $R_f$ 0.28 (10% methanol in methylene chloride).

EXAMPLE 19

Preparation of 1-(4-chlorophenylamino)-4-(4-pyridylsufonyl)phthalazine

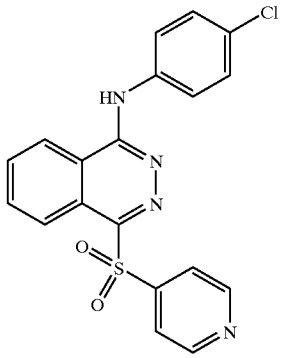

1-Chloro-4-(4-chlorophenylamino)-phthalazine (R. D. Haworth and S. Robinson, J. Chem. Soc. 1948, pp.777–782) (2.00 g; ~6.12 mmol) can be melted together with one equivalent of 4-mercaptopyridine at about 140° C. for about 10–30 min. to yield a residue which is dissolved in ethyl acetate, washed with aqueous sodium carbonate and then evaporated in vacuo. The residue can be purified by chromatography on silica gel using a gradient of pure methylene chloride to 50% acetone in methylene chloride to yield pure 1-(4-chlorophenylamino)-4-(4-pyridylthio)phthalazine. The intermediate thioether can be stirred as a solution in acetic acid as 30% aqueous hydrogen peroxide is added in small portions until TLC analysis indicates that all starting material has been consumed. The crude product is isolated by dilution with ethyl acetate, washing with aqueous carbonate solution to remove acetic acid and evaporation in vacuo. Pure invention compound can be obtained by chromatography on the residue on silica gel using methylene chloride/acetone gradients.

EXAMPLE 20

Preparation of 1-(4-chlorophenylamino)-4-(4-pyridylsufinyl)phthalazine

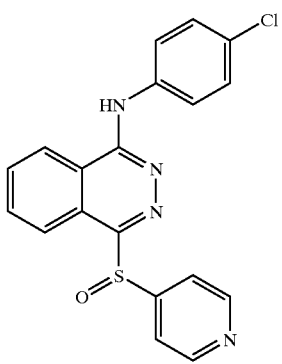

Following the general procedure of Proudfoot, et al. (*J. Org. Chem.* 58, 6996–700, 1993), 1-(4-chlorophenylamino)-4-(4-pyridylthio)phthalazine from example 19 can be stirred with one equivalent of sodium periodate in methanol/water for several days at room temperature to yield the title compound which can be isolated in pure form by chromatography on silica gel using methylene chloride/methanol gradients.

EXAMPLE 21

Preparation of 1-(4-chlorophenylamino)-4-(4-pyridylmethoxy)pyridazine

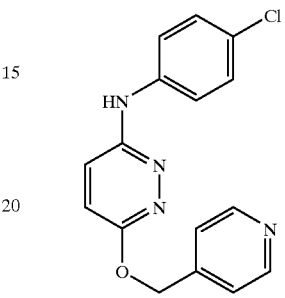

Step 1: To a mixture of 3,6-dibromo-pyridazine (500 mg, 2.10 mmol, for preparation see Pwdrali et al.; J. Org. Chem.; 23, 1958; 778) and 4-pyridylcarbinol (229 mg. 2.10 mmol) in anhydrous tetrahydronfuran (10 mL) at 0° C. under argon was added sodium hydride (302 mg, 12.6 mmol). The reaction mixture was warmed up to RT and then was stirred at 50° C. under argon for 6 h. After cooled to 0° C., the resultant orange mixture was diluted with ethyl acetate (20 mL) and then excess sodium hydride was quenched by water until no bubble occurred. The organic layer was collected and washed by brine (3×10 mL) and dried over anhydrous $Na_2SO_4$, filtered, and evaporated in vacuo, which afforded 400 mg (1.50 mmol, 71% yield) of 1-bromo-4-(4-pyridylmethoxy)pyridazine as an oil. The crude product was pure enough to carried out next step reaction without further purification. $^1$H-NMR (MeOH-$d_4$) 8.52–8.54 (m, 2H), 7.80 (d, 1H), 7.52–7.54 (m, 2H), 7.25 (d, 1H), 5.60 (s, 2H); MS LC 266 M+, 269 (M+3H)$^+$, cacl. 266; TLC (3:2 v/v ethyl acetate-hexanes) $R_f$=0.20.

Step 2: To 1-bromo-4-(4-pyridylmethoxy)pyridazine (50 mg, 0.19 mmol) in toluene (3 mL) was added 4-chloroaniline (29 mg, 0.22 mmol), catalytical amount of (R)-(+)2,2'-bis(diphenyl phosphino)-1,1'-binaphthyl (1 mg), tris(dibenzylideneacetone)-dipalladium(0) (0.6 mg) and sodium t-butyloxide (26 mg, 0.27 mmol). The reaction mixture was heated at 80° C. for 12 h under argon. The reaction mixture became deep brown upon heating. The mixture was cooled to RT, diluted with ethyl acetate (10 mL), washed by brine and the organic layer was dried over Na2SO4, and the solvent was evaporated in vacuo. The crude mixture was purified by preparative thin layer plate to afford the title compound (6 mg, yield 10%). 1H-NMR (MeOH-$_4$), 8.51 (d, 2H), 7.61(d, 2H) 7.52(dd, 2H), 7.15–7.25(m, 4H), 5.49(s, 2H); MS ES 313 (M+H)$^+$, 315 (M+3H)$^+$, 316 (M+4H)$^+$, calc. 312; TLC (5:95 v/v methanol-methylene chloride) $R_f$=0.2.

EXAMPLE 22

Preparation of 1-(indan-5-ylamino)-4-(4-pyridylcyanomethyl)phthalazine

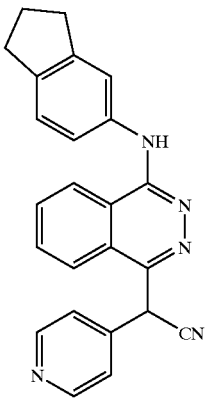

Step 1: 4-Pyridylacetonitrile hydrochloride (5.00 g, 32.3 mmol) in 40 mL of THF was sonicated for 10 min, and the mixture was added to 10 mL THF solution of NaH (1.55 g, 64.7 mmol) using dripping funnel while the temperature was kept below 15° C. After the addition, the mixture was cooled to 0° C. and 1,4-dichlorophthalazine (3.22 g, 24.3 mmol) was added to the mixture. The mixture turned into red instantly. The reaction was continued for another 4 hrs, and the mixture was poured in cold $NH_4Cl$ solution. The resulting red solid was filtered, washed with $H_2O$, and dried to give 4.4 g of 1-chloro-4-(4-pyridylcyanomethyl)phthalazine (65%); mp 265° C. (dec); $^1H$ NMR ($CDCl_3$) δ 6.00 (s, 1H), 7.39–8.60 (m, 8H); LC/MS $MH^+$281.4.

Step 2: A mixture of 1-chloro-4-(4-pyridylcyanomethyl)phthalazine (570 mg, 2.03 mmol) and 5-aminoindan (320 mg, 2.40 mmol) in 20 mL of n-butanol were refluxed for 10 hrs. The solvent was evaporated under reduced pressure and the solid was dissolved in 50 mL of dichloromethane and washed with 4 M KOH solution and $H_2O$. The organic layer was separated and dried ($MgSO_4$). The product (420 mg, 55%) was purified by prep TLC on silicon gel using EtOAc/MeOH (20:1) as the eluent. $R_f$ 0.7; mp 122–123° C.; $^1H$ NMR ($CD_3OD$) δ 2.15 (m, 2H), 2.85 (m, 4H), 7.20–8.60 (m, 12H); LC/MS $MH^+$378.4.

EXAMPLE 23

Preparation of 1-(benzothiazol-6-ylamino)-4-(4-pyridylcyanomethyl)phthalazine

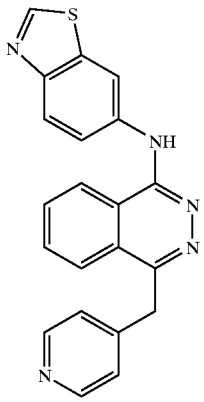

The procedure used for the preparation of Example 22 was used to prepare the title compound by substituting 6-aminobenzothiazole (360 mg, 2.40 mmol) for 5-aminoindan and 1-chloro-4-(4-pyridylmethyl)phthalazine (for preparation see Novartis patent WO98/35958, 11.02.98, 520 mg, 2.03 mmol) for 1-chloro-4-(4-pyridylcyanomethyl) phthalazine. Pure product had the characteristics: mp 163-164° C.; $R_f$ 0.6 (EtOAc:MeOH=20:1); $^1H$ NMR ($CD_3OD$) δ 4.65 (s, 2H), 7.38 (s, 2H), 7.96 (m, 5H), 8.40 (s, 2H), 8.49 (m, 2H), 8.82 (s, 2H), 9.11 (s, 2H); LC/MS $MH^+$370.4.

Biological Protocols and in vitro Test Data

KDR Assay:

The cytosolic kinase domain of KDR kinase was expressed as a 6 His fusion protein in Sf9 insect cells. The KDR kinase domain fusion protein was purified over a Ni++chelating column. Ninety-six well ELISA plates were coated with 5 μg poly(Glu4;Tyr1) (Sigma Chemical Co., St Louis, Mo.) in 100 μl HEPES buffer (20 mM HEPES, pH 7.5, 150 mM NaCl, 0.02% Thimerosal) at 4° overnight. Before use, the plate was washed with HEPES, NaCl buffer and the plates were blocked with 1% BSA, 0.1% Tween 20 in HEPES, NaCl buffer.

Test compounds were serially diluted in 100% DMSO from 4 mM to 0.12 μM in half-log dilutions. These dilutions were further diluted twenty fold in H2O to obtain compound solutions in 5% DMSO. Following loading of the assay plate with 85 μl of assay buffer (20 mM HEPES, pH 7.5, 100 mM KCl, 10 mM $MgCl_2$, 3 mM $MnCl_2$, 0.05% glycerol, 0.005% Triton X-100, 1 mM-mercaptoethanol, with or without 3.3 μM ATP), 5 μl of the diluted compounds were added to a final assay volume of 100 μl. Final concentrations were between 10 μM, and 0.3 nM in 0.25% DMSO. The assay was initiated by the addition of 10 μl (30 ng) of KDR kinase domain.

The assay was incubated with test compound or vehicle alone with gentle agitation at room temperature for 60 minutes. The wells were washed and phosphotyrosines (PY) were probed with an anti-phosphotyrosine (PY), mAb clone 4G10 (Upstate Biotechnology, Lake Placid, N.Y.). PY/anti-PY complexes were detected with an anti-mouse IgG/HRP conjugate (Amershamn International plc, Buckinghamshire, England). Phosphotyrosine was quantitated by incubating with 100 μl 3, 3', 5, 5' tetramethylbenzidine solution (Kirkegaard and Perry, TMB Microwell 1 Component peroxidase substrate). Color development was arrested by the addition of 100 μl 1% HCl-based stop solution (Kirkegaard and Perry, TMB 1 Component Stop Solution).

Optical densities were determined spectrophotometrically at 450 nm in a 96-well plate reader, SpectraMax 250 (Molecular Devices). Background (no ATP in assay) OD values were subtracted from all ODs and the percent inhibition was calculated according to the equation:

$$\% \text{ Inhibition} = \frac{(OD(\text{vehicle control}) - OD(\text{with compound})) \times 100}{OD(\text{vehicle control}) - OD(\text{no } ATP \text{ added})}$$

The $IC_{50}$ values were determined with a least squares analysis program using compound concentration versus percent inhibition. Compounds that have $IC_{50}$<100 nM in this assay include those of Examples 1, 2, 4, 5, 6, 7, 10, 11, 12, 13, 14, 15, 16 and 23. Compounds that have $IC_{50}$ values between 100 nM and 1,000 nM include those of examples 8, 9 and 22. Those that have measured $IC_{50}$ values>1,000 nM include those of examples 3, 17, 18 and 21.

Cell mechanistic assay-Inhibition of 3T3 KDR phosphorylation:

NIH3T3 cells expressing the full length KDR receptor were grown in DMEM (Life Technologies, Inc., Grand Island, N.Y.) supplemented with 10% newborn calf serum, low glucose, 25 mM/L sodium pyruvate, pyridoxine hydrochloride and 0.2 mg/ml of G418 (Life Technologies Inc., Grand Island, N.Y.). The cells were maintained in collagen I-coated T75 flasks (Becton Dickinson Labware, Bedford, Mass.) in a humidified 5% CO2 atmosphere at 37° C.

Fifteen thousand cells were plated into each well of a collagen I-coated 96-well plate in the DMEM growth medium. Six hours later, the cells were washed and the medium was replaced with DMEM without serum. After overnight culture to quiesce the cells, the medium was replaced by Dulbecco's phosphate-buffered saline (Life Technologies Inc., Grand Island, N.Y.) with 0.1% bovine albumin (Sigma Chemical Co., St Louis, Mo.). After adding various concentrations (0–300 nM) of test compounds to the cells in 1% final concentration of DMSO, the cells were incubated at room temperature for 30 minutes. The cells were then treated with VEGF (30 ng/ml) for 10 minutes at room temperature. Following VEGF stimulation, the buffer was removed and the cells were lysed by addition of 150 $\mu$l of extraction buffer (50 mM Tris, pH 7.8, supplemented with 10% glycerol, 50 mM BGP, 2 mM EDTA, 10 mM NaF, 0.5 mM NaVO4, and 0.3% TX-i00) at 4° C. for 30 minutes.

To assess receptor phosphorylation, 100 microliters of each cell lysate was added to the wells of an ELISA plate precoated with 300 ng of antibody C20 (Santa Cruz Biotechnology, Inc., Santa Cruz, Calif.). Following a 60-minute incubation, the plate was washed and bound KDR was probed for phosphotyrosine using an anti-phosphotyrosine mAb clone 4G10 (Upstate Biotechnology, Lake Placid, N.Y.). The plate was washed and wells were incubated with anti-mouse IgG/HRP conjugate (Amersham International plc, Buckinghamshire, England) for 60 minutes. Wells were washed and phosphotyrosine was quantitated by addtion of 100 $\mu$l per well of 3,3',5,5' tetramethylbenzidine (Kirkegaard and Perry, TMB Microwell 1 Component peroxidase substrate) solution. Color development was arrested by the addition of 100 $\mu$l 1% HCl based stop solution (Kirkegaard and Perry, TMB 1 Component Stop Solution).

Optical densities (OD) were determined spectrophotometrically at 450 nm in a 96-well plate reader (SpectraMax 250, Molecular Devices). Background (no VEGF added) OD values were subtracted from all ODs and percent inhibition was calculated according to the equation:

$$\% \text{ Inhibition} = \frac{(OD(VEGF \text{ control}) - OD(\text{with test compound})) \times 100}{OD(VEGF \text{ control}) - OD(\text{no VEGF added})}$$

IC50s were determined with a least squares analysis program using compound concentration versus percent inhibition. Compounds that have $IC_{50}$<20 nM in this assay include those of Examples 2, 6, 7, 11, 15 and 16. Compounds that have $IC_{50}$ values between 20 nM and 50 nM include those of examples 1, 4, 5, 8, 10, 12, 13 and 14. Those that have measured $IC_{50}$ values>50 nM include those of examples 9 and 21.

Matrigel® Angiogenesis Model:

Preparation of Matrigel Plugs and in vivo Phase: Matrigel® (Collaborative Biomedical Products, Bedford, Mass.) is a basement membrane extract from a murine tumor composed primarily of laminin, collagen IV and heparan sulfate proteoglycan. It is provided as a sterile liquid at 4° C., but rapidly forms a solid gel at 37° C.

Liquid Matrigel at 4° C. was mixed with SK-MEL2 human tumor cells that were transfected with a plasmid containing the murine VEGF gene with a selectable marker. Tumor cells were grown in vitro under selection and cells were mixed with cold liquid Matrigel at a ratio of $2 \times 10^6$ per 0.5 ml. One half milliliter was implanted subcutaneously near the abdominal midline using a 25 gauge needle. Test compounds were dosed as solutions in Ethanol/Cremaphor EL/saline (12.5%:12.5%:75%) at 30, 100, and 300 mg/kg po once daily starting on the day of implantation. Mice were euthanized 12 days post-implantation and the Matrigel pellets were harvested for analysis of hemoglobin content.

Hemoglobin Assay: The Matrigel pellets were placed in 4 volumes (w/v) of 4° C. Lysis Buffer (20 mM Tris pH 7.5, 1 mM EGTA, 1 mM EDTA, 1% Triton X-100 [EM Science, Gibbstown, N.J.], and complete, EDTA-free protease inhibitor cocktail [Mannheim, Germany]), and homogenized at 4° C. Homogenates were incubated on ice for 30 minutes with shaking and centrifuged at 14K×g for 30 minutes at 4° C. Supernatants were transferred to chilled microfuge tubes and stored at 4° C. for hemoglobin assay.

Mouse hemoglobin (Sigma Chemical Co., St. Louis, Mo.) was suspended in autoclaved water (BioWhittaker, Inc, Walkersville, Md.) at 5 mg/ml. A standard curve was generated from 500 micrograms/ml to 30 micrograms/ml in Lysis Buffer (see above). Standard curve and lysate samples were added at 5 microliters/well in duplicate to a polystyrene 96-well plate. Using the Sigma Plasma Hemoglobin Kit (Sigma Chemical Co., St Louis, Mo.), TMB substrate was reconstituted in 50 mls room temperature acetic acid solution. One hundred microliters of substrate was added to each well, followed by 100 microliters/well of Hydrogen Peroxide Solution at room temperature. The plate was incubated at room temperature for 10 minutes.

Optical densities were determined spectrophotometrically at 600 nm in a 96-well plate reader, SpectraMax 250 Microplate Spectrophotometer System (Molecular Devices, Sunnyvale, Calif.). Background Lysis Buffer readings were subtracted from all wells.

Total sample hemoglobin content was calculated according to the following equation:

$$\text{Total Hemoglobin} = (\text{Sample Lysate Volume}) \times (\text{Hemoglobin Concentration})$$

The average Total Hemoglobin of Matrigel samples without cells was subtracted from each Total Hemoglobin Matrigel sample with cells. Percent inhibition was calculated according to the following equation:

$$\% \text{ Inhibition} = \frac{(\text{Average Total Hemoglobin Drug-Treated Tumor Lysates}) \times 100}{(\text{Average Total Hemoglobin Non-Treated Tumor Lysates})}$$

Both examples 1 and 2 showed significant activity in this assay at 30, 100 and 300 mg/kg po sid with >50% inhibition of total hemoglobin content of the Matrigel samples from the dosed animals vs. those from vehicle control animals.

Other embodiments of the invention will be apparent the skilled in the art from a consideration of this specification or practice of the invention disclosed herein. It is intended that the specification and examples be considered as exemplary only, with the true scope and spirit of the invention being indicated by the following claims.

We claim:
1. A compound having the structural formula

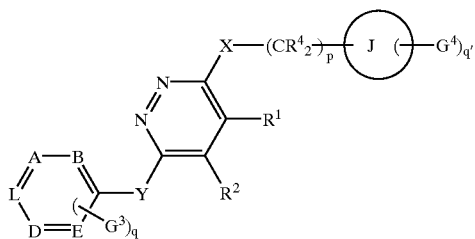

wherein
R¹ and R²:
together form a bridge of structure

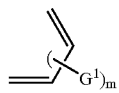

wherein bonding is achieved via the terminal carbon atoms; and
wherein
m is 0 or an integer 1–4; and
G¹ is a substituent independently selected from the group consisting of
—N(R⁶)₂;
—NR³COR⁶;
halogen;
alkyl;
cycloalkyl;
lower alkenyl;
lower cycloalkenyl;
halogen-substituted alkyl;
amino-substituted alkyl;
N-lower alkylamino-substituted alkyl;
N,N-di-lower alkylamino-substituted alkyl;
N-lower alkanoylamino-substituted alkyl;
hydroxy-substituted alkyl;
cyano-substituted alkyl;
carboxy-substituted alkyl;
lower alkoxycarbonyl-substituted alkyl;
phenyl lower alkoxycarbonyl-substituted alkyl;
halogen-substituted alkylamino;
amino-substituted alkylamino;
N-lower alkylamino-substituted alkylamino;
N,N-di-lower alkylamino-substituted alkylamino;
N-lower alkanoylamino-substituted alkylamino;
hydroxy-substituted alkylamino;
cyano-substituted alkylamino;
carboxy-substituted alkylamino;
lower alkoxycarbonyl-substituted alkylamino;
phenyl-lower alkoxycarbonyl-substituted alkylamino;
—OR⁶;
—SR⁶;
—S(O)R⁶;
—S(O)₂R⁶;
halogenated lower alkoxy;
halogenated lower alkythio;
halogenated lower alkylsulfonyl;
—OCOR⁶;
—COR⁶;
—CO₂R⁶;
—CON(R⁶)₂;
—CH₂OR³;
—NO₂;
—CN;
amidino;
guanidino;
sulfo;
—B(OH)₂;
optionally substituted aryl;
optionally substituted heteroaryl;
optionally substituted saturated heterocyclyl;
optionally substituted partially unsaturated heterocyclyl;
—OCO₂R³;
optionally substituted heteroarylalkyl;
optionally substituted heteroaryloxy;
—S(O)ₚ(optionally substituted heteroaryl);
optionally substituted heteroarylalkyloxy;
—S(O)ₚ(optionally substituted heteroarylalkyl);
—CHO;
—OCON(R⁶)₂;
—NR³CO₂R⁶; and
—NR³CON(R⁶)₂;
R³ is H or lower alkyl;
R⁶ is independently selected from the group consisting of
H;
alkyl;
optionally substituted aryl;
optionally substituted aryl lower alkyl; and
R⁴ is H, halogen, or lower alkyl;
p is 0, 1, or 2;
X is selected from the group consisting of O, S, and NH;
Y is selected from the group consisting of
—(CR₂⁴)ₙ—S(O)ₚ-(5-membered heteroaryl)—(CR₂⁴)ₛ—;
—(CR₂⁴)ₙ—C(G²)(R⁴)—(CR₂⁴)ₛ—;
wherein
n and s are each independently 0 or an integer of 1–2; and
G² is selected from the group consisting of —CN, —CO₂R³, —CON(R⁶)₂; and —CH₂N(R⁶)₂;
—O—CH₂—;
—S(O)—;
—S(O₂)—;
—SCH₂—;
—S(O)CH₂—;
—S(O)₂CH₂—;
—CH₂S(O)—; and
—CH₂S(O)₂—;
A and D independently represent N or CH;
B and E independently represent N or CH;
L represents N or CH;
with the provisos that
a) the total number of N atoms in the ring containing A, B, D, E, and L is 1 or 2; and b) when L represents CH, at least one of A and D is an N atom;
q is 0, 1, or 2;
$G^3$ is selected from the group consisting of
  lower alkyl;
  —$NR^3COR^6$;
  carboxy-substituted alkyl;
  lower alkoxycarbonyl-substituted alkyl;
  —$OR^6$;
  —$SR^6$;
  —$S(O)R^6$;
  —$S(O)_2R^6$;
  —$OCOR^6$;
  —$COR^6$;
  —$CO_2R^6$;
  —$CH_2OR^3$;
  —$CON(R^6)_2$;
  —$S(O)_2N(R^6)_2$;
  —$NO_2$;
  —CN;
  optionally substituted aryl;
  optionally substituted heteroaryl;
  optionally substituted saturated heterocyclyl;
  optionally substituted partially unsaturated heterocyclyl;
  optionally substituted heteroarylalkyl;
  optionally substituted heteroaryloxy;
  —$S(O)_p$(optionally substituted heteroaryl);
  optionally substituted heteroarylalkyloxy;
  —$S(O)_p$(optionally substituted heteroarylalkyl);
  —$OCON(R^6)_2$;
  —$NR^3CO_2R^6$; and
  —$NR^3CON(R^6)_2$;
J is a ring selected from the group consisting of
  aryl;
  pyridyl; and
  cycloalkyl;
q' represents the number of substituents $G^4$ on ring J and is 0, 1, 2, 3, 4, or 5; and
$G^4$ moieties are selected from the group consisting of
  —$N(R^6)_2$;
  —$NR^3COR^6$;
  halogen;
  alkyl;
  cycloalkyl;
  lower alkenyl;
  lower cycloalkenyl;
  halogen-substituted alkyl;
  amino-substituted alkyl;
  N-lower alkylamino-substituted alkyl;
  N,N-di-lower alkylamino-substituted alkyl;
  N-lower alkanoylamino-substituted alkyl;
  hydroxy-substituted alkyl;
  cyano-substituted alkyl;
  carboxy-substituted alkyl;
  lower alkoxycarbonyl-substituted alkyl;
  phenyl lower alkoxycarbonyl-substituted alkyl;
  halogen-substituted alkylamino;
  amino-substituted alkylamino;
  N-lower alkylamino-substituted alkylamino;
  N,N-di-lower alkylamino-substituted alkylamino;
  N-lower alkanoylamino-substituted alkylamino;
  hydroxy-substituted alkylamino;
  cyano-substituted alkylamino;
  carboxy-substituted alkylamino;
  lower alkoxycarbonyl-substituted alkylamino;
  phenyl-lower alkoxycarbonyl-substituted alkylamino;
  —$OR^6$;
  —$SR^6$;
  —$S(O)R^6$;
  —$S(O)_2R^6$;
  halogenated lower alkoxy;
  halogenated lower alkylthio;
  halogenated lower alkylsulfonyl;
  —$OCOR^6$;
  —$COR^6$;
  —$CO_2R^6$;
  —$CON(R^6)_2$;
  —$CH_2OR^3$;
  —$NO_2$;
  —CN;
  amidino;
  guanidino;
  sulfo;
  —$B(OH)_2$;
  optionally substituted aryl;
  optionally substituted heteroaryl;
  optionally substituted saturated heterocyclyl;
  optionally substituted partially unsaturated heterocyclyl;
  —$OCO_2R^3$;
  optionally substituted heteroarylalkyl;
  optionally substituted heteroaryloxy;
  —$S(O)_p$(optionally substituted heteroaryl);
  optionally substituted heteroarylalkyloxy;
  —$S(O)_p$(optionally substituted heteroarylalkyl);
  —CHO;
  —$OCON(R^6)_2$;
  —$NR^3CO_2R^6$;
  —$NR^3CON(R^6)_2$; and
  fused ring-forming bridges attached to and connecting adjacent positions of ring J, said bridges having the structures:
  a)

$$T^2 \!\!\!\diagdown\!\!\!\diagdown\, T^2 \diagup T^3$$

wherein
  each $T^2$ independently represents N, CH, or $CG^4$;
  $T^3$ represents S, O, $CR^4G^4$, $C(R^4)_2$, or $NR^3$; and
  bonding to ring J is achieved via terminal atoms $T^2$ and $T^3$;

b)

wherein each $T^2$ independently represents N, CH, or $CG^4$;

with the proviso that a maximum of two bridge atoms $T^2$ may be N; and bonding to ring J is achieved via terminal atoms $T^2$; and c)

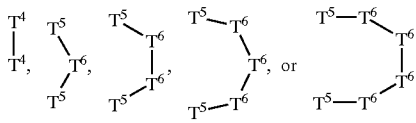

wherein each $T^4$, $T^5$, and $T^6$ independently represents O, S, $CR^4G^4$, $C(R^4)_2$, or $NR^3$; and bonding to ring J is achieved via terminal atoms $T^4$ or $T^5$;

with the provisos that:

i) when one $T^4$ is O, S, or $NR^3$, the other $T^4$ is $CR^4G^4$ or $C(R^4)_2$;

ii) a bridge comprising $T^5$ and $T^6$ atoms may contain a maximum of two heteroatoms O, S, or N; and iii) in a bridge comprising $T^5$ and $T^6$ atoms, when one $T^5$ group and one $T^6$ group are O atoms, or two $T^6$ groups are O atoms, said O atoms are separated by at least one carbon atom;

and with the further provisos that:

in $G^1$, $G^2$, $G^3$, and $G^4$, when two groups $R^6$ are each alkyl and located on the same N atom they may be linked by a bond, an O, an S, or $NR^3$ to form a heterocycle of 5–7 ring atoms; and when an aryl, heteroaryl, or heterocyclyl ring is optionally substituted, that ring may bear up to 5 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —$CO_2R^3$, —CHO, —$CH_2OR^3$, —$OCO_2R^3$, —$CON(R^6)_2$, —OCO $N(R^6)_2$, —$NR^3CON(R^6)_2$, nitro, amidino, guanidino, mercapto, sulfo, and cyano;

or a pharmaceutically acceptable salt thereof.

2. A compound having the structural formula

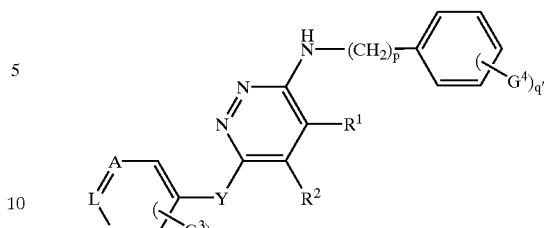

wherein $R^1$ and $R^2$:

together form a bridge of structure

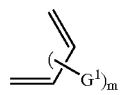

wherein bonding is achieved via the terminal carbon atoms;

wherein m is 0 or an integer 1–2; and $G^1$ is a substituent independently selected from the group consisting of

—$N(R^6)_2$;

—$NR^3COR^6$;

halogen;

alkyl;

amino-substituted alkylamino;

N-lower alkylamino-substituted alkylamino;

N,N-di-lower alkylamino-substituted alkylamino;

N-lower alkanoylamino-substituted alkylamino;

hydroxy-substituted alkylamino;

carboxy-substituted alkylamino;

lower alkoxycarbonyl-substituted alkylamino;

—$OR^6$;

—$SR^6$;

—$S(O)R^6$;

—$S(O)_2R^6$;

halogenated lower alkoxy;

halogenated lower alkylthio;

halogenated lower alkylsulfonyl;

—$OCOR^6$;

—$COR^6$;

—$CO_2R^6$;

—$CON(R^6)_2$;

—$NO_2$;

—CN;

optionally substituted heteroarylalkyl;

optionally substituted heteroaryloxy;

—$S(O)_p$(optionally substituted heteroaryl);

optionally substituted heteroarylalkyloxy; and

—$S(O)_p$(optionally substituted heteroarylalkyl);

$R^3$ is H or lower alkyl;

$R^6$ is independently selected from the group consisting of
H;
lower alkyl;
optionally substituted aryl;
optionally substituted aryl lower alkyl; and
p is 0 or 1;
Y is selected from the group consisting of
—$(CH_2)_n$—$S(O)_p$—(5-membered heteroaryl)—$(CH_2)_s$—;
—$(CH_2)_n$—$C(G^2)(H)$—$(CH_2)_s$—;
wherein
n and s are each independently 0 or 1; and
$G^2$ is selected from the group consisting of —CN, —$CO_2R^3$, —$CON(R^6)_2$, and —$CH_2N(R^6)_2$;
—O—$CH_2$—;
—S(O);
—$S(O)_2$—;
—$SCH_2$—;
—$S(O)CH_2$—;
—$S(O)_2CH_2$—;
—$CH_2S(O)$—; and
—$CH_2S(O)_2$—;
A and D independently represent N or CH;
L represents N or CH;
with the provisos that
a) the total number of N atoms in the ring containing A, D, and L is 1 or 2; and
b) when L represents CH, at least one of A and D is an N atom;
q is 0, 1, or 2;
$G^3$ is selected from the group consisting of
lower alkyl;
—$NR^3COR^6$;
—$OR^6$;
—SR;
—$S(O)R^6$;
—$S(O)_2R^6$;
—$CO_2R^6$;
—$CON(R^6)_2$;
—$S(O)_2N(R^6)_2$;
—CN;
optionally substituted aryl;
optionally substituted heteroaryl;
optionally substituted heteroarylalkyl;
optionally substituted heteroaryloxy,
—$S(O)_p$(optionally substituted heteroaryl);
optionally substituted heteroarylalkyloxy, and
—$S(O)_p$(optionally substituted heteroarylalkyl);
q' represents the number of substituents $G^4$ on the phenyl ring and is 0, 1, 2, or 3; and
$G^4$ moieties are selected from the group consisting of
—$N(R^6)_2$;
—$NR^3COR^6$;
halogen;
alkyl;
halogen-substituted alkyl;
hydroxy-substituted alkyl;
carboxy-substituted alkyl;
lower alkoxycarbonyl-substituted alkyl;
amino-substituted alkylamino;
N-lower alkylamino-substituted alkylamino;
N,N-di-lower alkylamino-substituted alkylamino;
N-lower alkanoylamino-substituted alkylamino;
hydroxy-substituted alkylamino;
carboxy-substituted alkylamino;
lower alkoxycarbonyl-substituted alkylamino;
phenyl-lower alkoxycarbonyl-substituted alkylamino;
—$OR^6$;
—$SR^6$;
—$S(O)R^6$;
—$S(O)_2R^6$;
halogenated lower alkoxy;
halogenated lower alkylthio;
halogenated lower alkylsulfonyl;
—$OCOR^6$;
—$COR^6$;
—$CO_2R^6$;
—$CON(R^6)_2$;
—$CH_2OR^3$;
—$NO_2$;
—CN;
optionally substituted heteroarylalkyl;
optionally substituted heteroaryloxy;
—$S(O)_p$(optionally substituted heteroaryl);
optionally substituted heteroarylalkyloxy;
—$S(O)_p$(optionally substituted heteroarylalkyl); and
fused ring-forming bridges attached to and connecting adjacent positions of the phenyl ring, said bridges having the structures:
a)

wherein
each $T^2$ independently represents N, CH, or $CG^4$;
$T^3$ represents S, O, $CHG^4$, $CH_2$, or $NR^3$; and
bonding to the phenyl ring is achieved via terminal atoms $T^2$ and $T^3$;
b)

wherein
each $T^2$ independently represents N, CH, or $CG^4$;
with the proviso that a maximum of two bridge atoms $T^2$ may be N; and
bonding to the phenyl ring is achieved via terminal atoms $T^2$; and c)

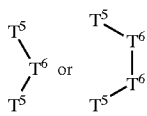

wherein
each $T^5$, and $T^6$ independently represents O, S, $CHG^4$, $CH_2$, or $NR^3$; and
bonding to the phenyl ring is achieved via terminal atoms $T^5$;
with the provisos that:
  i) a bridge comprising $T^5$ and $T^6$ atoms may contain a maximum of two heteroatoms O, S, or N; and
  ii) in a bridge comprising $T^5$ and $T^6$ atoms, when one $T^5$ group and one $T^6$ group are O atoms, or two $T^6$ groups are O atoms, said O atoms are separated by at least one carbon atom;
and with the further provisos that:
  in $G^1$, $G^2$, $G^3$, and $G^4$, when two groups $R^6$ are each alkyl and located on the same N atom they may be linked by a bond, an O, an S, or $NR^3$ to form a heterocycle of 5–7 ring atoms; and
  when an aryl, heteroaryl, or heterocyclyl ring is optionally substituted, that ring may bear up to 2 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, $-CO_2R^3$, $-CH_2OR^3$, $-OCO_2R^3$, $-CON(R^6)_2$, $-OCON(R^6)_2$, $-NR^3CON(R^6)_2$, nitro, and cyano;
or a pharmaceutically acceptable salt thereof.

3. A compound having the structural formula

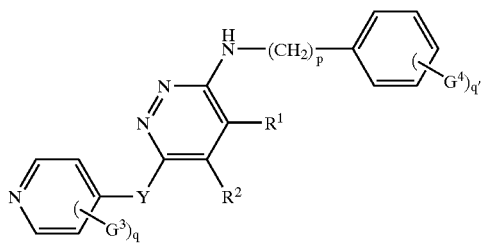

wherein
$R^1$ and $R^2$:
together form a bridge of structure

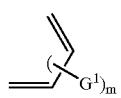

wherein bonding is achieved via the terminal carbon atoms, and any group $G^1$ is located on a non-terminal atom of the bridge;
wherein
m is 0 or an integer 1–2; and
$G^1$ is a substituent independently selected from the group consisting of
$-N(R^6)_2$;
$-NR^3COR^6$;
halogen;
$-OR^6$ wherein $R^6$ represents lower alkyl;
$-NO_2$;
optionally substituted heteroaryloxy; and
optionally substituted heteroarylalkyloxy;
$R^3$ is H or lower alkyl;
$R^6$ independently selected from the group consisting of
H;
lower alkyl;
optionally substituted aryl;
optionally substituted aryl lower alkyl; and
p is 0 or 1;
Y is selected from the group consisting of
$-S(O)_p-$(5-membered heteroaryl)$-$;
$-C(CN)(H)-$;
$-O-CH_2-$;
$-S(O)-$; and
$-S(O)_2$;
q is 0 or 1;
$G^3$ is selected from the group consisting of
lower alkyl;
$-NR^6COR^6$;
$-CO_2R^6$;
$-CON(R^6)_2$; and
$-S(O)_2N(R^6)_2$;
q' represents the number of substituents $G^4$ on the phenyl ring and is 0, 1, 2, or 3; and
$G^4$ moieties are selected from the group consisting of
$-N(R^6)_2$;
halogen;
lower alkyl;
halogen-substituted lower alkyl;
$-OR^6$;
$-SR^6$;
$-S(O)R^6$;
$-S(O)_2R^6$;
halogenated lower alkoxy;
halogenated lower alkylthio;
halogenated lower alkylsulfonyl;
$-OCOR^6$;
$-COR^6$;
$-CO_2R^6$;
$-CON(R^6)_2$;
$-CH_2OR^3$;
$-NO_2$;
$-CN$;
optionally substituted heteroarylalkyl;
optionally substituted heteroaryloxy;
$-S(O)_p$(optionally substituted heteroaryl);
optionally substituted heteroarylalkyloxy;

—S(O)$_p$(optionally substituted heteroarylalkyl); and fused ring-forming bridges attached to and connecting adjacent positions of the phenyl ring, said bridges having the structures:

a)

$$\begin{array}{c} T^2 \\ \parallel \\ T^2 \\ / \\ T^3 \end{array}$$

wherein
each T$^2$ independently represents N, CH, or CG$^4$;
T$^3$ represents S, O, CHG$^4$, CH$_2$, or NR$^3$; and
bonding to the phenyl ring is achieved via terminal atoms T$^2$ and T$^3$;

b)

$$\begin{array}{cc} T^5 & T^5 \\ \backslash & \backslash \\ T^6 \quad \text{or} \quad T^6 \\ / & | \\ T^5 & T^5{-}T^6 \end{array}$$

wherein
each T$^5$, and T$^6$ independently represents O, S, CHG$^4$, CH$_2$, or NR$^3$; and
bonding to the phenyl ring is achieved via terminal atoms T$^5$;
with the provisos that:
i) a bridge comprising T$^5$ and T$^6$ atoms may contain a maximum of two heteroatoms O, S, or N; and
ii) in a bridge comprising T$^5$ and T$^6$ atoms, when one T$^5$ group and one T$^6$ group are O atoms, or two T$^6$ groups are O atoms, said O atoms are separated by at least one carbon atom;

and with the further provisos that:
in G$^1$, G$^2$, G$^3$, and G$^4$, when two groups R$^6$ are each alkyl and located on the same N atom they may be linked by a bond, an O, an S, or NR$^3$ to form a heterocycle of 5–6 ring atoms; and when an aryl, heteroaryl, or heterocyclyl ring is optionally substituted, that ring may bear up to 2 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, —CO$_2$R$^3$, —CON(R$^6$)$_2$, nitro, and cyano;

or a pharmaceutically acceptable salt thereof.

4. A pharmaceutical composition comprising a compound of claim 1 and a pharmaceutically acceptable carrier.

5. A method of treating a mammal having a condition of tumor growth, retinopathy, rheumatoid arthritis, psoriasis, or a bullous disorder associated with subepidermal blister formation, comprising administering to said mammal an amount of a compound of claim 1 which is effective to treat said condition.

6. A compound having the structural formula wherein
R$^1$ and R$^2$:
together form a bridge of structure wherein bonding is achieved via the terminal carbon atoms;
wherein
m is 0 or an integer 1–4; and
G$^1$ is a substituent independently selected from the group consisting of
—N(R$^6$)$_2$;
—NR$^3$COR$^6$;
halogen;
alkyl;
cycloalkyl;
lower alkenyl;
lower cycloalkenyl;
halogen-substituted alkyl;
amino-substituted alkyl;
N-lower alkylamino-substituted alkyl;
N,N-di-lower alkylamino-substituted alkyl;
N-lower alkanoylamino-substituted alkyl;
hydroxy-substituted alkyl;
cyano-substituted alkyl;
carboxy-substituted alkyl;
lower alkoxycarbonyl-substituted alkyl;
phenyl lower alkoxycarbonyl-substituted alkyl;
halogen-substituted alkylamino;
amino-substituted alkylamino;
N-lower alkylamino-substituted alkylamino;
N,N-di-lower alkylamino-substituted alkylamino;
N-lower alkanoylamino-substituted alkylamino;
hydroxy-substituted alkylamino;
cyano-substituted alkylamino;
carboxy-substituted alkylamino;
lower alkoxycarbonyl-substituted alkylamino;
phenyl-lower alkoxycarbonyl-substituted alkylamino;
—OR$^6$;
—SR$^6$;
—S(O)R$^6$;
—S(O)$_2$R$^6$;

halogenated lower alkoxy;
halogenated lower alkylthio;
halogenated lower alkylsulfonyl;
—OCOR⁶;
—COR⁶;
—CO₂R⁶;
—CON(R⁶)₂;
—CH₂OR³;
—NO₂;
—CN;
amidino;
guanidino;
sulfo;
—B(OH)₂;
optionally substituted aryl;
optionally substituted heteroaryl;
optionally substituted saturated heterocyclyl;
optionally substituted partially unsaturated heterocyclyl;
—OCO₂R³;
optionally substituted heteroarylalkyl;
optionally substituted heteroaryloxy;
—S(O)$_p$(optionally substituted heteroaryl);
optionally substituted heteroarylalkyloxy;
—S(O)$_p$(optionally substituted heteroarylalkyl);
—CHO;
—OCON(R⁶)₂;
—NR³CO₂R⁶; and
—NR³CON(R⁶)₂ ;
R³ is H or lower alkyl;
R⁶ is independently selected from the group consisting of
H;
alkyl;
optionally substituted aryl;
optionally substituted aryl lower alkyl; and
R⁴ is H, halogen, or lower alkyl;
p is 0, 1, or 2;
X is selected from the group consisting of O, S, and NH;
Y is selected from the group consisting of
lower alkylene, optionally substituted by OH or OAcyl;
—CH₂—O—;
—CH₂—S—;
—CH₂—NH—;
—O—;
—S—;
—NH—;
—(CR₂⁴)$_n$—S(O)$_p$—(5-membered heteroaryl)—(CR₂⁴)$_s$—;
—(CR₂⁴)$_n$—C(G²)(R⁴)—(CR₂⁴)$_s$—;
  wherein
    n and s are each independently 0 or an integer of 1–2; and
  G² is selected from the group consisting of —CN, —CO₂R³, —CON(R⁶)₂, and —CH₂N(R⁶)₂;
—O—CH₂—;
—S(O)—;
—S(O)₂—;
—SCH₂—;
—S(O)CH₂—;
—S(O)₂CH₂—;
—CH₂S(O)—; and
—CH₂S(O)₂—;
A and D independently represent N or CH;
B and E independently represent N or CH;
L represents N or CH;
  with the provisos that
    a) the total number of N atoms in the ring containing A, B, D, E, and L is 1 or 2; and
    b) when L represents CH, at least one of A and D is an N atom;
q is 1 or 2;
G³ is selected from the group consisting of
—NR³COR⁶;
carboxy-substituted alkyl;
lower alkoxycarbonyl-substituted alkyl;
—OR⁶;
—SR⁶;
—S(O)R⁶;
—S(O)₂R⁶;
—OCOR⁶;
—COR⁶;
—CO₂R⁶;
—CH₂OR³;
—CON(R⁶)₂;
—S(O)₂N(R⁶)₂;
—NO₂;
—CN;
optionally substituted aryl;
optionally substituted heteroaryl;
optionally substituted saturated heterocyclyl;
optionally substituted partially unsaturated heterocyclyl;
optionally substituted heteroarylalkyl;
optionally substituted heteroaryloxy;
—S(O)$_p$(optionally substituted heteroaryl);
optionally substituted heteroarylalkyloxy;
—S(O)$_p$(optionally substituted heteroarylalkyl);
—OCON(R⁶)₂;
—NR³CO₂R⁶; and
—NR³CON(R⁶)₂;
J is a ring selected from the group consisting of
aryl;
pyridyl; and
cycloalkyl;
q' represents the number of substituents G⁴ on ring J and is 0, 1, 2, 3, 4, or 5; and
G⁴ moieties are selected from the group consisting of
—N(R⁶)₂;
—NR³COR⁶;
halogen;
alkyl;
cycloalkyl;
lower alkenyl;
lower cycloalkenyl;
halogen-substituted alkyl;
amino-substituted alkyl;
N-lower alkylamino-substituted alkyl;
N,N-di-lower alkylamino-substituted alkyl;

N-lower alkanoylamino-substituted alkyl;
hydroxy-substituted alkyl;
cyano-substituted alkyl;
carboxy-substituted alkyl;
lower alkoxycarbonyl-substituted alkyl;
phenyl lower alkoxycarbonyl-substituted alkyl;
halogen-substituted alkylamino;
amino-substituted alkylamino;
N-lower alkylamino-substituted alkylamino;
N,N-di-lower alkylamino-substituted alkylamino;
N-lower alkanoylamino-substituted alkylamino;
hydroxy-substituted alkylamino;
cyano-substituted alkylamino;
carboxy-substituted alkylamino;
lower alkoxycarbonyl-substituted alkylamino;
phenyl-lower alkoxycarbonyl-substituted alkylamino;
—$OR^6$;
—$SR^6$;
—$S(O)R^6$;
—$S(O)_2R^6$;
halogenated lower alkoxy;
halogenated lower alkylthio;
halogenated lower alkylsulfonyl;
—$OCOR^6$;
—$COR^6$;
—$CO_2R^6$;
—$CON(R^6)_2$;
—$CH_2OR^3$;
—$NO_2$;
—CN;
amidino;
guanidino;
sulfo;
—$B(OH)_2$;
optionally substituted aryl;
optionally substituted heteroaryl;
optionally substituted saturated heterocyclyl;
optionally substituted partially unsaturated heterocyclyl;
—$OCO_2R^3$;
optionally substituted heteroarylalkyl;
optionally substituted heteroaryloxy;
—$S(O)_p$(optionally substituted heteroaryl);
optionally substituted heteroarylalkyloxy;
—$S(O)_p$(optionally substituted heteroarylalkyl);
—CHO;
—$OCON(R^6)_2$;
—$NR^3CO_2R^6$;
—$NR^3CON(R^6)_2$; and
fused ring-forming bridges attached to and connecting adjacent positions of ring J, said bridges having the structures:

a)

wherein
each $T^2$ independently represents N, CH, or $CG^4$;
$T^3$ represents S, O, $CR^4G^4$, $C(R^4)_2$, or $NR^3$; and
bonding to ring J is achieved via terminal atoms $T^2$ and $T^3$;

b)

wherein
each $T^2$ independently represents N, CH, or $CG^4$;
with the proviso that a maximum of two bridge atoms $T^2$ may be N; and
bonding to ring J is achieved via terminal atoms $T^2$; and c)

wherein
each $T^4$, $T^5$, and $T^6$ independently represents O, S, $CR^4G^4$, $C(R^4)_2$, or $NR^3$; and
bonding to ring J is achieved via terminal atoms $T^4$ or $T^5$;
with the provisos that:
i) when one $T^4$ is O, S, or $NR^3$, the other $T^4$ is $CR^4G^4$ or $C(R^4)_2$;
ii) a bridge comprising $T^5$ and $T^6$ atoms may contain a maximum of two heteroatoms O, S, or N; and
iii) in a bridge comprising $T^5$ and $T^6$ atoms, when one $T^5$ group and one $T^6$ group are O atoms, or two $T^6$ groups are O atoms, said O atoms are separated by at least one carbon atom;
and with the further provisos that:
in $G^1$, $G^2$, $G^3$, and $G^4$, when two groups $R^6$ are each alkyl and located on the same N atom they may be linked by a bond, an O, an S, or $NR^3$ to form a heterocycle of 5–7 ring atoms; and
when an aryl, heteroaryl, or heterocyclyl ring is optionally substituted, that ring may bear up to 5 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —$CO_2R^3$, —CHO, —$CH_2OR^3$, —$OCO_2R^3$, —$CON(R^6)_2$, —$OCO\ N(R^6)_2$, —$NR^3CON(R^6)_2$, nitro, amidino, guanidino, mercapto, sulfo, and cyano;
or a pharmaceutically acceptable salt thereof.

7. A compound having the structural formula

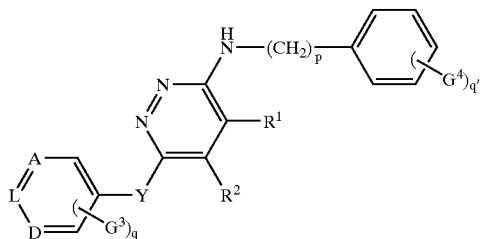

wherein
R¹ and R²:
together form a bridge of structure

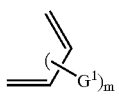

wherein bonding is achieved via the terminal carbon atoms;
wherein
m is 0 or an integer 1–2; and
G¹ is a substituent independently selected from the group consisting of
—N(R$^6$)$_2$;
—NR$^3$COR$^1$;
halogen;
alkyl;
amino-substituted alkylamino;
N-lower alkylamino-substituted alkylamino;
N,N-di-lower alkylamino-substituted alkylamino;
N-lower alkanoylamino-substituted alkylamino;
hydroxy-substituted alkylamino;
carboxy-substituted alkylamino;
lower alkoxycarbonyl-substituted alkylamino;
—OR$^6$;
—SR$^6$;
—S(O)R$^6$;
—S(O)$_2$R$^6$;
halogenated lower alkoxy;
halogenated lower alkylthio;
halogenated lower alkylsulfonyl;
—OCOR$^6$;
—COR$^6$;
—CO$_2$R$^6$;
—CON(R$^6$)$_2$;
—NO$_2$;
—CN;
optionally substituted heteroarylalkyl;
optionally substituted heteroaryloxy;
—S(O)$_p$(optionally substituted heteroaryl);
optionally substituted heteroarylalkyloxy; and
—S(O)$_p$(optionally substituted heteroarylalkyl);
R$^3$ is H or lower alkyl;
R$^6$ is independently selected from the group consisting of
H;
lower alkyl;
optionally substituted aryl;
optionally substituted aryl lower alkyl; and
p is 0 or 1;
Y is selected from the group consisting of
lower alkylene, optionally substituted by OH or OAcyl;
—CH$_2$—O—;
—CH$_2$—S—;
—CH$_2$—NH—;
—O—;
—S—;
—NH—;
—(CH$_2$)$_n$—S(O)$_p$—(5-membered heteroaryl)—(CH$_2$)$_s$—;
—(CH$_2$)$_n$—C(G$^2$)(H)—(CH$_2$)$_s$—;
wherein
n and s are each independently 0 or 1; and
G$^2$ is selected from the group consisting of —CN, —CO$_2$R$^3$, —CON(R$^6$)$_2$, and —CH$_2$N(R$^6$)$_2$;
—O—CH$_2$—;
—S(O)—;
—S(O)$_2$—;
—SCH$_2$—;
—S(O)CH$_2$—;
—S(O)$_2$CH$_2$—;
—CH$_2$S(O)—; and
—CH$_2$S(O)$_2$;
A and D independently represent N or CH;
L represents N or CH;
with the provisos that
a) the total number of N atoms in the ring containing A, D, and L is 1 or 2; and
b) when L represents CH, at least one of A and D is an N atom;
q is 1 or 2;
G$^3$ is selected from the group consisting of
—NR$^3$COR$^6$;
—OR$^6$;
—SR$^6$;
—S(O)R$^6$;
—S(O)$_2$R$^6$;
—CO$_2$R$^6$;
—CON(R$^6$)$_2$;
—S(O)$_2$N(R$^6$)$_2$;
—CN;
optionally substituted aryl;
optionally substituted heteroaryl;
optionally substituted heteroarylalkyl;
optionally substituted heteroaryloxy,
—S(O)$_p$(optionally substituted heteroaryl);
optionally substituted heteroarylalkyloxy; and
—S(O)$_p$(optionally substituted heteroarylalkyl);
q' represents the number of substituents G$^4$ on the phenyl ring and is 0, 1, 2, or 3; and
G$^4$ moieties are selected from the group consisting of
—N(R$^6$)$_2$;
—NR$^3$COR$^6$;
halogen;
alkyl;
halogen-substituted alkyl;

hydroxy-substituted alkyl;
carboxy-substituted alkyl;
lower alkoxycarbonyl-substituted alkyl;
amino-substituted alkylamino;
N-lower alkylamino-substituted alkylamino;
N,N-di-lower alkylamino-substituted alkylamino;
N-lower alkanoylamino-substituted alkylamino;
hydroxy-substituted alkylamino;
carboxy-substituted alkylamino;
lower alkoxycarbonyl-substituted alkylamino;
phenyl-lower alkoxycarbonyl-substituted alkylamino;
—$OR^6$;
—$SR^6$;
—$S(O)R^6$;
—$S(O)_2R^6$;
halogenated lower alkoxy;
halogenated lower alkylthio;
halogenated lower alkylsulfonyl;
—$OCOR^6$;
—$COR^6$;
—$CO_2R^6$;
—$CON(R^6)_2$;
—$CH_2OR^3$;
—$NO_2$;
—CN;
optionally substituted heteroarylalkyl;
—$S(O)_p$(optionally substituted heteroaryl);
optionally substituted heteroaryloxy;
—$S(O)_p$(optionally substituted heteroarylalkyl); and
fused ring-forming bridges attached to and connecting adjacent positions of the phenyl ring, said bridges having the structures:
a)

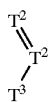

wherein
each $T^2$ independently represents N, CH, or $CG^4$;
$T^3$ represents S, O, $CHG^4$, $C(H)_2$, or $NR^3$; and
bonding to the phenyl ring is achieved via terminal atoms $T^2$ and $T^3$;

b)

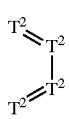

wherein
each $T^2$ independently represents N, CH, or $CG^4$;
with the proviso that a maximum of two bridge atoms $T^2$ may be N; and
bonding to the phenyl ring is achieved via terminal atoms $T^2$; and c)

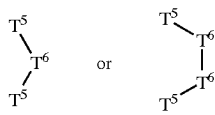

wherein
each $T^5$, and $T^6$ independently represents O, S, $CHG^4$, $C(H)_2$, or $NR^3$; and
bonding to the phenyl ring is achieved via terminal atoms $T^5$;
with the provisos that:
i) a bridge comprising $T^5$ and $T^6$ atoms may contain a maximum of two heteroatoms O, S, or N; and
ii) in a bridge comprising $T^5$ and $T^6$ atoms, when one $T^5$ group and one $T^6$ group are O atoms, or two $T^6$ groups are O atoms, said O atoms are separated by at least one carbon atom;
and with the further provisos that:
in $G^1$, $G^2$, $G^3$, and $G^4$, when two groups $R^6$ are each alkyl and located on the same N atom they may be linked by a bond, an O, an S, or $NR^3$ to form a heterocycle of 5–7 ring atoms; and
when an aryl, heteroaryl, or heterocyclyl ring is optionally substituted, that ring may bear up to 2 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —$CO_2R^3$, —$CH_2OR^3$, —$OCO_2R^3$, —$CON(R^6)_2$, —$OCO N(R^6)_2$, —$NR^3CON(R^6)_2$, nitro, and cyano;
or a pharmaceutically acceptable salt thereof.

8. A compound having the structural formula

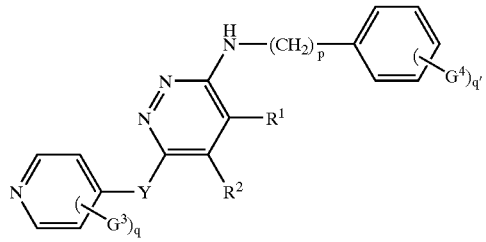

wherein
$R^1$ and $R^2$:
together form a bridge of structure

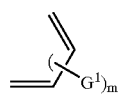

wherein bonding is achieved via the terminal carbon atoms, and any group $G^1$ is located on a non-terminal atom of the bridge;

wherein
m is 0 or an integer 1–2; and
G$^1$ is a substituent independently selected from the group consisting of
—N(R$^6$)$_2$;
—NR$^3$COR$^6$;
halogen;
—OR$^6$ wherein R6 represents lower alkyl;
—NO$_2$;
optionally substituted heteroaryloxy; and
optionally substituted heteroarylalkyloxy;
R$^3$ is H or lower alkyl;
R$^6$ is independently selected from the group consisting of
H;
lower alkyl;
optionally substituted aryl;
optionally substituted aryl lower alkyl; and
p is 0 or 1;
Y is selected from the group consisting of
lower alkylene, optionally substituted by OH;
—CH$_2$—O—;
—S—;
—NH—;
—S(O)$_p$—(5-membered heteroaryl)—;
—C(CN)(H)—;
—O—CH$_2$—;
—S(O)—; and
—S(O)$_2$—;
q is 1;
G$^3$ is selected from the group consisting of
—NR$^3$COR$^6$;
—CO$_2$R$^6$;
—CON(R$^6$)$_2$; and
—S(O)$_2$N(R$^6$)$_2$;
q represents the number of substituents G$^4$ on the phenyl ring and is 0, 1, 2, or 3; and
G$^4$ moieties are selected from the group consisting of
—N(R$^6$)$_2$;
halogen;
lower alkyl;
halogen-substituted lower alkyl;
—OR$^6$;
—SR$^6$;
—S(O)R$^6$;
—S(O)$_2$R$^6$;
halogenated lower alkoxy,
halogenated lower alkylthio;
halogenated lower alkylsulfonyl;
—OCOR$^6$;
—COR$^6$;
—CO$_2$R$^6$;
—CON(R$^6$)$_2$;
—CH$_2$OR$^3$;
—NO$_2$;
—CN;
optionally substituted heteroarylalkyl;
optionally substituted heteroaryloxy;
—S(O)$_p$(optionally substituted heteroaryl);
optionally substituted heteroarylalkyloxy;
—S(O)$_p$(optionally substituted heteroarylalkyl); and
fused ring-forming bridges attached to and connecting adjacent positions of the phenyl ring, said bridges having the structures:
a)

wherein
each T$^2$ independently represents N, CH, or CG$^4$;
T$^3$ represents S, O, CHG$^4$, CH$_2$, or NR$^3$; and
bonding to the phenyl ring is achieved via terminal atoms T$^2$ and T$^3$;
b)

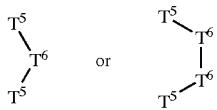

wherein
each T$^5$, and T$^6$ independently represents O, S, CHG$^4$, CH$_2$, or NR$^3$; and
bonding to the phenyl ring is achieved via terminal atoms T$^5$;
with the provisos that:
i) a bridge comprising T$^5$ and T$^6$ atoms may contain a maximum of two heteroatoms O, S, or N; and
ii) in a bridge comprising T$^5$ and T$^6$ atoms, when one T$^5$ group and one T$^6$ group are O atoms, or two T$^6$ groups are O atoms, said O atoms are separated by at least one carbon atom;
and with the further provisos that:
in G$^1$, G$^2$, G$^3$, and G$^4$, hen two groups R$^6$ are each alkyl and located on the same N atom they may be linked by a bond, an O, an S, or NR$^3$ to form a heterocycle of 5–6 ring atoms; and
when an aryl, heteroaryl, or heterocyclyl ring is optionally substituted, that ring may bear up to 2 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, —CO$_2$R$^3$, —CON(R$^6$)$_2$, nitro, and cyano;
or a pharmaceutically acceptable salt thereof.

9. A pharmaceutical composition comprising a compound of claim 6 and a pharmaceutically acceptable carrier.

10. A method of treating a mammal having a condition of tumor growth, retinopathy, rheumatoid arthritis, psoriasis, or a bullous disorder associated with subepidermal blister formation, comprising administering to said mammal an amount of a compound of claim 6 which is effective to treat said condition.

11. A compound having the structural formula

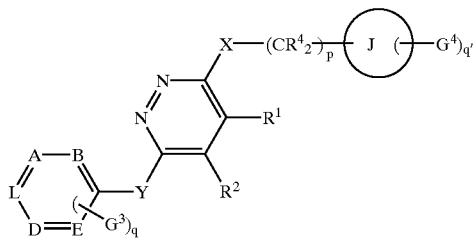

wherein
R¹ and R²:
together form a bridge of structure

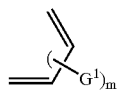

wherein bonding is achieved via the terminal carbon atoms; o
wherein
m is 0 or an integer 1–4; and
G¹ is a substituent independently selected from the group consisting of
—N(R⁶)₂;
—NR³COR⁶;
halogen;
alkyl;
cycloalkyl;
lower alkenyl;
lower cycloalkenyl;
halogen-substituted alkyl;
amino-substituted alkyl;
N-lower alkylamino-substituted alkyl;
N,N-di-lower alkylamino-substituted alkyl;
N-lower alkanoylamino-substituted alkyl;
hydroxy-substituted alkyl;
cyano-substituted alkyl;
carboxy-substituted alkyl;
lower alkoxycarbonyl-substituted alkyl;
phenyl lower alkoxycarbonyl-substituted alkyl;
halogen-substituted alkylamino;
amino-substituted alkylamino;
N-lower alkylamino-substituted alkylamino;
N,N-di-lower alkylamino-substituted alkylamino;
N-lower alkanoylamino-substituted alkylamino;
hydroxy-substituted alkyl amino;
cyano-substituted alkylamino;
carboxy-substituted alkylamino;
lower alkoxycarbonyl-substituted alkylamino;
phenyl-lower alkoxycarbonyl-substituted alkylamino;
—OR⁶;
—SR⁶;
—S(O)R⁶;
—S(O)₂R⁶;
halogenated lower alkoxy;
halogenated lower alkylthio;
halogenated lower alkylsulfonyl;
—OCOR⁶;
—COR⁶;
—CO₂R⁶;
—CON(R⁶)₂;
—CH₂OR³;
—NO₂;
—CN;
amidino;
guanidino;
sulfo;
—B(OH)₂;
optionally substituted aryl;
optionally substituted heteroaryl;
optionally substituted saturated heterocyclyl;
optionally substituted partially unsaturated heterocyclyl;
—OCO₂R³;
optionally substituted heteroarylalkyl;
optionally substituted heteroaryloxy;
—S(O)ₚ(optionally substituted heteroaryl);
optionally substituted heteroarylalkyloxy;
—S(O)ₚ(optionally substituted heteroarylalkyl);
—CHO;
—OCON(R⁶)₂;
—NR³CO₂R⁶; and
—NR³CON(R⁶)₂;
R³ is H or lower alkyl;
R⁶ is independently selected from the group consisting of
H;
alkyl;
optionally substituted aryl;
optionally substituted aryl lower alkyl; and
R⁴ is H, halogen, or lower alkyl;
p is 0, 1, or 2;
X is selected from the group consisting of O, S, and NH;
Y is selected from the group consisting of
lower alkylene, optionally substituted by OH or OAcyl;
—CH₂—O—;
—CH₂—S—;
—CH₂—NH—;
—O—;
—S—;
—NH—;
—(CR₂⁴)ₙ—S(O)ₚ—(5-membered heteroaryl)—(CR₂⁴)ₛ—;
—(CR₂⁴)ₙ—C(G²)(R⁴)—(CR₂⁴)ₛ—;
wherein
n and s are each independently 0 or an integer of 1–2; and
G² is selected from the group consisting of —CN, —CO₂R³, —CON(R⁶)₂, and —CH₂N(R⁶)₂;
—O—CH₂—;
—S(O)—;
—S(O)₂—;
—SCH₂—;
—S(O)CH₂—;
—S(O)₂CH₂—;
—CH₂S(O)—; and
—CH₂S(O)₂—;

A and D independently represent N or CH;
B and E independently represent N or CH;
L represents N or CH;
  with the provisos that
  a) the total number of N atoms in the ring containing A, B, D, E, and L is 1 or 2; and
  b) when L represents CH, at least one of A and D is an N atom;
q is 0, 1, or 2;
$G^3$ is selected from the group consisting of
  lower alkyl;
  —$NR^3COR^6$;
  carboxy-substituted alkyl;
  lower alkoxycarbonyl-substituted alkyl;
  —$OR^6$;
  —$SR^6$;
  —$S(O)R^6$;
  —$S(O)_2R^6$;
  —$OCOR^6$;
  —$COR^6$;
  —$CO_2R^6$;
  —$CH_2OR^3$;
  —$CON(R^6)_2$;
  —$S(O)_2N(R^6)_2$;
  —$NO_2$;
  —CN;
  optionally substituted aryl;
  optionally substituted heteroaryl;
  optionally substituted saturated heterocyclyl;
  optionally substituted partially unsaturated heterocyclyl;
  optionally substituted heteroarylalkyl;
  optionally substituted heteroaryloxy;
  —$S(O)_p$(optionally substituted heteroaryl);
  optionally substituted heteroarylalkyloxy;
  —$S(O)_p$(optionally substituted heteroarylalkyl);
  —$OCON^6(R^6)_2$;
  —$NR^3CO_2R^6$; and
  —$NR^3CON(R^6)_2$;
J is a ring selected from the group consisting of
  aryl;
  pyridyl; and
  cycloalkyl;
q' represents the number of substituents $G^4$ on ring J and is 1, 2, 3, 4, or 5; and
$G^4$ moieties are selected from the group consisting of
  optionally substituted heteroarylalkyl;
  optionally substituted heteroaryloxy;
  —$S(O)_p$(optionally substituted heteroaryl);
  optionally substituted heteroarylalkyloxy;
  —$S(O)_p$(optionally substituted heteroarylalkyl);
  —CHO;
  —$OCON(R^6)_2$;
  —$NR^3CO_2R^6$; and
  fused ring-forming bridges attached to and connecting adjacent positions of ring J, said bridges having the structures:

a)
  wherein
    each $T^2$ independently represents N, CH, or $CG^4$;
    $T^3$ represents S, O, $CR^4G^4$, $C(R^4)_2$, or $NR^3$; and
    bonding to ring J is achieved via terminal atoms $T^2$ and $T^3$;
b)
  wherein
    each $T^2$ independently represents N, CH, or $CG^4$;
    with the proviso that a maximum of two bridge atoms $T^2$ may be N; and
    bonding to ring J is achieved via terminal atoms $T^2$; and
c)
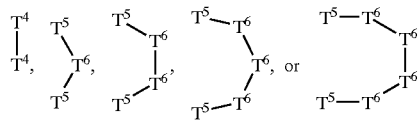
  wherein
    each $T^4$, $T^5$, and $T^6$ independently represents O, S, $CR^4G^4$, $C(R^4)_2$, or $NR^3$; and
    bonding to ring J is achieved via terminal atoms $T^4$ or $T^5$;
    with the provisos that:
      i) when one $T^4$ is O, S, or $NR^3$, the other $T^4$ is $CR^4G^4$ or $C(R^4)_2$;
      ii) a bridge comprising $T^5$ and $T^6$ atoms may contain a maximum of two heteroatoms O, S, or N; and
      iii) in a bridge comprising $T^5$ and $T^6$ atoms, when one $T^5$ is O, the other $T^5$ is S, $CR^4G^4$, $C(R^4)_2$ or $NR^3$;
      iv) in a bridge comprising $T^5$ and $T^6$ atoms, when one $T^5$ group and one $T^6$ group are O atoms, or two $T^6$ groups are O atoms, said O atoms are separated by at least one carbon atom;
and with the further provisos that:
  in $G^1$, $G^2$, $G^3$, and $G^4$, when two groups $R^6$ are each alkyl and located on the same N atom they may be linked by a bond, an O, an S, or $NR^3$ to form a heterocycle of 5–7 ring atoms; and
  when an aryl, heteroaryl, or heterocyclyl ring is optionally substituted, that ring may bear up to 5 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —$CO_2R^3$, —CHO, —$CH_2OR^3$, —$OCO_2R^3$, —$CON(R^6)_2$, —OCO $N(R^6)_2$—$NR^3CON(R^6)_2$, nitro, amidino, guanidino, mercapto, sulfo, and cyano;
or a pharmaceutically acceptable salt thereof.

12. A compound having the structural formula

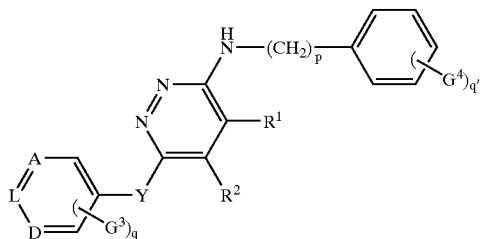

wherein
R¹ and R²:
together form a bridge of structure

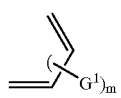

wherein bonding is achieved via the terminal carbon atoms;
wherein
m is 0 or an integer 1–2; and
G is a substituent independently selected from the group consisting of
—N(R⁶)₂;
—NR³COR⁶;
halogen;
alkyl;
amino-substituted alkylamino;
N-lower alkylamino-substituted alkylamino;
N,N-di-lower alkylamino-substituted alkylamino;
N-lower alkanoylamino-substituted alkylamino;
hydroxy-substituted alkylamino;
carboxy-substituted alkylamino;
lower alkoxycarbonyl-substituted alkylamino;
—OR⁶;
—SR⁶;
—S(O)R⁶;
—S(O)₂R⁶;
halogenated lower alkoxy;
halogenated lower alkylthio;
halogenated lower alkylsulfonyl;
—OCOR⁶;
—COR⁶;
—CO₂R⁶;
—CON(R⁶)₂;
—NO₂;
—CN;
optionally substituted heteroarylalkyl;
optionally substituted heteroaryloxy;
—S(O)ₚ(optionally substituted heteroaryl);
optionally substituted heteroarylalkyloxy; and
—S(O)ₚ(optionally substituted heteroarylalkyl);
R³ is H or lower alkyl;
R⁶ is independently selected from the group consisting of
H;
lower alkyl;
optionally substituted aryl;
optionally substituted aryl lower alkyl; and
p is 0 or 1;
Y is selected from the group consisting of
lower alkylene, optionally substituted by OH or OAcyl;
—CH₂—O—;
—CH₂—S—;
—CH₂—NH—;
—O—;
—S—;
—NH—;
—(CH₂)ₙ—S(O)ₚ—(5-membered heteroaryl)—(CH₂)ₛ—;
—(CH₂)ₙ—C(G²)(H)—(CH₂)ₛ—;
wherein
n and s are each independently 0 or 1; and
G is selected from the group consisting of —CN, —CO₂R³, —CON(R⁶)₂, and —CH₂N(R⁶)₂;
—O—CH₂—;
—S(O)—;
—S(O)₂—;
—SCH₂—;
—S(O)CH₂—;
—S(O)₂CH₂—;
—CH₂S(O)—; and
—CH₂S(O)₂;
A and D independently represent N or CH;
L represents N or CH;
with the provisos that
a) the total number of N atoms in the ring containing A, D, and L is 1 or 2; and
b) when L represents CH, at least one of A and D is an N atom;
q is 0, 1, or 2;
G³ is selected from the group consisting of
lower alkyl;
—NR³COR⁶;
—OR⁶;
—SR⁶;
—S(O)R⁶;
—S(O)₂R⁶;
—CO₂R⁶;
—CON(R⁶)₂;
—S(O)₂N(R⁶)₂;
—CN;
optionally substituted aryl;
optionally substituted heteroaryl;
optionally substituted heteroarylalkyl;
optionally substituted heteroaryloxy;
—S(O)ₚ(optionally substituted heteroaryl);
optionally substituted heteroarylalkyloxy; and
—S(O)ₚ(optionally substituted heteroarylalkyl);
q' represents the number of substituents G⁴ on the phenyl ring and is 1, 2, or 3; and
G⁴ moieties are selected from the group consisting of
optionally substituted heteroarylalkyl;
optionally substituted heteroaryloxy;
—S(O)ₚ(optionally substituted heteroaryl);
optionally substituted heteroarylalkyloxy;

—S(O)$_p$(optionally substituted heteroarylalkyl); and fused ring-forming bridges attached to and connecting adjacent positions of the phenyl ring, said bridges having the structures:

a)

wherein
each T$^2$ independently represents N, CH, or CG$^4$;
T$^3$ represents S, O, CHG$^4$, C(H)$_2$, or NR$^3$; and
bonding to the phenyl ring is achieved via terminal atoms T$^2$ and T$^3$;

b)

wherein
each T$^2$ independently represents N, CH, or CG$^4$;
with the proviso that a maximum of two bridge atoms T$^2$ may be N; and
bonding to the phenyl ring is achieved via terminal atoms T$^2$; and c)

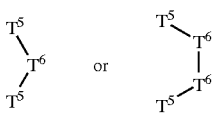

wherein
each T$^5$, and T$^6$ independently represents O, S, CHG$^4$, CH$_2$, or NR$^3$; and
bonding to the phenyl ring is achieved via terminal atoms T$^5$;
with the provisos that:
i) a bridge comprising T$^5$ and T$^6$ atoms may contain a maximum of two heteroatoms O, S, or N; and
ii) in a bridge comprising T$^5$ and T$^6$ atoms, when one T$^5$ is O, the other T$^5$ is S, CHG$^4$, CH$_2$ or NR$^3$;
iii) in a bridge comprising T$^5$ and T$^6$ atoms, when one T$^5$ group and one T$^6$ group are O atoms, or two T$^6$ groups are O atoms, said O atoms are separated by at least one carbon atom;

and with the further provisos that:
in G$^1$, G$^2$, G$^3$, and G$^4$, when two groups R$^6$ are each alkyl and located on the same N atom they may be linked by a bond, an 0, an S, or NR$^3$ to form a heterocycle of 5–7 ring atoms; and when an aryl, heteroaryl, or heterocyclyl ring is optionally substituted, that ring may bear up to 2 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, lower alkanoyloxy, —CO$_2$R$^3$, —CH$_2$OR$^3$, —OCO$_2$R$^3$, —CON(R$^6$)$_2$, —OCO N(R$^6$)$_2$, —NR$^3$CON(R$^6$)$_2$, nitro, and cyano;
or a pharmaceutically acceptable salt thereof.

13. A compound having the structural formula

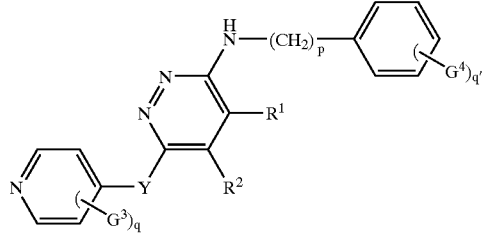

wherein
R$^1$ and R$^2$:
together form a bridge of structure

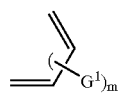

wherein bonding is achieved via the terminal carbon atoms, and any group G$^1$ is located on a non-terminal atom of the bridge;
wherein
m is 0 or an integer 1–2; and
G$^1$ is a substituent independently selected from the group consisting of
—N(R$^6$)$_2$;
—NR$^3$COR$^6$;
halogen;
—OR$^6$ wherein R6 represents lower alkyl;
—NO$_2$;
optionally substituted heteroaryloxy; and
optionally substituted heteroarylalkyloxy;
R$^3$ is H or lower alkyl;
R$^6$ is independently selected from the group consisting of
H;
lower alkyl;
optionally substituted aryl;
optionally substituted aryl lower alkyl; and
p is 0 or 1;
Y is selected from the group consisting of
lower alkylene, optionally substituted by OH;
—CH$_2$—O—;
—S—;
—NH—;
—S(O)$_p$—(5-membered heteroaryl)—;
—C(CN)(H)—;
—O—CH$_2$—;
—S(O)—; and
—S(O)$_2$—;
q is 0 or 1;
G$^3$ is selected from the group consisting of
lower alkyl;
—NR$^3$COR$^6$;
—CO$_2$R$^6$;
—CON(R$^6$)$_2$; and
—S(O)$_2$N(R$^6$)$_2$;

q' represents the number of substituents $G^4$ on the phenyl ring, and is 1, 2, or 3; and $G^4$ moieties are selected from the group consisting of
optionally substituted heteroarylalkyl;
optionally substituted heteroaryloxy;
—$S(O)_p$(optionally substituted heteroaryl);
optionally substituted heteroarylalkyloxy;
—$S(O)_p$(optionally substituted heteroarylalkyl); and
fused ring-forming bridges attached to and connecting adjacent positions of the phenyl ring, said bridges having the structures:

a)

wherein
each $T^2$ independently represents N, CH, or $CG^4$;
$T^3$ represents S, O, $CHG^4$, $CH_2$, or $NR^3$; and
bonding to the phenyl ring is achieved via terminal atoms $T^2$ and $T^3$;

b)

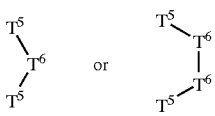

wherein
each $T^5$, and $T^6$ independently represents O, S, $CHG^4$, $CH_2$, or $NR^3$; and
bonding to the phenyl ring is achieved via terminal atoms $T^5$;

with the provisos that:
i) a bridge comprising $T^5$ and $T^6$ atoms may contain a maximum of two heteroatoms O, S, or N; and
ii) in a bridge comprising $T^5$ and $T^6$ atoms, when one $T^5$ is O, the other $T^5$ is S, $CR^4G^4$, $C(R^4)_2$ or $NR^3$;
iii) in a bridge comprising $T^5$ and $T^6$ atoms, when one $T^5$ group and one $T^6$ group are O atoms, or two $T^6$ groups are O atoms, said O atoms are separated by at least one carbon atom;

and with the further provisos that:
in $G^1$, $G^2$, $G^3$, and $G^4$, when two groups $R^6$ are each alkyl and located on the same N atom they may be linked by a bond, an O, an S, or $NR^3$ to form a heterocycle of 5–6 ring atoms; and
when an aryl, heteroaryl, or heterocyclyl ring is optionally substituted, that ring may bear up to 2 substituents which are independently selected from the group consisting of amino, mono-loweralkyl-substituted amino, di-loweralkyl-substituted amino, lower alkanoylamino, halogeno, lower alkyl, halogenated lower alkyl, hydroxy, lower alkoxy, lower alkylthio, halogenated lower alkoxy, halogenated lower alkylthio, —$CO_2R^3$, —$CON(R^6)_2$, nitro, and cyano;

or a pharmaceutically acceptable salt thereof.

14. A pharmaceutical composition comprising a compound of claim 11 and a pharmaceutically acceptable carrier.

15. A method of treating a mammal having a condition of tumor growth, retinopathy, rheumatoid arthritis, psoriasis, or a bullous disorder associated with subepidermal blister formation, comprising administering to said mammal an amount of a compound of claim 11 which is effective to treat said condition.

16. A compound selected from the group consisting of:
a) 4-[4-(4-Chlorophenylamino)phthalazin-1-ylmethyl] pyridin-2-yl carboxylic acid methylamide;
b) 4-[4-(4-Chlorophenylamino)phthalazin-1-ylmethyl] pyridin-2-yl carboxylic acid amide;
c) 1-(4-chlorophenylamino)-4-(3-pyridylmethoxy) phthalazine;
d) 4-[4-(4-Chlorophenylamino)phthalazin-1-yloxymethyl]pyridin-2-yl carboxylic acid methylamide;
e) 4-[4-(4-Chlorophenylamino)phthalazin-1-yloxymethyl]pyridin-2-yl carboxylic acid amide;
f) 4-[4-(3-Bromophenylamino)phthalazin-1-ylmethyl]-pyridin-2-yl carboxylic acid methylamide;
g) 4-[4-(3-Bromophenylamino)phthalazin-1-ylmethyl]-pyridin-2-yl carboxylic acid amide;
h) 1-(4-chlorophenylamino)-4-[(2-phenyl-4-pyridyl)methyl]phthalazine;
i) 1-[4-(4-pyridyloxy)phenylamino]-4-(4-pyridylmethyl) phthalazine;
j) 1-(indan-5-ylamino)-4-(4-pyridylmethyl)phthalazine;
k) 4-[4-(4-Chlorophenylamino)phthalazin-1-ylmethyl] pyridin-2-yl carboxylic acid methylamide dihydrochloride;
l) 4-[4-(4-Chlorophenylamino)phthalazin-1-ylmethyl] pyridin-2-yl carboxylic acid methylamide dimethanesulfonate;
m) 4-[4-(4-Chlorophenylamino)phthalazin-1-ylmethyl] pyridin-2-yl carboxylic acid amide dihydrochloride;
n) 4-[4-(4-Chlorophenylamino)phthalazin-1-ylmethyl] pyridin-2-yl carboxylic acid amide dimethanesulfonate;
o) 4-[4-(4-Chlorophenylamino)phthalazin-1-yloxymethyl]pyridin-2-yl carboxylic acid amide dihydrochloride;
p) 4-[4-(4-Chlorophenylamino)phthalazin-1-yloxymethyl]pyridin-2-yl carboxylic acid amide dimethanesulfonate;
q) 1-(4-chlorophenylamino)-4-[5-(4-pyridyl)-1H-1,2,4-triazolyl-3-ylthio]phthalazine;
r) 1-(4-isopropylphenylamino)-4-[5-(4-pyridyl)-1H-1,2,4-triazolyl-3-ylthio]phthalazine;
s) 1-(4-chlorophenylamino)-4-(4-pyridylsufonyl) phthalazine;
t) 1-(4-chlorophenylamino)-4-(4-pyridylsufinyl) phthalazine;
v) 1-(indan-5-ylamino)-4-(4-pyridylcyanomethyl) phthalazine; and
w) 1-(benzothiazol-6-ylamino)-4-(4-pyridylcyanomethyl)phthalazine.

17. The method of claim 5, wherein said condition of retinopathy is diabetic retinopathy, ischemic retinal-vein occlusion, retinopathy of prematurity, or age-related macular degeneration.

18. The method of claim 5, wherein when said condition is a bullous disorder associated with subepidermal blister formation, it is bullous pemphigoid, erythema multiforme, or dermatitis herpetiformis.

19. The method of claim 10, wherein said condition of retinopathy is diabetic retinopathy, ischemic retinal-vein occlusion, retinopathy of prematurity, or age-related macular degeneration.

20. The method of claim 10, wherein when said condition is a bullous disorder associated with subepidermal blister formation, it is bullous pemphigoid, erythema multiforme, or dermatitis herpetiformis.

21. The method of claim 15, wherein said condition of retinopathy is diabetic retinopathy, ischemic retinal-vein occlusion, retinopathy of prematurity, or age-related macular degeneration.

22. The method of claim 15, wherein when said condition is a bullous disorder associated with subepidermal blister formation, it is bullous pemphigoid, erythema multiforme, or dermatitis herpetiformis.

* * * * *